United States Patent
Criado et al.

(10) Patent No.: US 10,543,307 B2
(45) Date of Patent: *Jan. 28, 2020

(54) METHODS AND SYSTEMS FOR ESTABLISHING RETROGRADE CAROTID ARTERIAL BLOOD FLOW

(71) Applicant: Silk Road Medical, Inc., Sunnyvale, CA (US)

(72) Inventors: Enrique Criado, Sunnyvale, CA (US); Tony M. Chou, Sunnyvale, CA (US); Michi E. Garrison, Sunnyvale, CA (US); Gregory M. Hyde, Sunnyvale, CA (US); Alan Schaer, Sunnyvale, CA (US); Richard Renati, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/008,703

(22) Filed: Jun. 14, 2018

(65) Prior Publication Data

US 2018/0289884 A1 Oct. 11, 2018

Related U.S. Application Data

(63) Continuation of application No. 15/728,747, filed on Oct. 10, 2017, now Pat. No. 10,426,885, which is a
(Continued)

(51) Int. Cl.
*A61M 1/36* (2006.01)
*A61M 29/02* (2006.01)
(Continued)

(52) U.S. Cl.
CPC ............. *A61M 1/3655* (2013.01); *A61B 8/06* (2013.01); *A61B 8/488* (2013.01);
(Continued)

(58) Field of Classification Search
CPC .............. A61M 1/3655; A61M 1/3613; A61M 1/3659; A61M 1/34; A61M 1/36;
(Continued)

(56) References Cited

U.S. PATENT DOCUMENTS

| 3,861,416 A | 1/1975 | Wichterle |
| 4,218,313 A | 8/1980 | Aid et al. |

(Continued)

FOREIGN PATENT DOCUMENTS

| EP | 0427429 A2 | 5/1991 |
| EP | 0 669 103 A1 | 8/1995 |

(Continued)

OTHER PUBLICATIONS

Adami, M.D., et al., (2002) "Use of the Parodi Anti-Embolism System in Carotid Stenting: Italian Trial Results" J Endovasc Ther 2002; 9:147-154.

(Continued)

*Primary Examiner* — Philip R Wiest
(74) *Attorney, Agent, or Firm* — Mintz Levin Cohn Ferris Glovsky and Popeo, P.C.

(57) ABSTRACT

Interventional procedures on the carotid arteries are performed through a transcervical access while retrograde blood flow is established from the internal carotid artery to a venous or external location. A system for use in accessing and treating a carotid artery includes an arterial access device, a shunt fluidly connected to the arterial access device, and a flow control assembly coupled to the shunt and adapted to regulate blood flow through the shunt between at least a first blood flow state and at least a second blood flow state. The flow control assembly includes one or more components that interact with the blood flow through the shunt.

55 Claims, 22 Drawing Sheets

Related U.S. Application Data continuation of application No. 15/168,809, filed on May 31, 2016, now Pat. No. 9,789,242, which is a continuation of application No. 14/475,346, filed on Sep. 2, 2014, now Pat. No. 9,833,555, which is a continuation of application No. 13/050,876, filed on Mar. 17, 2011, now Pat. No. 9,011,364, which is a continuation of application No. 12/176,250, filed on Jul. 18, 2008, now Pat. No. 8,157,760.

(60) Provisional application No. 61/026,308, filed on Feb. 5, 2008, provisional application No. 60/950,384, filed on Jul. 18, 2007.

(51) Int. Cl.

| | | |
|---|---|---|
| *A61M 25/10* | (2013.01) | |
| *A61B 8/06* | (2006.01) | |
| *A61B 8/08* | (2006.01) | |
| *A61B 17/12* | (2006.01) | |
| *A61F 2/82* | (2013.01) | |
| *A61F 2/95* | (2013.01) | |
| *A61M 1/34* | (2006.01) | |
| *A61M 5/00* | (2006.01) | |
| *A61M 39/06* | (2006.01) | |
| *A61M 39/22* | (2006.01) | |
| *A61B 17/00* | (2006.01) | |
| *A61B 17/3207* | (2006.01) | |
| *A61F 2/90* | (2013.01) | |
| *A61F 2/954* | (2013.01) | |
| *A61F 2/06* | (2013.01) | |

(52) U.S. Cl.
CPC .. *A61B 17/12045* (2013.01); *A61B 17/12109* (2013.01); *A61F 2/82* (2013.01); *A61F 2/95* (2013.01); *A61M 1/34* (2013.01); *A61M 1/36* (2013.01); *A61M 1/3613* (2014.02); *A61M 1/3659* (2014.02); *A61M 5/007* (2013.01); *A61M 25/10* (2013.01); *A61M 29/02* (2013.01); *A61M 39/06* (2013.01); *A61M 39/22* (2013.01); *A61B 2017/00778* (2013.01); *A61B 2017/12127* (2013.01); *A61B 2017/320716* (2013.01); *A61F 2/90* (2013.01); *A61F 2/954* (2013.01); *A61F 2002/065* (2013.01); *A61F 2250/0037* (2013.01); *A61M 2025/1052* (2013.01); *A61M 2205/33* (2013.01); *A61M 2205/3331* (2013.01); *A61M 2205/3334* (2013.01)

(58) Field of Classification Search
CPC ...... A61M 29/02; A61M 39/06; A61M 39/22; A61B 8/06; A61B 8/488; A61B 17/12045; A61B 17/12109; A61B 2017/00778; A61B 2017/12127; A61B 2017/320716; A61F 2/82; A61F 2/95
See application file for complete search history.

(56) References Cited

U.S. PATENT DOCUMENTS

| | | | |
|---|---|---|---|
| 4,253,201 A | 3/1981 | Ross et al. | |
| 4,301,803 A | 11/1981 | Handa et al. | |
| 4,493,707 A | 1/1985 | Ishihara | |
| 4,771,777 A | 9/1988 | Horzewski et al. | |
| 4,840,690 A | 6/1989 | Melinyshyn et al. | |
| 4,865,581 A | 9/1989 | Lundquist et al. | |
| 4,895,346 A | 1/1990 | Steigerwald | |
| 4,921,478 A | 5/1990 | Solano et al. | |
| 4,921,479 A | 5/1990 | Grayzel | |
| 5,007,921 A | 4/1991 | Brown | |
| 5,026,390 A | 6/1991 | Brown | |
| 5,031,636 A | 7/1991 | Gambale et al. | |
| 5,045,061 A | 9/1991 | Seifert et al. | |
| 5,061,275 A | 10/1991 | Wallsten et al. | |
| 5,135,484 A | 8/1992 | Wright | |
| 5,163,906 A | 11/1992 | Ahmadi | |
| 5,176,652 A | 1/1993 | Littrell | |
| 5,207,656 A | 5/1993 | Kranys | |
| 5,250,060 A | 10/1993 | Carbo et al. | |
| 5,304,184 A | 4/1994 | Hathaway et al. | |
| 5,306,250 A | 4/1994 | March et al. | |
| 5,312,356 A | 5/1994 | Engelson et al. | |
| RE34,633 E | 6/1994 | Sos et al. | |
| 5,324,262 A | 6/1994 | Fischell et al. | |
| 5,328,470 A | 7/1994 | Nabel et al. | |
| 5,328,471 A | 7/1994 | Slepian | |
| 5,380,284 A | 1/1995 | Don Michael | |
| 5,389,090 A | 2/1995 | Fischell et al. | |
| 5,403,328 A | 4/1995 | Shallman | |
| 5,429,605 A | 7/1995 | Bernd et al. | |
| 5,429,609 A | 7/1995 | Yoon | |
| 5,437,632 A | 8/1995 | Engelson | |
| 5,443,454 A | 8/1995 | Tanabe et al. | |
| 5,454,795 A | 10/1995 | Samson | |
| 5,460,616 A | 10/1995 | Weinstein et al. | |
| 5,476,450 A | 12/1995 | Ruggio | |
| 5,476,469 A | 12/1995 | Hathaway et al. | |
| 5,478,328 A | 12/1995 | Silverman et al. | |
| 5,484,412 A | 1/1996 | Pierpont | |
| 5,484,418 A | 1/1996 | Quiachon et al. | |
| 5,492,530 A | 2/1996 | Fischell et al. | |
| 5,496,294 A | 3/1996 | Hergenrother et al. | |
| 5,520,702 A | 5/1996 | Sauer et al. | |
| 5,527,322 A | 6/1996 | Klein et al. | |
| 5,542,937 A | 8/1996 | Chee et al. | |
| 5,549,633 A | 8/1996 | Evans et al. | |
| 5,558,635 A | 9/1996 | Cannon | |
| 5,573,520 A | 11/1996 | Schwartz et al. | |
| 5,584,803 A | 12/1996 | Stevens et al. | |
| 5,599,305 A | 2/1997 | Hermann et al. | |
| 5,599,326 A | 2/1997 | Carter | |
| 5,613,974 A | 3/1997 | Andreas et al. | |
| 5,628,754 A | 5/1997 | Shevlin et al. | |
| 5,643,289 A | 7/1997 | Sauer et al. | |
| 5,643,292 A | 7/1997 | Hart | |
| 5,649,959 A | 7/1997 | Hannam et al. | |
| 5,658,264 A | 8/1997 | Samson | |
| 5,667,499 A | 9/1997 | Welch et al. | |
| 5,669,881 A | 9/1997 | Dunshee | |
| 5,669,917 A | 9/1997 | Sauer et al. | |
| 5,674,231 A | 10/1997 | Green et al. | |
| 5,695,483 A | 12/1997 | Samson | |
| 5,702,373 A | 12/1997 | Samson | |
| 5,707,376 A | 1/1998 | Kavteladze et al. | |
| 5,720,757 A | 2/1998 | Hathaway et al. | |
| 5,730,734 A | 3/1998 | Adams et al. | |
| 5,749,849 A | 5/1998 | Engelson | |
| 5,749,858 A | 5/1998 | Cramer | |
| 5,766,183 A | 6/1998 | Sauer | |
| 5,769,821 A | 6/1998 | Abrahamson et al. | |
| 5,769,830 A | 6/1998 | Parker | |
| 5,779,719 A | 7/1998 | Klein et al. | |
| 5,782,800 A | 7/1998 | Yoon | |
| 5,792,152 A | 8/1998 | Klein et al. | |
| 5,795,341 A | 8/1998 | Samson | |
| 5,797,929 A | 8/1998 | Andreas et al. | |
| 5,810,846 A | 9/1998 | Virnich et al. | |
| 5,810,850 A | 9/1998 | Hathaway et al. | |
| 5,810,869 A | 9/1998 | Kaplan et al. | |
| 5,827,229 A | 10/1998 | Auth et al. | |
| 5,833,650 A | 11/1998 | Imran | |
| 5,836,926 A | 11/1998 | Peterson et al. | |
| 5,846,251 A | 12/1998 | Hart | |
| 5,846,253 A | 12/1998 | Buelna et al. | |
| 5,851,210 A | 12/1998 | Torossian | |
| 5,853,400 A | 12/1998 | Samson | |
| 5,855,585 A | 1/1999 | Kontos | |
| 5,860,990 A | 1/1999 | Nobles et al. | |

(56) References Cited

U.S. PATENT DOCUMENTS

| | | |
|---|---|---|
| 5,860,991 A | 1/1999 | Klein et al. |
| 5,876,367 A | 3/1999 | Kaganov et al. |
| 5,876,386 A | 3/1999 | Samson |
| 5,882,334 A | 3/1999 | Sepetka et al. |
| 5,895,399 A | 4/1999 | Barbut et al. |
| 5,910,154 A | 6/1999 | Tsugita et al. |
| 5,913,848 A | 6/1999 | Luther et al. |
| 5,916,193 A | 6/1999 | Stevens et al. |
| 5,916,208 A | 6/1999 | Luther et al. |
| 5,921,952 A | 7/1999 | Desmond, III et al. |
| 5,921,994 A | 7/1999 | Andreas et al. |
| 5,935,122 A | 8/1999 | Fourkas et al. |
| 5,938,645 A | 8/1999 | Gordon |
| 5,976,093 A | 11/1999 | Jang |
| 5,997,508 A | 12/1999 | Lunn et al. |
| 6,004,310 A | 12/1999 | Bardsley et al. |
| 6,004,341 A | 12/1999 | Zhu et al. |
| 6,022,340 A | 2/2000 | Sepetka et al. |
| 6,024,747 A | 2/2000 | Kontos |
| 6,030,369 A | 2/2000 | Engelson et al. |
| 6,030,395 A | 2/2000 | Nash et al. |
| 6,033,388 A | 3/2000 | Nordstrom et al. |
| 6,042,601 A | 3/2000 | Smith |
| 6,053,903 A | 4/2000 | Samson |
| 6,053,904 A | 4/2000 | Scribner et al. |
| 6,071,263 A | 6/2000 | Kirkman |
| 6,074,398 A | 6/2000 | Leschinsky |
| 6,090,072 A | 7/2000 | Kratoska et al. |
| 6,110,139 A | 8/2000 | Loubser |
| 6,110,185 A | 8/2000 | Barra et al. |
| 6,117,144 A | 9/2000 | Nobles et al. |
| 6,117,145 A | 9/2000 | Wood et al. |
| 6,132,440 A | 10/2000 | Hathaway et al. |
| 6,136,010 A | 10/2000 | Modesitt et al. |
| 6,139,524 A | 10/2000 | Killion |
| 6,146,370 A | 11/2000 | Barbut |
| 6,146,373 A | 11/2000 | Cragg et al. |
| 6,146,415 A | 11/2000 | Fitz |
| 6,152,912 A | 11/2000 | Jansen et al. |
| 6,159,230 A | 12/2000 | Samuels |
| 6,161,547 A | 12/2000 | Barbut |
| 6,165,199 A | 12/2000 | Barbut |
| 6,176,844 B1 | 1/2001 | Lee |
| 6,190,396 B1 | 2/2001 | Whitin et al. |
| 6,197,016 B1 | 3/2001 | Fourkas et al. |
| 6,197,042 B1 | 3/2001 | Ginn et al. |
| 6,206,868 B1 | 3/2001 | Parodi |
| 6,206,893 B1 | 3/2001 | Klein et al. |
| 6,210,370 B1 | 4/2001 | Chi-Sing et al. |
| 6,234,971 B1 | 5/2001 | Jang |
| 6,245,079 B1 | 6/2001 | Nobles et al. |
| 6,258,080 B1 | 7/2001 | Samson |
| 6,258,115 B1 | 7/2001 | Dubrul |
| 6,270,477 B1 | 8/2001 | Bagaoisan et al. |
| 6,277,140 B2 | 8/2001 | Ginn et al. |
| 6,287,319 B1 | 9/2001 | Aboul-Hosn et al. |
| 6,295,989 B1 | 10/2001 | Connors, III |
| 6,302,898 B1 | 10/2001 | Edwards et al. |
| 6,306,106 B1 | 10/2001 | Boyle |
| 6,306,163 B1 | 10/2001 | Fitz |
| 6,312,444 B1 | 11/2001 | Barbut |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,364,900 B1 | 4/2002 | Heuser |
| 6,368,316 B1 | 4/2002 | Jansen et al. |
| 6,368,334 B1 | 4/2002 | Sauer |
| 6,368,344 B1 | 4/2002 | Fitz |
| 6,379,325 B1 | 4/2002 | Benett et al. |
| 6,383,172 B1 | 5/2002 | Barbut |
| 6,391,048 B1 | 5/2002 | Ginn et al. |
| 6,413,235 B1 | 7/2002 | Parodi |
| 6,419,653 B2 | 7/2002 | Edwards et al. |
| 6,423,032 B2 * | 7/2002 | Parodi .......... A61B 17/12 604/103.07 |
| 6,423,086 B1 | 7/2002 | Barbut et al. |
| 6,428,549 B1 | 8/2002 | Kontos |
| 6,435,189 B1 | 8/2002 | Lewis et al. |
| 6,436,109 B1 | 8/2002 | Kontos |
| 6,454,741 B1 | 9/2002 | Muni et al. |
| 6,458,103 B1 | 10/2002 | Albert et al. |
| 6,458,151 B1 | 10/2002 | Saltiel |
| 6,461,364 B1 | 10/2002 | Ginn et al. |
| 6,464,664 B1 | 10/2002 | Jonkman et al. |
| 6,471,672 B1 | 10/2002 | Brown et al. |
| 6,482,172 B1 | 11/2002 | Thramann |
| 6,485,500 B1 | 11/2002 | Kokish et al. |
| 6,517,520 B2 | 2/2003 | Chang et al. |
| 6,517,553 B2 | 2/2003 | Klein et al. |
| 6,527,746 B1 * | 3/2003 | Oslund .......... A61F 2/013 604/160 |
| 6,533,800 B1 | 3/2003 | Barbut |
| 6,540,712 B1 | 4/2003 | Parodi et al. |
| 6,544,276 B1 | 4/2003 | Azizi |
| 6,551,268 B1 | 4/2003 | Kaganov et al. |
| 6,551,331 B2 | 4/2003 | Nobles et al. |
| 6,555,057 B1 | 4/2003 | Barbut et al. |
| 6,558,356 B2 | 5/2003 | Barbut |
| 6,558,399 B1 | 5/2003 | Isbell et al. |
| 6,562,049 B1 | 5/2003 | Norlander et al. |
| 6,562,052 B2 | 5/2003 | Nobles et al. |
| 6,569,182 B1 | 5/2003 | Balceta et al. |
| 6,582,390 B1 | 6/2003 | Sanderson |
| 6,582,396 B1 | 6/2003 | Parodi |
| 6,582,448 B1 | 6/2003 | Boyle et al. |
| 6,589,206 B1 | 7/2003 | Sharkawy et al. |
| 6,595,953 B1 | 7/2003 | Coppi et al. |
| 6,595,980 B1 | 7/2003 | Barbut |
| 6,596,003 B1 | 7/2003 | Realyvasquez, Jr. et al. |
| 6,605,074 B2 | 8/2003 | Zadno-Azizi et al. |
| 6,612,999 B2 | 9/2003 | Brennan et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,626,918 B1 | 9/2003 | Ginn et al. |
| 6,632,236 B2 | 10/2003 | Hogendijk |
| 6,632,238 B2 | 10/2003 | Ginn et al. |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,592 B1 | 11/2003 | Sauer et al. |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,652 B2 | 12/2003 | Daniel et al. |
| 6,669,721 B1 | 12/2003 | Bose et al. |
| 6,673,040 B1 | 1/2004 | Samson et al. |
| 6,682,505 B2 | 1/2004 | Bates et al. |
| 6,695,861 B1 | 2/2004 | Rosenberg et al. |
| 6,695,867 B2 | 2/2004 | Ginn et al. |
| 6,702,782 B2 | 3/2004 | Miller et al. |
| 6,711,436 B1 | 3/2004 | Duhaylongsod |
| 6,719,717 B1 | 4/2004 | Johnson et al. |
| 6,719,777 B2 | 4/2004 | Ginn et al. |
| 6,730,102 B1 | 5/2004 | Burdulis, Jr. et al. |
| 6,733,517 B1 | 5/2004 | Collins |
| 6,736,790 B2 | 5/2004 | Barbut et al. |
| 6,746,457 B2 | 6/2004 | Dana et al. |
| 6,749,621 B2 | 6/2004 | Pantages et al. |
| 6,749,627 B2 | 6/2004 | Thompson et al. |
| 6,755,847 B2 | 6/2004 | Eskuri |
| 6,758,854 B1 | 7/2004 | Butler et al. |
| 6,764,464 B2 | 7/2004 | McGuckin, Jr. et al. |
| 6,783,511 B2 | 8/2004 | Komtebedde et al. |
| 6,790,197 B2 | 9/2004 | Kosinski et al. |
| 6,827,730 B1 | 12/2004 | Leschinsky |
| 6,830,579 B2 | 12/2004 | Barbut |
| 6,837,881 B1 | 1/2005 | Barbut |
| 6,840,949 B2 | 1/2005 | Barbut |
| 6,847,234 B2 | 1/2005 | Choi |
| 6,849,068 B1 | 2/2005 | Bagaoisan et al. |
| 6,855,136 B2 | 2/2005 | Dorros et al. |

(56) References Cited

U.S. PATENT DOCUMENTS

| | | | |
|---|---|---|---|
| 6,875,231 B2 | 4/2005 | Anduiza et al. | |
| 6,878,140 B2 | 4/2005 | Barbut | |
| 6,884,235 B2 | 4/2005 | McGuckin, Jr. et al. | |
| 6,887,227 B1 | 5/2005 | Barbut | |
| 6,902,540 B2 | 6/2005 | Dorros et al. | |
| 6,905,490 B2 | 6/2005 | Parodi | |
| 6,905,505 B2 | 6/2005 | Nash et al. | |
| 6,908,474 B2 | 6/2005 | Hogendijk et al. | |
| 6,929,634 B2 | 8/2005 | Dorros et al. | |
| 6,932,824 B1 | 8/2005 | Roop et al. | |
| 6,936,060 B2* | 8/2005 | Hogendijk | A61B 17/12 604/5.01 |
| 6,942,674 B2 | 9/2005 | Belef et al. | |
| 6,958,059 B2 | 10/2005 | Zadno-Azizi | |
| 6,964,668 B2 | 11/2005 | Modesitt et al. | |
| 6,972,030 B2 | 12/2005 | Lee et al. | |
| 6,979,346 B1 | 12/2005 | Hossainy et al. | |
| 7,001,398 B2 | 2/2006 | Carley et al. | |
| 7,001,400 B1 | 2/2006 | Modesitt et al. | |
| 7,004,924 B1 | 2/2006 | Brugger et al. | |
| 7,004,931 B2 | 2/2006 | Hogendijk | |
| 7,022,100 B1 | 4/2006 | Aboul-Hosn et al. | |
| 7,029,480 B2 | 4/2006 | Klein et al. | |
| 7,029,487 B2 | 4/2006 | Greene, Jr. et al. | |
| 7,029,488 B2 | 4/2006 | Schonholz et al. | |
| 7,033,344 B2 | 4/2006 | Imran | |
| 7,048,747 B2 | 5/2006 | Arcia et al. | |
| 7,048,758 B2 | 5/2006 | Boyle et al. | |
| 7,063,714 B2 | 6/2006 | Dorros et al. | |
| 7,083,594 B2 | 8/2006 | Coppi | |
| 7,090,686 B2 | 8/2006 | Nobles et al. | |
| 7,094,246 B2 | 8/2006 | Anderson et al. | |
| 7,104,979 B2 | 9/2006 | Jansen et al. | |
| 7,108,677 B2 | 9/2006 | Courtney et al. | |
| 7,144,386 B2 | 12/2006 | Korkor et al. | |
| 7,144,411 B2 | 12/2006 | Ginn et al. | |
| 7,150,712 B2 | 12/2006 | Buehlmann et al. | |
| 7,152,605 B2 | 12/2006 | Khairkhahan et al. | |
| 7,166,088 B2 | 1/2007 | Heuser | |
| 7,172,621 B2 | 2/2007 | Theron | |
| 7,208,008 B2 | 4/2007 | Clarke | |
| 7,223,253 B2 | 5/2007 | Hogendijk | |
| 7,232,452 B2 | 6/2007 | Adams et al. | |
| 7,232,453 B2 | 6/2007 | Shimon | |
| 7,250,042 B2 | 7/2007 | Kataishi et al. | |
| 7,306,585 B2 | 12/2007 | Ross | |
| 7,309,334 B2 | 12/2007 | von Hoffmann | |
| 7,335,182 B1 | 2/2008 | Hilaire | |
| 7,367,982 B2 | 5/2008 | Nash et al. | |
| 7,374,560 B2 | 5/2008 | Ressemann et al. | |
| 7,374,561 B2 | 5/2008 | Barbut | |
| 7,390,328 B2 | 6/2008 | Modesitt | |
| 7,396,359 B1 | 7/2008 | Derowe et al. | |
| 7,402,151 B2 | 7/2008 | Rosenman et al. | |
| 7,422,579 B2 | 9/2008 | Wahr et al. | |
| 7,458,980 B2 | 12/2008 | Barbut | |
| 7,524,303 B1 | 4/2009 | Don Michael et al. | |
| 7,534,250 B2 | 5/2009 | Schaeffer et al. | |
| 7,578,839 B2 | 8/2009 | Serino et al. | |
| 7,604,612 B2 | 10/2009 | Ressemann et al. | |
| 7,731,683 B2 | 6/2010 | Jang et al. | |
| 7,766,049 B2 | 8/2010 | Miller et al. | |
| 7,766,820 B2 | 8/2010 | Core | |
| 7,815,626 B1 | 10/2010 | McFadden et al. | |
| 7,857,828 B2 | 12/2010 | Jabba et al. | |
| 7,867,216 B2 | 1/2011 | Wahr et al. | |
| 7,867,249 B2 | 1/2011 | Palermo et al. | |
| 7,905,856 B2 | 3/2011 | McGuckin, Jr. et al. | |
| 7,905,877 B1 | 3/2011 | Jimenez et al. | |
| 7,905,900 B2 | 3/2011 | Palermo et al. | |
| 7,909,812 B2 | 3/2011 | Jansen et al. | |
| 7,927,309 B2 | 4/2011 | Palm | |
| 7,972,308 B2 | 7/2011 | Putz | |
| 8,029,533 B2 | 10/2011 | Bagaoisan et al. | |
| 8,066,757 B2 | 11/2011 | Ferrera et al. | |
| 8,083,788 B2 | 12/2011 | Acosta et al. | |
| RE43,300 E | 4/2012 | Saadat et al. | |
| 8,152,782 B2 | 4/2012 | Jang et al. | |
| 8,157,760 B2* | 4/2012 | Criado | A61M 25/10 604/9 |
| 8,181,324 B2 | 5/2012 | McFadden et al. | |
| 8,202,293 B2 | 6/2012 | Ellingwood et al. | |
| 8,221,348 B2 | 7/2012 | Hackett et al. | |
| 8,231,600 B2 | 7/2012 | von Hoffmann | |
| 8,262,622 B2 | 9/2012 | Gonzales et al. | |
| 8,313,497 B2 | 11/2012 | Walberg et al. | |
| 8,784,355 B2 | 7/2014 | Criado et al. | |
| 8,858,490 B2 | 10/2014 | Chou et al. | |
| 9,011,364 B2 | 4/2015 | Criado et al. | |
| 9,789,242 B2* | 10/2017 | Criado | A61M 25/10 |
| 9,833,555 B2* | 12/2017 | Criado | A61M 25/10 |
| 10,085,864 B2 | 10/2018 | Chou et al. | |
| 10,286,139 B2 | 5/2019 | Criado et al. | |
| 2001/0034509 A1 | 10/2001 | Cragg et al. | |
| 2001/0044591 A1 | 11/2001 | Stevens et al. | |
| 2001/0044598 A1 | 11/2001 | Parodi | |
| 2001/0044634 A1 | 11/2001 | Don Michael et al. | |
| 2001/0044638 A1 | 11/2001 | Levinson et al. | |
| 2001/0049486 A1 | 12/2001 | Evans et al. | |
| 2001/0049517 A1 | 12/2001 | Zadno-Azizi et al. | |
| 2002/0052620 A1 | 5/2002 | Barbut | |
| 2002/0052640 A1 | 5/2002 | Bigus et al. | |
| 2002/0058910 A1 | 5/2002 | Hermann et al. | |
| 2002/0068899 A1 | 6/2002 | McGuckin et al. | |
| 2002/0077600 A1 | 6/2002 | Sirimanne | |
| 2002/0087119 A1 | 7/2002 | Parodi | |
| 2002/0103459 A1 | 8/2002 | Sparks et al. | |
| 2002/0128679 A1 | 9/2002 | Turovskiy et al. | |
| 2002/0151866 A1 | 10/2002 | Lundkvist et al. | |
| 2002/0156455 A1 | 10/2002 | Barbut | |
| 2002/0165598 A1 | 11/2002 | Wahr et al. | |
| 2002/0173815 A1 | 11/2002 | Hogendijk et al. | |
| 2003/0004543 A1 | 1/2003 | Gleeson et al. | |
| 2003/0032936 A1 | 2/2003 | Lederman | |
| 2003/0040762 A1 | 2/2003 | Dorros et al. | |
| 2003/0050600 A1 | 3/2003 | Ressemann et al. | |
| 2003/0065356 A1 | 4/2003 | Tsugita et al. | |
| 2003/0069468 A1 | 4/2003 | Bolling et al. | |
| 2003/0135206 A1 | 7/2003 | Edwards et al. | |
| 2003/0163086 A1 | 8/2003 | Denyer et al. | |
| 2003/0186203 A1 | 10/2003 | Aboud | |
| 2003/0212304 A1 | 11/2003 | Lattouf | |
| 2003/0233065 A1 | 12/2003 | Steward et al. | |
| 2004/0044329 A1 | 3/2004 | Trudell | |
| 2004/0064179 A1* | 4/2004 | Linder | A61F 2/013 623/1.11 |
| 2004/0116946 A1 | 6/2004 | Goldsteen et al. | |
| 2004/0122360 A1 | 6/2004 | Waldhauser et al. | |
| 2004/0127913 A1 | 7/2004 | Voss | |
| 2004/0138562 A1 | 7/2004 | Makower et al. | |
| 2004/0153123 A1 | 8/2004 | Palermo et al. | |
| 2004/0204675 A1 | 10/2004 | Seward et al. | |
| 2004/0210251 A1 | 10/2004 | Kontos | |
| 2004/0215181 A1 | 10/2004 | Christopherson et al. | |
| 2004/0215312 A1 | 10/2004 | Andreas | |
| 2004/0249435 A1 | 12/2004 | Andreas et al. | |
| 2004/0260333 A1 | 12/2004 | Dubrul et al. | |
| 2005/0010238 A1 | 1/2005 | Potter et al. | |
| 2005/0049671 A1 | 3/2005 | Wang et al. | |
| 2005/0096726 A1 | 5/2005 | Sequin et al. | |
| 2005/0124973 A1 | 6/2005 | Dorros et al. | |
| 2005/0131453 A1 | 6/2005 | Parodi | |
| 2005/0149065 A1 | 7/2005 | Modesitt | |
| 2005/0154344 A1 | 7/2005 | Chang | |
| 2005/0154349 A1 | 7/2005 | Renz et al. | |
| 2005/0228402 A1 | 10/2005 | Hofmann | |
| 2005/0228432 A1 | 10/2005 | Hogendijk et al. | |
| 2005/0251162 A1 | 11/2005 | Rothe et al. | |
| 2005/0267323 A1 | 12/2005 | Dorros et al. | |
| 2005/0273051 A1 | 12/2005 | Coppi | |
| 2006/0015171 A1 | 1/2006 | Armstrong | |
| 2006/0020270 A1 | 1/2006 | Jabba et al. | |
| 2006/0041232 A1 | 2/2006 | Stearns et al. | |
| 2006/0106338 A1 | 5/2006 | Chang | |

(56) References Cited

U.S. PATENT DOCUMENTS

| | | |
|---|---|---|
| 2006/0111741 A1 | 5/2006 | Nardella |
| 2006/0129125 A1 | 6/2006 | Copa et al. |
| 2006/0149350 A1 | 7/2006 | Patel et al. |
| 2006/0167437 A1 | 7/2006 | Valencia |
| 2006/0167476 A1 | 7/2006 | Burdulis et al. |
| 2006/0200191 A1 | 9/2006 | Zadno-Azizi |
| 2006/0282088 A1 | 12/2006 | Ryan |
| 2006/0287673 A1 | 12/2006 | Brett et al. |
| 2007/0010787 A1 | 1/2007 | Hackett et al. |
| 2007/0078430 A1 | 4/2007 | Adams |
| 2007/0123925 A1 | 5/2007 | Benjamin et al. |
| 2007/0123926 A1 | 5/2007 | Sater et al. |
| 2007/0198049 A1 | 8/2007 | Barbut |
| 2007/0249997 A1 | 10/2007 | Goodson et al. |
| 2007/0270888 A1 | 11/2007 | Barrientos |
| 2008/0004636 A1 | 1/2008 | Walberg et al. |
| 2008/0045979 A1 | 2/2008 | Ma |
| 2008/0051676 A1 | 2/2008 | Melsheimer |
| 2008/0058839 A1 | 3/2008 | Nobles et al. |
| 2008/0086164 A1 | 4/2008 | Rowe |
| 2008/0097479 A1 | 4/2008 | Boehlke et al. |
| 2008/0140010 A1 | 6/2008 | Kennedy et al. |
| 2008/0188890 A1 | 8/2008 | Weitzner et al. |
| 2008/0200946 A1 | 8/2008 | Braun et al. |
| 2008/0208329 A1 | 8/2008 | Bishop et al. |
| 2008/0221614 A1 | 9/2008 | Mas |
| 2008/0287967 A1 | 11/2008 | Andreas et al. |
| 2008/0312666 A1 | 12/2008 | Ellingwood et al. |
| 2009/0005738 A1 | 1/2009 | Franer |
| 2009/0018455 A1 | 1/2009 | Chang |
| 2009/0024072 A1 | 1/2009 | Criado et al. |
| 2009/0048654 A1 | 2/2009 | Chmura et al. |
| 2009/0076456 A1 | 3/2009 | Armstrong et al. |
| 2009/0143789 A1 | 6/2009 | Houser |
| 2009/0157105 A1 | 6/2009 | Zung et al. |
| 2009/0163864 A1 | 6/2009 | Breznock et al. |
| 2009/0198172 A1 | 8/2009 | Garrison et al. |
| 2009/0254166 A1 | 10/2009 | Chou et al. |
| 2010/0042118 A1 | 2/2010 | Garrison et al. |
| 2010/0114002 A1 | 5/2010 | O'Mahony et al. |
| 2010/0185216 A1 | 7/2010 | Garrison et al. |
| 2010/0204684 A1 | 8/2010 | Garrison et al. |
| 2010/0217276 A1 | 8/2010 | Garrison et al. |
| 2010/0228269 A1 | 9/2010 | Garrison et al. |
| 2010/0280431 A1 | 11/2010 | Criado et al. |
| 2011/0034986 A1 | 2/2011 | Chou et al. |
| 2011/0082408 A1 | 4/2011 | Chang |
| 2011/0087147 A1 | 4/2011 | Garrison et al. |
| 2011/0152625 A1 | 6/2011 | Smith |
| 2011/0166496 A1 | 7/2011 | Criado et al. |
| 2011/0166497 A1 | 7/2011 | Criado et al. |
| 2011/0213459 A1 | 9/2011 | Garrison et al. |
| 2011/0270182 A1 | 11/2011 | Breznock et al. |
| 2012/0083661 A1 | 4/2012 | Rockrohr |
| 2013/0035628 A1 | 2/2013 | Garrison et al. |
| 2013/0172661 A1 | 7/2013 | Farnan et al. |
| 2013/0172852 A1 | 7/2013 | Chang |
| 2013/0197621 A1 | 8/2013 | Ryan et al. |
| 2013/0281788 A1 | 10/2013 | Garrison |
| 2013/0331655 A1 | 12/2013 | Kasprzak et al. |
| 2014/0031682 A1 | 1/2014 | Renati et al. |
| 2014/0031925 A1 | 1/2014 | Garrison et al. |
| 2014/0046346 A1 | 2/2014 | Hentges et al. |
| 2014/0058414 A1 | 2/2014 | Garrison et al. |
| 2014/0135661 A1 | 5/2014 | Garrison et al. |
| 2014/0296769 A1 | 10/2014 | Hyde et al. |
| 2014/0296868 A1 | 10/2014 | Garrison et al. |
| 2014/0371653 A1 | 12/2014 | Criado et al. |
| 2015/0025616 A1 | 1/2015 | Chang |
| 2015/0080942 A1 | 3/2015 | Garrison et al. |
| 2015/0150562 A1 | 6/2015 | Chang |
| 2015/0173782 A1 | 6/2015 | Garrison et al. |
| 2015/0327843 A1 | 11/2015 | Garrison |
| 2016/0128688 A1 | 5/2016 | Garrison et al. |
| 2016/0158044 A1 | 6/2016 | Chou et al. |
| 2016/0166804 A1 | 6/2016 | Garrison et al. |
| 2016/0242764 A1 | 8/2016 | Garrison et al. |
| 2016/0271315 A1 | 9/2016 | Chang |
| 2016/0279379 A1 | 9/2016 | Chang |
| 2016/0296690 A1 | 10/2016 | Kume et al. |
| 2017/0361072 A1 | 12/2017 | Chou et al. |
| 2017/0368296 A1 | 12/2017 | Chang |

FOREIGN PATENT DOCUMENTS

| | | |
|---|---|---|
| EP | 1649829 A1 | 4/2006 |
| EP | 2497520 A1 | 9/2012 |
| JP | S59-161808 U | 10/1984 |
| JP | 02-237574 | 9/1990 |
| JP | H07-265412 A | 10/1995 |
| JP | H08-071161 A | 3/1996 |
| JP | 10-43192 A | 2/1998 |
| JP | 10-052490 A | 2/1998 |
| JP | H10-033666 A | 2/1998 |
| JP | 11-42233 A | 2/1999 |
| JP | 2001-517472 A | 10/2001 |
| JP | 2001-523492 A | 11/2001 |
| JP | 2002-518086 A | 6/2002 |
| JP | 2002-522149 A | 7/2002 |
| JP | 2002-543914 A | 12/2002 |
| JP | 2003-516178 A | 5/2003 |
| JP | 2003-521286 A | 7/2003 |
| JP | 2003-521299 A | 7/2003 |
| JP | 2003-310625 A | 11/2003 |
| JP | 2005-536284 | 12/2005 |
| JP | 2006-500095 A | 1/2006 |
| JP | 2007-500577 A | 1/2007 |
| JP | 2007-244902 A | 9/2007 |
| JP | 2007-301326 A | 11/2007 |
| WO | WO-95/05209 A1 | 2/1995 |
| WO | WO-98/38930 A1 | 9/1998 |
| WO | WO-99/15085 A1 | 4/1999 |
| WO | WO-99/25419 A | 5/1999 |
| WO | WO-99/040945 A2 | 8/1999 |
| WO | WO-99/45835 A2 | 9/1999 |
| WO | WO-99/65420 A1 | 12/1999 |
| WO | WO-00/09028 A1 | 2/2000 |
| WO | WO-00/32266 A1 | 6/2000 |
| WO | WO-00/56223 A1 | 9/2000 |
| WO | WO-00/69350 A1 | 11/2000 |
| WO | WO-00/76390 A2 | 12/2000 |
| WO | WO-01/34061 A1 | 5/2001 |
| WO | WO-01/54588 A1 | 8/2001 |
| WO | WO-02/32495 A1 | 4/2002 |
| WO | WO-02/096295 A1 | 12/2002 |
| WO | WO-03/071955 A2 | 9/2003 |
| WO | WO-03/090628 A1 | 11/2003 |
| WO | WO-03/090831 A2 | 11/2003 |
| WO | WO-2004/006803 A1 | 1/2004 |
| WO | WO-2004/017865 A1 | 3/2004 |
| WO | WO-2004/026144 A1 | 4/2004 |
| WO | WO-2004/060169 A2 | 7/2004 |
| WO | WO-2004/110303 A2 | 12/2004 |
| WO | WO-2005/051206 A1 | 6/2005 |
| WO | WO-2006/128017 A2 | 11/2006 |
| WO | WO-2007/136946 A2 | 11/2007 |
| WO | WO-2009/012473 A3 | 1/2009 |
| WO | WO-2009/099764 A1 | 8/2009 |
| WO | WO-2009/100210 A1 | 8/2009 |
| WO | WO-2010/019719 A2 | 2/2010 |
| WO | WO-2014/025930 A1 | 2/2014 |
| WO | WO-2014/078301 A1 | 5/2014 |
| WO | WO-2014/160613 A1 | 10/2014 |
| WO | WO-2014/160887 A2 | 10/2014 |
| WO | WO-2014/204860 A1 | 12/2014 |
| WO | WO-2015/175537 A1 | 11/2015 |
| WO | WO-2016/018781 A1 | 2/2016 |
| WO | WO-2016/036660 A1 | 3/2016 |
| WO | WO-2016/137875 A1 | 9/2016 |

(56) References Cited

FOREIGN PATENT DOCUMENTS

| WO | WO-2016/164606 A1 | 10/2016 |
|---|---|---|
| WO | WO-2016/176409 A1 | 11/2016 |

OTHER PUBLICATIONS

Alexandrescu et al. (2006) "Filter-protected carotid stenting via a minimal cervical access with transitory aspirated reversed flow during initial passage of the target lesion" J. Endovasc. Ther. 13(2):196-204.

Alvarez et al. (2008). "Transcervical carotid stenting with flow reversal is safe in octogenarians: A preliminary safety study" J. Vasc. Surg. 47:96-100.

Bates M.D., et al. "Reversal of the Direction of Internal Carotid Artery Blood Flow by Occlusion of the Common and External Carotid Arteries in a Swine Model" Catherization and Cardiovascular Intervention 60:270-275 (2003).

Bates, M.D., et al. "Internal Carotid Artery Flow Arrest/Reversal Cerebral Protection Techniques" The West Virginal Medical Journal, Mar./Apr. 2004, vol. 99: 60-63.

Bergeron et al. (1999). "Percutaneous stenting of the internal carotid artery: the European Cast I Study" J. Endovasc. Surg. 6:15-159.

Bergeron et al. (2008) MEET Presentation, Cannes, French Riviera "Why I do not use routine femoral access for CAS." 12 pages.

Bergeron P. et al. (1996) "Recurrent Carotid Disease: Will Stents be an alternative to surgery?" J Endovasc Surg; 3: 76-79.

Bettmann, M. et al, "Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association". Circulation Journal of the American Heart Association. 1998. 97:121-123. Retrieved Feb. 16, 2012.

Bhatt, D. L., R. E. Raymond, et al. (2002). "Successful "preclosure" of 7Fr and 8Fr femoral arteriotomies with a 6Fr suture-based device (the Multicenter Interventional Closer Registry)." Am J Cardiol 89(6): 777-9.

Blanc, R., C. Mounayer, et al. (2002). "Hemostatic closure device after carotid puncture for stent and coil placement in an intracranial aneurysm: technical note." AJNR Am J Neuroradiol 23(6): 978-81.

Blanc, R., M. Piotin, et al. (2006). "Direct cervical arterial access for intracranial endovascular treatment." Neuroradiology 48(12): 925-9.

Chang, M.D., et al, "A new approach to carotid angioplasty and stenting with transcervical occlusion and protective shunting: Why it may be a better carotid artery intervention" (J Vasc Surg 2004; 39:994-1002.).

Chang, M.D., "Carotid Angioplasty and Stenting Using Transcervical Occlusion and Protective Shunting Via a Mini Incision in the Neck: A New Technique for Difficult Femoral Access or Filter Placement May Be the Better Carotid Artery Intervention" 30th Global: Vascular and Endovascular Issues, Techniques and Horizons Symposium, New York, NY, Nov. 20-23, 2003; XXVII 6.1-XXVII 6.2.

Coppi et al. (2005). "PRIAMUS Proximal flow blockage cerebral protection during carotid stenting: Results from a multicenter Italian regiStry" J. Cardiovasc. Surg. 46:219-227.

Criado et al. (1997) "Evolving indications for and early results of carotid artery stenting" Am. J. Surg.; 174:111-114.

Criado et al. (2004). "Transcervical carotid artery angioplasty and stenting with carotid flow reversal: Surgical technique" J. Vasc. Surg. 18:257-261.

Criado et al. (2004). "Transcervical carotid stenting with internal carotid artery flow reversal: Feasibility and preliminary results" J. Vasc. Surg. 40:476-483.

Criado, E., J. Fontcuberta, et al. (2007). "Transcervical carotid stenting with carotid artery flow reversal: 3-year follow-up of 103 stents." J Vasc Surg 46(5): 864-9.

Criado, F.J., et al., Access strategies for carotid artery intervention. J Invasive Cardiol, 2000. 12(1): p. 61-68.

Criado, M.D., et al. (2004) "Carotid angioplasty with internal carotid artery flow reversal is well tolerated in the awake patient" Journal of Vascular Surgery, 40(1):92-7.

Diederich et al. (2004) "First Clinical experiences with an endovascular clamping system for neuroprotection during carotid stenting" Eur. J. Vasc. Endovasc. Surg. 28:629-633.

Diethrich et al., (1996). "Percutaneous techniques for endoluminal carotid interventions" J. Endovasc. Surg. 3:182-202.

Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.

Feldtman, R. W., C. J. Buckley, et al. (2006). "How I do it: cervical access for carotid artery stenting." Am J Surg 192(6): 779-81.

Goldstein (2007) "Acute Ischemic Stroke Treatment in 2007" Circ 116:1504-1514.

Gray et al. (2007) "The CAPTURE registry: Results of carotid stenting with embolic protection in the post approval setting" Cath. Cardovasc. Interven. 69:341-348.

Henry et al. (1999) "Carotid stenting with cerebral protection: First clinical experience using the PercuSurge GuardWire System" J. Endovasc. Surg. 6:321-331.

Hoffer et al. "Percutaneous Arterial Closure Devices" J. Vasc. Interv. Radiol. 14:865-885 (2003).

Howell, M., K. Doughtery, et al. (2002). "Percutaneous repair of abdominal aortic aneurysms using the AneuRx stent graft and the percutaneous vascular surgery device." Catheter Cardiovasc Intery 55(3): 281-7.

Lin et al. (2005) "Protected carotid artery stenting and angioplasty via transfemoral versus transcervical approaches" Vasc. Endovasc. Surg. 39(6):499-503.

Lo et al. (2005) "Advantages and indications of transcervical carotid artery stenting with carotid flow reversal" J. Cardovasc. Surg (Torino). 46(3):229-239.

Luebke, T et al. (2007) "Meta-analysis of randomized trials comparing carotid endarterectomy and endovascular treatment" Eur. J. Vasc. Endovasc. Surg. 34:470-479.

Macdonald, S. (2006) "Is there any evidence that cerebral protection is beneficial?" J. Cardiovasc. Surg. 47:127-36.

Mas et al. (2006) "Endarterectomy versus stenting in patients with symptomatic severe carotid stenosis" NEJM 355:1660-71.

Massiere, B., A. von Ristow, et al. (2009). "Closure of Carotid Artery Puncture Site With a Percutaneous Device." Ann Vasc Surg. 23(2): 256 e5-7.

Matas et al. (2007). "Transcervical carotid stenting with flow reversal protection: Experience in high-risk patients" J. Vasc. Surg. 46:49-54.

Momapresn (AET) 2002 Biamino, G; MO.MA as a distal protective device, University of Leipzig—Heart Center Department of Clinical and Interventional; Angiology Leipzig, Germany; 2002. 37 pages.

Ohki, M.D., et al., "Efficacy of a proximal occlusion catheter with reversal of flow in the prevention of embolic events during carotid artery stenting: An experimental analysis" (J Vasc Surg 2001; 33:504-9).

Ouriel, K., R. K. Greenberg, et al. (2001). "Hemodynamic conditions at the carotid bifurcation during protective common carotid occlusion." J Vasc Surg 34(4): 577-80.

Parodi (2005). "Is flow reversal the best method of protection during carotid stenting?" J Endovasc. Ther. 12:166-170.

Parodi et al. (2000). "Initial evaluation of carotid angioplasty and stenting with three different cerebral protection devices" J. Vasc. Surg. 32:1127-1136.

Parodi, J. C., L. M. Ferreira, et al. (2005). "Cerebral protection during carotid stenting using flow reversal." J Vasc Surg 41(3): 416-22.

Perez-Arjona, E. A., Z. DelProsto, et al. (2004). "Direct percutaneous carotid artery stenting with distal protection: technical case report." Neurol Res 26(3): 338-41.

Pipinos et al. (2005). "Transcervical approach with protective flow reversal for carotid angioplasty and stenting" J. Endovasc. Ther. 12:446-453.

(56) References Cited

OTHER PUBLICATIONS

Pipinos et al. (2006). "Transcervical carotid stenting with flow reversal for neuroprotection: Technique, results, advantages, and limitations" 14(5):243-255.
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results from a prospective multicenter registry" J. Endovasc. Ther. 12:156-165.
Ribo et al. (2006). "Transcranial doppler monitoring of transcervical carotid stenting with flow reversal protection: a novel carotid revascularization technique" 27:2846-2849 (originally published online Sep. 28, 2006).
Stecker t al., "Stent Placement in Common Carotid and Internal Carotid Artery Stenoses with Use of an Open Transcervical Approach in a Patient with Previous Endarterectomy"; J. Vasc Intery Radiol 2002; 13:413-417.
Stejskal, et al., "Experience of 500 Cases of Neurophysiological Monitoring in Carotid Endarterectomy", Acta Neurochir, 2007, 149:681-689.
Theron, et al. "New Triple Coaxial Catheter System for Carotid Angioplasty with Cerebral Protection" AJNR 11:869-874, Sep./Oct. 1990 0195-6108/90/1106-0869 @ American Society of Neurology.
U.S. Appl. No. 12/645,179, filed Dec. 22, 2009, U.S. Pat. No. 2010-0217276.
U.S. Appl. No. 14/078,149, filed Nov. 12, 2013, U.S. Pat. No. 2014-0135661.
U.S. Appl. No. 15/093,406, filed Apr. 7, 2016, U.S. Pat. No. 2016-0296690.
U.S. Appl. No. 15/399,638, filed Jan. 5, 2016, U.S. Pat. No. 2017-0209260.
U.S. Appl. No. 15/489,055, filed Apr. 17, 2017, U.S. Pat. No. 2017-0312491.
U.S. Appl. No. 15/613,891, filed Jun. 5, 2017, U.S. Pat. No. 2017-0361072.
U.S. Appl. No. 15/613,921, filed Jun. 5, 2017, U.S. Pat. No. 2017-0368296.
U.S. Appl. No. 14/227,585, filed Mar. 27, 2014, U.S. Pat. No. 2014-0296769.
U.S. Appl. No. 14/935,252, filed Nov. 6, 2015, U.S. Pat. No. 2016-0128688.
U.S. Appl. No. 15/049,637, filed Feb. 22, 2016, U.S. Pat. No. 2016-0242764.
U.S. Appl. No. 15/141,060, filed Apr. 28, 2016, U.S. Pat. No. 2016-0317288.
U.S. Appl. No. 15/399,638, filed Jan. 5, 2017, U.S. Pat. No. 2017-0209260.
U.S. Appl. No. 15/628,190, filed Jun. 20, 2017, U.S. Pat. No. 2018-0008294.
U.S. Appl. No. 15/641,966, filed Jul. 5, 2017, U.S. Pat. No. 2017-0296798.
U.S. Appl. No. 15/728,747, filed Oct. 10, 2017, U.S. Pat. No. 2018-0154063.
U.S. Appl. No. 15/728,915, filed Oct. 10, 2017, U.S. Pat. No. 2018-0185614.
U.S. Appl. No. 15/901,502, filed Feb. 21, 2018, U.S. Pat. No. 2018-0235789.
U.S. Appl. No. 16/056,208, filed Aug. 6, 2018, U.S. Pat. No. 2019-0175885.
U.S. Appl. No. 16/171,784, filed Oct. 26, 2018, U.S. Pat. No. 2019-0125512.
U.S. Appl. No. 16/177,716, filed Nov. 1, 2018, U.S. Pat. No. 2019-0150916.
U.S. Appl. No. 16/377,663, filed Apr. 8, 2019, U.S. Pat. No. 2019-0231962.
PCT/US18/18943, filed Feb. 21, 2018, WO 2018/156574.
PCT/US18/40264, filed Jun. 29, 2018, WO 2019/010077.
PCT/US18/57789, filed Oct. 26, 2018, WO 2019/089385.

* cited by examiner

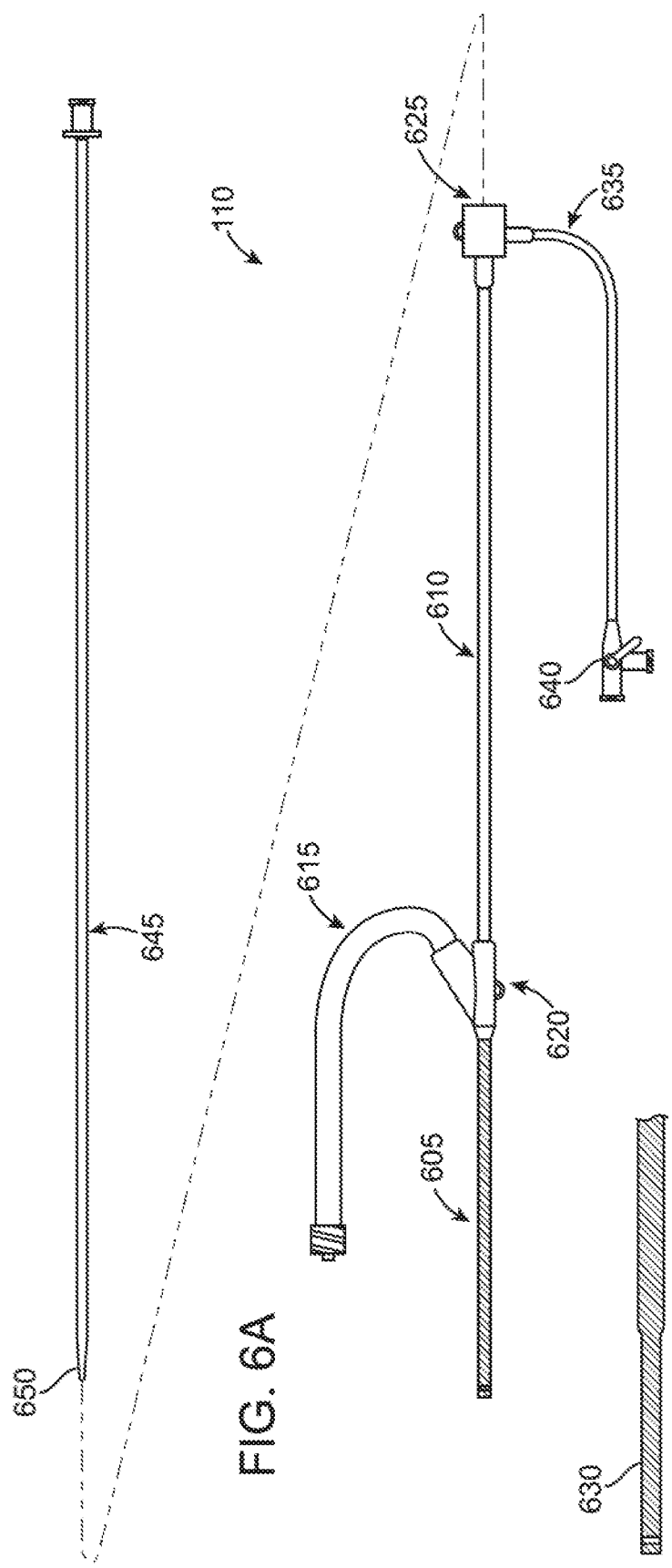

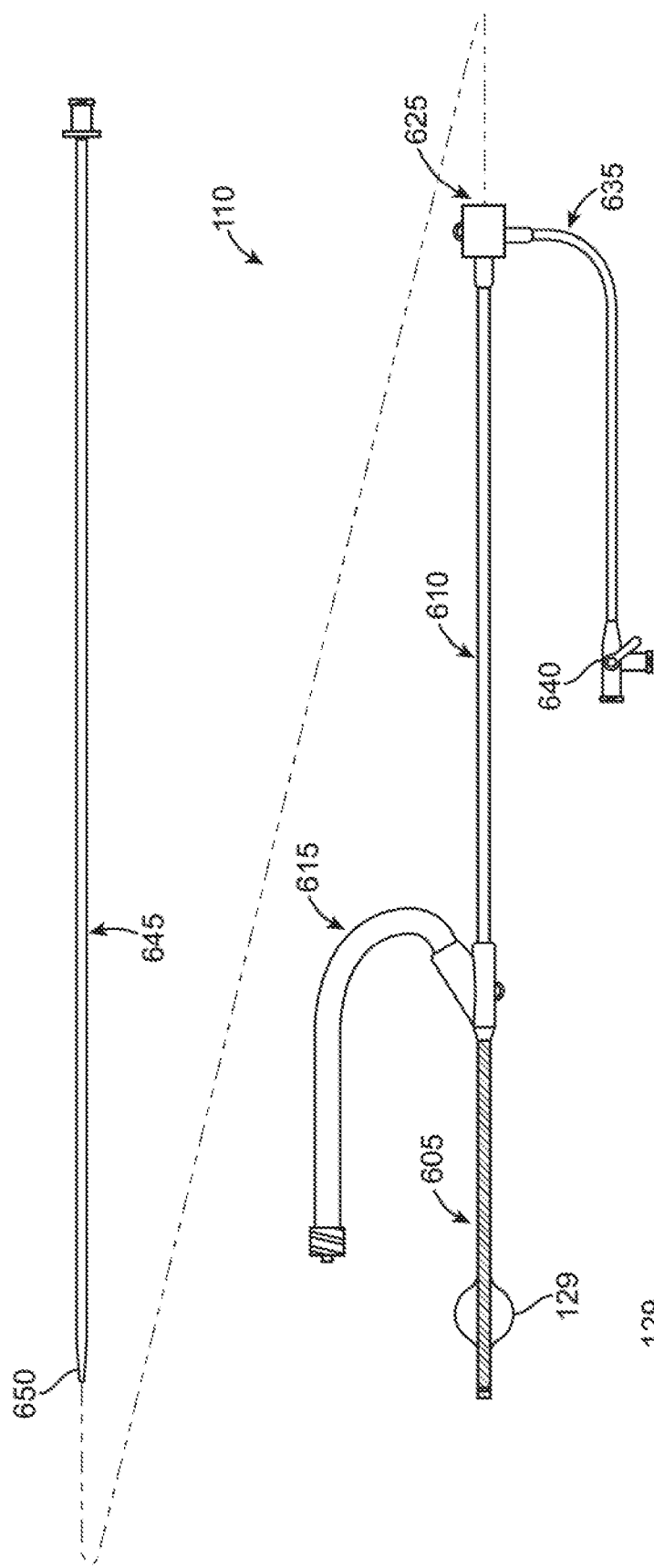
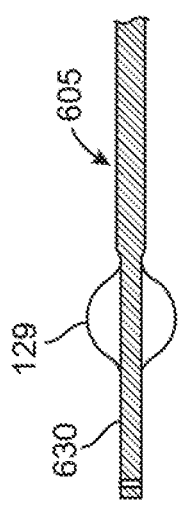
FIG. 8A
FIG. 8B

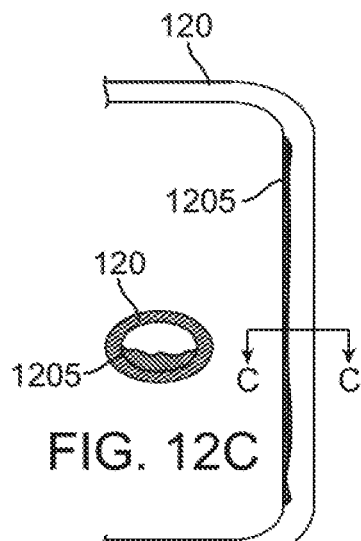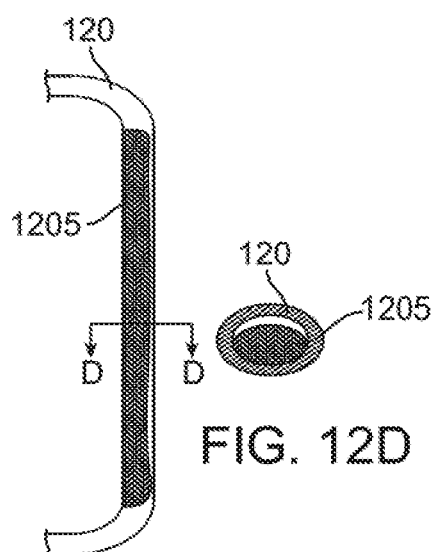
FIG. 12A    FIG. 12B
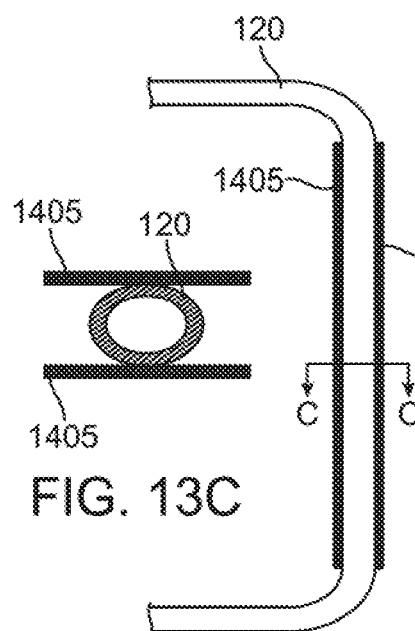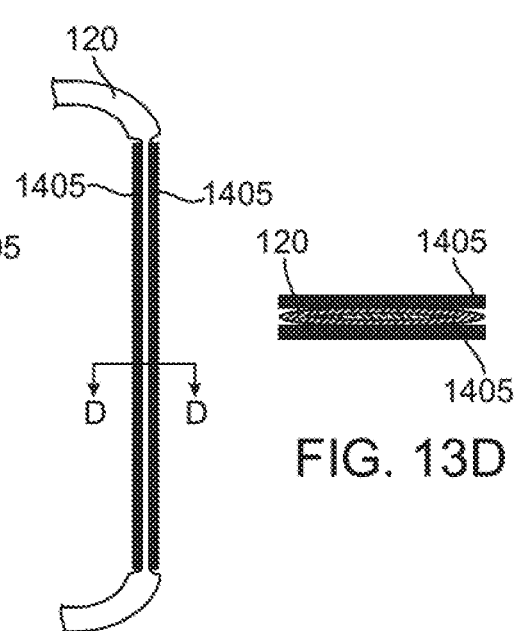
FIG. 13A    FIG. 13B

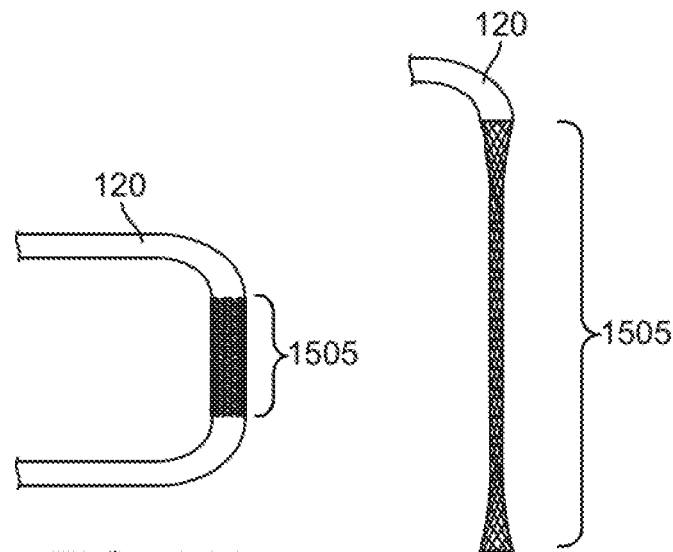
FIG. 14A
FIG. 14B
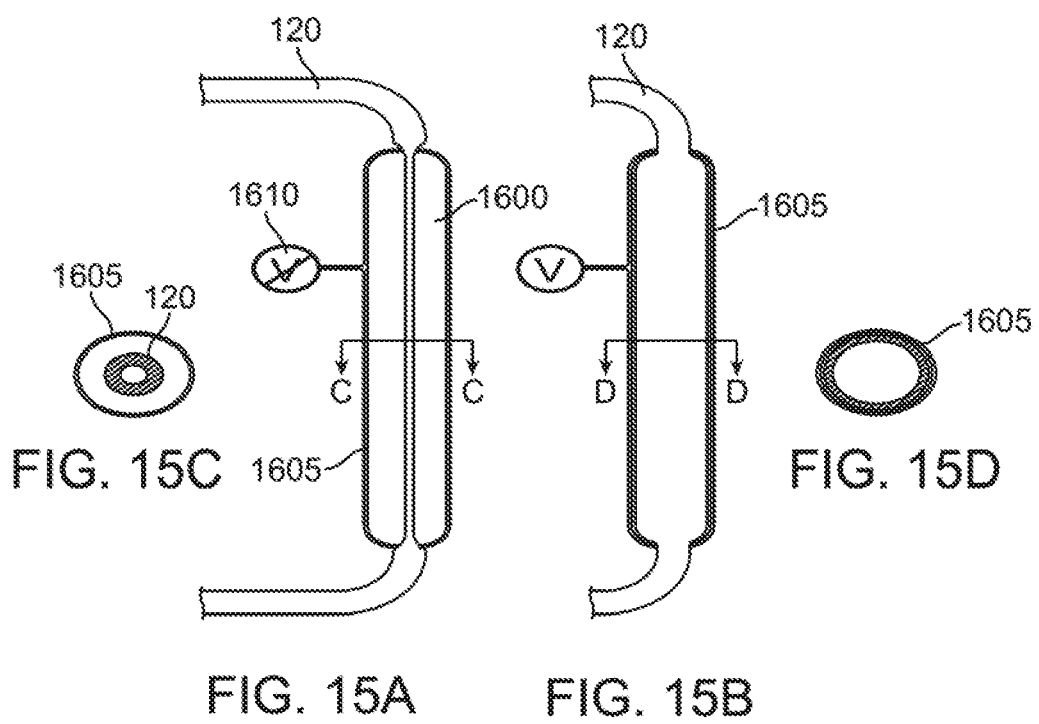
FIG. 15C
FIG. 15A
FIG. 15B
FIG. 15D

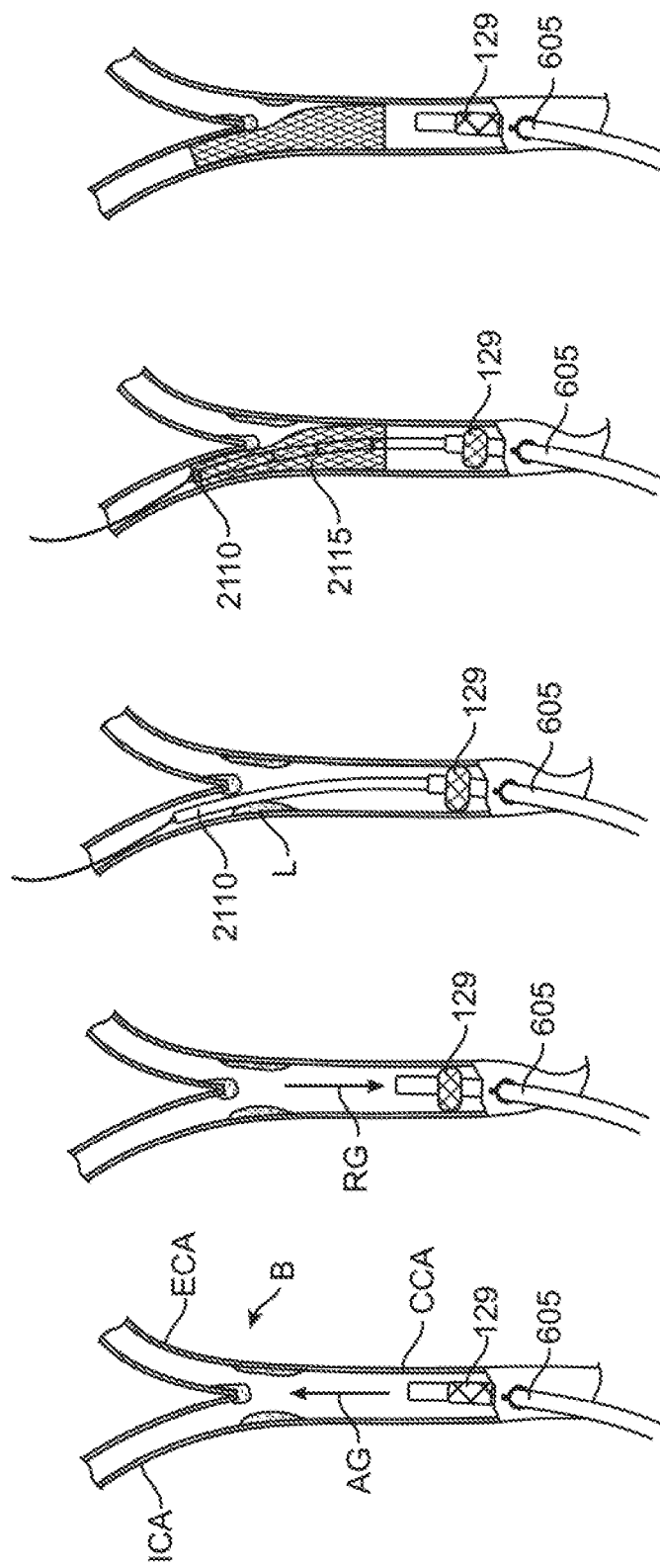

METHODS AND SYSTEMS FOR ESTABLISHING RETROGRADE CAROTID ARTERIAL BLOOD FLOW

REFERENCE TO PRIORITY DOCUMENT

This application is a continuation of co-pending U.S. patent application Ser. No. 15/728,747 entitled "Methods and Systems for Establishing Retrograde Carotid Arterial Blood Flow," filed Oct. 10, 2017, now U.S. Pat. No. 10,426,885, which is a continuation of U.S. patent application Ser. No. 15/168,809 entitled "Methods and Systems for Establishing Retrograde Carotid Arterial Blood Flow," filed May 31, 2016, now U.S. Pat. No. 9,789,242, which is a continuation of U.S. patent application Ser. No. 14/475,346, entitled "Methods and Systems for Establishing Retrograde Carotid Arterial Blood Flow," filed on Sep. 2, 2014, now U.S. Pat. No. 9,833,555, which is a continuation of U.S. patent application Ser. No. 13/050,876, entitled "Methods and Systems for Establishing Retrograde Carotid Arterial Blood Flow," filed on Mar. 17, 2011, now U.S. Pat. No. 9,011,364, which is a continuation of U.S. patent application Ser. No. 12/176,250, now U.S. Pat. No. 8,157,760, entitled "Methods and Systems for Establishing Retrograde Carotid Arterial Blood Flow," filed on Jul. 18, 2008, which claims the benefit under 35 U.S.C. § 119(e) of the following U.S. Provisional Patent Applications: (1) U.S. Provisional Patent Application Ser. No. 60/950,384 filed on Jul. 18, 2007 and (2) U.S. Provisional Patent Application Ser. No. 61/026,308 filed on Feb. 5, 2008. Priority of the aforementioned filing dates is hereby claimed, and the disclosures of the patent applications are hereby incorporated by reference in their entirety.

BACKGROUND

The present disclosure relates generally to medical methods and devices. More particularly, the present disclosure relates to methods and systems for accessing the carotid arterial vasculature and establishing retrograde blood flow during performance of carotid artery stenting and other procedures.

Carotid artery disease usually consists of deposits of plaque P which narrow the junction between the common carotid artery CCA and the internal carotid artery ICA, an artery which provides blood flow to the brain (FIG. 5). These deposits increase the risk of embolic particles being generated and entering the cerebral vasculature, leading to neurologic consequences such as transient ischemic attacks TIA, ischemic stroke, or death. In addition, should such narrowings become severe, blood flow to the brain is inhibited with serious and sometimes fatal consequences.

Two principal therapies are employed for treating carotid artery disease. The first is carotid endarterectomy CEA, an open surgical procedure which relies on occluding the common, internal and external carotid arteries, opening the carotid artery at the site of the disease (usually the carotid bifurcation where the common carotid artery CCA divides into the internal carotid artery ICA and external carotid artery ECA), dissecting away and removing the plaque P, and then closing the carotid artery. The second procedure relies on stenting of the carotid arteries, referred to as carotid artery stenting CAS, typically at or across the branch from the common carotid artery CAA into the internal carotid artery ICA, or entirely in the internal carotid artery. Usually, a self-expanding stent is introduced through percutaneous puncture into the femoral artery in the groin and up the aortic arch into the target common carotid artery CCA.

In both these approaches, the patient is at risk of emboli being released into the cerebral vasculature via the internal carotid artery ICA. The clinical consequence of emboli release into the external carotid artery ECA, an artery which provides blood to facial structures, is less significant. During CEA, the risk of emboli release into the internal carotid artery ICA is minimized by debriding and vigorously flushing the arteries before closing the vessels and restoring blood flow. During the procedure while the artery is opened, all the carotid arteries are occluded so particles are unable to enter the vasculature.

In carotid stenting CAS procedures, adjunct embolic protection devices are usually used to at least partially alleviate the risk of emboli. An example of these devices are distal filters, which are deployed in the internal carotid artery distal to the region of stenting. The filter is intended to capture the embolic particles to prevent passage into the cerebral vasculature. Such filtering devices, however, carry certain limitations. They must be advanced to the target vessel and cross the stenosis prior to deployment, which exposes the cerebral vascular to embolic showers; they are not always easy to advance, deploy, and remove through a tight stenosis and/or a severely angulated vasculature; and finally, they only filter particles larger than the filter pore size, typically 100 to 120 µm. Also, these devices do not filter 100% of the flow due to incomplete wall opposition of the filter, and furthermore there is a risk of debris escape during filter retrieval.

Of particular interest to the present disclosure, an alternative method for reducing the risk of emboli release into the internal carotid artery ICA has been proposed for use during carotid stenting CAS procedures utilizing the concept of reversing the flow in the internal carotid artery ICA to prevent embolic debris entering the cerebral vasculature. Although a number of specific protocols have been described, they generally rely on placing a sheath via the femoral artery (transfemoral access) into the common carotid artery. Flow in the common carotid artery is occluded, typically by inflating a balloon on the distal tip of the sheath. Flow into the external carotid artery ECA may also be occluded, typically using a balloon catheter or balloon guidewire introduced through the sheath. The sheath is then connected to a venous location or to a low pressure external receptacle in order to establish a reverse or retrograde flow from the internal carotid artery through the sheath and away from the cerebral vasculature. After such reverse or retrograde flow is established, the stenting procedure may be performed with a greatly reduced risk of emboli entering the cerebral vasculature.

An alternate system which simply halts forward flow in the ICA consists of a carotid access sheath with two integral balloons: an ECA occlusion balloon at the distal tip, and a CCA occlusion balloon placed some fixed distance proximal to the ECA balloon. Between the two balloons is an opening for delivery of the interventional carotid stenting devices. This system does not reverse flow from the ICA to the venous system, but instead relies on blocking flow and performing aspiration to remove embolic debris prior to establishing forward flow in the ICA.

While such reverse or static flow protocols for performing stenting and other interventional procedures in the carotid vasculature hold great promise, such methods have generally required the manipulation of multiple separate access and occlusion components. Moreover, the protocols have been rather complicated, requiring many separate steps, limiting their performance to only the most skilled vascular surgeons, interventional radiologists and cardiologists. In addition, due to the size limitations of the femoral access, the access devices themselves provide a very high resistance to flow, limiting the amount of reverse flow and/or aspiration possible. Furthermore, the requirement to occlude the external carotid artery adds risk and complexity to the procedure. The balloon catheter for occluding the external carotid artery can become trapped in the arterial wall in cases where the stent is placed across the bifurcation from the common carotid artery to the internal carotid artery, and may cause damage to the deployed stent when it is removed.

None of the cerebral protection devices and methods described offer protection after the procedure. However, generation of embolic particles have been measured up to 48 hours or later, after the stent procedure. During CEA, flushing at the end of the procedure while blocking flow to the internal carotid artery ICA may help reduce post-procedure emboli generation. A similar flushing step during CAS may also reduce emboli risk. Additionally, a stent which is designed to improve entrapment of embolic particles may also reduce post-procedure emboli.

In addition, all currently available carotid stenting and cerebral protection systems are designed for access from the femoral artery. Unfortunately, the pathway from the femoral artery to the common carotid artery is relatively long, has several turns which in some patients can be quite angulated, and often contains plaque and other diseases. The portion of the procedure involving access to the common carotid artery from the femoral artery can be difficult and time consuming as well as risk generating showers of embolic debris up both the target and the opposite common carotid artery and thence to the cerebral vasculature. Some studies suggest that up to half, or more, of embolic complications during CAS procedures occur during access to the CCA. None of the protocols or systems offer protection during this portion of the procedure.

Recently, a reverse flow protocol having an alternative access route to the carotid arteries has been proposed by Criado. This alternative route consists of direct surgical access to the common carotid artery CCA, called transcervical access. Transcervical access greatly shortens the length and tortuosity of the pathway from the vascular access point to the target treatment site thereby easing the time and difficulty of the procedure. Additionally, this access route reduces the risk of emboli generation from navigation of diseased, angulated, or tortuous aortic arch or common carotid artery anatomy.

The Criado protocol is described in several publications in the medical literature cited below. As shown in FIG. 3, the Criado protocol uses a flow shunt which includes an arterial sheath 210 and a venous sheath 212. Each sheath has a side arm 214, terminating in a stopcock 216. The two sheaths stopcocks are connected by a connector tubing 218, thus completing a reverse flow shunt from the arterial sheath 210 to the venous sheath 212 The arterial sheath is placed in the common carotid artery CCA through an open surgical incision in the neck below the carotid bifurcation. Occlusion of the common carotid artery CCA is accomplished using a temporary vessel ligation, for example using a Rummel tourniquet and umbilical tape or vessel loop. The venous return sheath 212 is placed in the internal jugular vein IJV (FIG. 3), also via an open surgical incision. Retrograde flow from the internal carotid artery ICA and the external carotid artery ECA may then be established by opening the stopcock 216. The Criado protocol is an improvement over the earlier retrograde flow protocols since it eliminates the need for femoral access. Thus, the potential complications associated with the femoral access are completely avoided. Furthermore, the lower flow restrictions presented by the shorter access route offer the opportunity for more vigorous reverse flow rate, increasing the efficiency of embolic debris removal. Because of these reduced flow restrictions, the desired retrograde flow of the internal carotid artery ICA may be established without occluding the external carotid artery ECA, as required by the earlier protocols.

While a significant improvement over the femoral access-based retrograde flow protocols, the Criado protocol and flow shunt could still benefit from improvement. In particular, the existing arterial and venous sheaths used in the procedure still have significant flow restrictions in the side arms 214 and stopcocks 216. When an interventional catheter is inserted into the arterial access sheath, the reverse flow circuit resistance is at a maximum. In some percentage of patients, the external carotid artery ECA perfusion pressure is greater than the internal carotid artery ICA perfusion pressure. In these patients, this differential pressure might drive antegrade flow into the ICA from the ECA. A reverse flow shunt with lower flow resistance could guarantee reversal of flow in both the ECA and ICA despite a pressure gradient from the ECA to the ICA.

In addition, there is no means to monitor or regulate the reverse flow rate. The ability to increase and/or modulate the flow rate would give the user the ability to set the reverse flow rate optimally to the tolerance and physiology of the patient and the stage of the procedure, and thus offer improved protection from embolic debris. Further, the system as described by Criado relies on manually turning one or more stopcocks to open and close the reverse flow shunt, for example during injection of contrast medium to facilitate placement of the CAS systems. Finally, the Criado protocol relies on open surgical occlusion of the common carotid artery, via a vessel loop or Rummel tourniquet. A system with means to occlude the common carotid artery intravascularly, for example with an occlusion element on the arterial access sheath, would allow the entire procedure to be performed using percutaneous techniques. A percutaneous approach would limit the size and associated complications of a surgical incision, as well as enable non-surgical physicians to perform the procedure.

For these reasons, it would be desirable to provide improved methods, apparatus, and systems for performing transcervical access, retrograde flow and flushing procedures and implantation of a carotid stent in the carotid arterial vasculature to reduce the risk of procedural and post-procedural emboli, to improve the level of hemostasis throughout the procedure, and to improve the ease and speed of carotid artery stenting. The methods, apparatus, and system should simplify the procedure to be performed by the physician as well as reduce the risk of improperly performing the procedures and/or achieving insufficient retrograde flow and flushing to protect against emboli release. The systems should provide individual devices and components which are readily used with each other and which protect against emboli-related complications. The methods and systems should also provide for convenient and preferably automatic closure of any and all arterial penetrations at the end of the procedure to prevent unintended blood loss. Additionally, the systems, apparatus, and methods should be suitable for performance by either open surgical or percutaneous access routes into the vasculature. Additionally, the methods, apparatus, and systems should enable implantation of an intravascular prosthetic implant which lowers post procedural complications. At least some of these objectives will be met by the inventions described herein below.

SUMMARY

The disclosed methods, apparatus, and systems establish and facilitate retrograde or reverse flow blood circulation in the region of the carotid artery bifurcation in order to limit or prevent the release of emboli into the cerebral vasculature, particularly into the internal carotid artery. The methods are particularly useful for interventional procedures, such as stenting and angioplasty, atherectomy, performed through a transcervical approach or transfemoral into the common carotid artery, either using an open surgical technique or using a percutaneous technique, such as a modified Seldinger technique.

Access into the common carotid artery is established by placing a sheath or other tubular access cannula into a lumen of the artery, typically having a distal end of the sheath positioned proximal to the junction or bifurcation B (FIG. 5) from the common carotid artery to the internal and external carotid arteries. The sheath may have an occlusion member at the distal end, for example a compliant occlusion balloon. A catheter or guidewire with an occlusion member, such as a balloon, may be placed through the access sheath and positioned in the proximal external carotid artery ECA to inhibit the entry of emboli, but occlusion of the external carotid artery is usually not necessary. A second return sheath is placed in the venous system, for example the internal jugular vein IJV or femoral vein FV. The arterial access and venous return sheaths are connected to create an external arterial-venous shunt.

Retrograde flow is established and modulated to meet the patient's requirements. Flow through the common carotid artery is occluded, either with an external vessel loop or tape, a vascular clamp, an internal occlusion member such as a balloon, or other type of occlusion means. When flow through the common carotid artery is blocked, the natural pressure gradient between the internal carotid artery and the venous system will cause blood to flow in a retrograde or reverse direction from the cerebral vasculature through the internal carotid artery and through the shunt into the venous system.

Alternately, the venous sheath could be eliminated and the arterial sheath could be connected to an external collection reservoir or receptacle. The reverse flow could be collected in this receptacle. If desired, the collected blood could be filtered and subsequently returned to the patient during or at the end of the procedure. The pressure of the receptacle could be open to zero pressure, causing the pressure gradient to create blood to flow in a reverse direction from the cerebral vasculature to the receptacle or the pressure of the receptacle could be a negative pressure.

Optionally, to achieve or enhance reverse flow from the internal carotid artery, flow from the external carotid artery may be blocked, typically by deploying a balloon or other occlusion element in the external carotid just above (i.e., distal) the bifurcation within the internal carotid artery.

Although the procedures and protocols described hereinafter will be particularly directed at carotid stenting, it will be appreciated that the methods for accessing the carotid artery described herein would also be useful for angioplasty, artherectomy, and any other interventional procedures which might be carried out in the carotid arterial system, particularly at a location near the bifurcation between the internal and external carotid arteries. In addition, it will be appreciated that some of these access, vascular closure, and embolic protection methods will be applicable in other vascular interventional procedures, for example the treatment of acute stroke.

The present disclosure includes a number of specific aspects for improving the performance of carotid artery access protocols. At least most of these individual aspects and improvements can be performed individually or in combination with one or more other of the improvements in order to facilitate and enhance the performance of the particular interventions in the carotid arterial system.

In one aspect, there is disclosed a system for use in accessing and treating a carotid artery, said system. The system comprises an arterial access device adapted to be introduced into a common carotid artery and receive blood flow from the common carotid artery; a shunt fluidly connected to the arterial access device, wherein the shunt provides a pathway for blood to flow from the arterial access device to a return site; and a flow control assembly coupled to the shunt and adapted to regulate blood flow through the shunt between at least a first blood flow state and at least a second blood flow state, wherein the flow control assembly includes one or more components that interact with the blood flow through the shunt.

In another aspect, there is disclosed a system for use in accessing and treating a carotid artery. The system comprises an arterial access device adapted to be introduced into a common carotid artery and receive blood flow from the common carotid artery; a shunt fluidly connected to the arterial access device, wherein the shunt provides a pathway for blood to flow from the arterial access device to a return site; a flow mechanism coupled to the shunt and adapted to vary the blood flow through the shunt between a first blood flow rate and a second blood flow rate; and a controller that automatically interacts with the flow mechanism to regulate blood flow through the shunt between the first blood flow rate and the second blood flow rate without requiring input from a user.

In another aspect, there is disclosed a device for use in accessing and treating a carotid artery. The device comprises a distal sheath having a distal end adapted to be introduced into the common carotid artery, a proximal end, and a lumen extending between the distal and proximal ends; a proximal extension having a distal end, a proximal end, and a lumen therebetween, wherein the distal end of the proximal extension is connected to the proximal end of the sheath at a junction so that the lumens of each are contiguous; a flow line having a lumen, said flow line connected near the junction so that blood flowing into the distal end of the sheath can flow into the lumen of the flow line; and a hemostasis valve at the proximal end of the proximal extension, said hemostasis valve being adapted to inhibit blood flow from the proximal extension while allowing catheter introduction through the proximal extension and into the distal sheath.

In another aspect, there is disclosed a method for accessing and treating a carotid artery. The method comprises forming a penetration in a wall of a common carotid artery; positioning an access sheath through the penetration; blocking blood flow from the common carotid artery past the sheath; allowing retrograde blood flow from the carotid artery into the sheath and from the sheath via a flow path to a return site; and modifying blood flow through the flow path based on feedback data.

In another aspect, there is disclosed a method for accessing and treating a carotid artery. The method comprises forming a penetration in a wall of a common carotid artery; positioning an access sheath through the penetration; blocking blood flow from the common carotid artery past the sheath; allowing retrograde blood flow from the carotid artery into the sheath and from the sheath via a flow path to a return site; and monitoring flow through the flow path.

In another aspect, there is disclosed a method for accessing and treating a carotid artery. The method comprises: forming a penetration in a wall of a common carotid artery; positioning an arterial access sheath through the penetration; blocking blood flow from the common carotid artery past the sheath; allowing retrograde blood flow from the internal carotid artery into the sheath while the common carotid artery remains blocked; and adjusting the state of retrograde blood flow through the sheath.

In another aspect, there is disclosed a method for accessing and treating a carotid artery. The method comprises forming a penetration in a wall of a common carotid artery; positioning an arterial access sheath through the penetration; blocking blood flow from the common carotid artery past the sheath; allowing retrograde blood flow from the internal carotid artery into the sheath while the common carotid artery remains blocked; and adjusting a rate of retrograde blood flow from the sheath to as high a level as the patient will tolerate, wherein said adjusted rate is a baseline.

Other features and advantages should be apparent from the following description of various embodiments, which illustrate, by way of example, the principles of the invention.

BRIEF DESCRIPTION OF THE DRAWINGS

FIG. 6A illustrates an arterial access device useful in the methods and systems of the present disclosure.

FIG. 6B illustrates an additional arterial access device construction with a reduced diameter distal end.

FIGS. 7A and 7B illustrate a tube useful with the sheath of FIG. 6A.

FIG. 8A illustrates an additional arterial access device construction with an expandable occlusion element.

FIG. 8B illustrates an additional arterial access device construction with an expandable occlusion element and a reduced diameter distal end.

FIGS. 12A-12D, FIGS. 13A-13D, FIGS. 14A and 14B, FIGS. 15A-15D, and FIGS. 16A and 16B, illustrate different embodiments of a variable flow resistance component useful in the methods and systems of the present disclosure.

FIGS. 21A-21E illustrate the exemplary blood flow paths during a procedure for implanting a stent at the carotid bifurcation in accordance with the principles of the present disclosure.

DETAILED DESCRIPTION

Figure 1A:
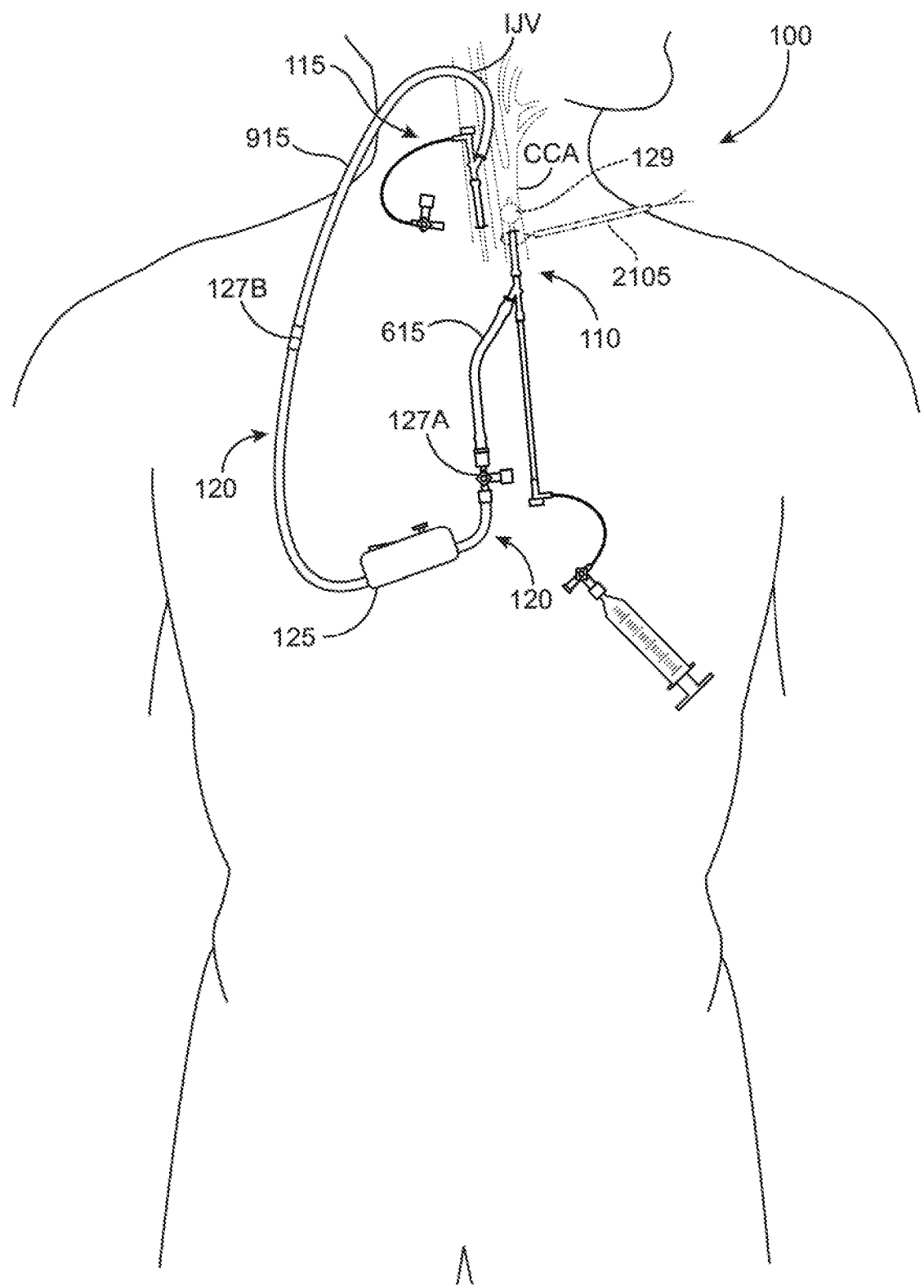
FIG. 1A is a schematic illustration of a retrograde blood flow system including a flow control assembly wherein an arterial access device accesses the common carotid artery via a transcervical approach and a venous return device communicates with the internal jugular vein.

FIG. 1A shows a first embodiment of a retrograde flow system 100 that is adapted to establish and facilitate retrograde or reverse flow blood circulation in the region of the carotid artery bifurcation in order to limit or prevent the release of emboli into the cerebral vasculature, particularly into the internal carotid artery. The system 100 interacts with the carotid artery to provide retrograde flow from the carotid artery to a venous return site, such as the internal jugular vein (or to another return site such as another large vein or an external receptacle in alternate embodiments.) The retrograde flow system 100 includes an arterial access device 110, a venous return device 115, and a shunt 120 that provides a passageway for retrograde flow from the arterial access device 110 to the venous return device 115. A flow control assembly 125 interacts with the shunt 120. The flow control assembly 125 is adapted to regulate and/or monitor the retrograde flow from the common carotid artery to the internal jugular vein, as described in more detail below. The flow control assembly 125 interacts with the flow pathway through the shunt 120, either external to the flow path, inside the flow path, or both. The arterial access device 110 at least partially inserts into the common carotid artery CCA and the venous return device 115 at least partially inserts into a venous return site such as the internal jugular vein IJV, as described in more detail below. The arterial access device 110 and the venous return device 115 couple to the shunt 120 at connection locations 127a and 127b. When flow through the common carotid artery is blocked, the natural pressure gradient between the internal carotid artery and the venous system causes blood to flow in a retrograde or reverse direction RG (FIG. 2A) from the cerebral vasculature through the internal carotid artery and through the shunt 120 into the venous system. The flow control assembly 125 modulates, augments, assists, monitors, and/or otherwise regulates the retrograde blood flow.

In the embodiment of FIG. 1A, the arterial access device 110 accesses the common carotid artery CCA via a transcervical approach. Transcervical access provides a short length and non-tortuous pathway from the vascular access point to the target treatment site thereby easing the time and difficulty of the procedure, compared for example to a transfemoral approach. Additionally, this access route reduces the risk of emboli generation from navigation of diseased, angulated, or tortuous aortic arch or common carotid artery anatomy. At least a portion of the venous return device 115 is placed in the internal jugular vein UV. In an embodiment, transcervical access to the common carotid artery is achieved percutaneously via an incision or puncture in the skin through which the arterial access device 110 is inserted. If an incision is used, then the incision can be about 0.5 cm in length. An occlusion element 129, such as an expandable balloon, can be used to occlude the common carotid artery CCA at a location proximal of the distal end of the arterial access device 110. The occlusion element 129 can be located on the arterial access device 110 or it can be located on a separate device. In an alternate embodiment, the arterial access device 110 accesses the common carotid artery CCA via a direct surgical transcervical approach. In the surgical approach, the common carotid artery can be occluded using a tourniquet 2105. The tourniquet 2105 is shown in phantom to indicate that it is a device that is used in the optional surgical approach.

Figure 1B:
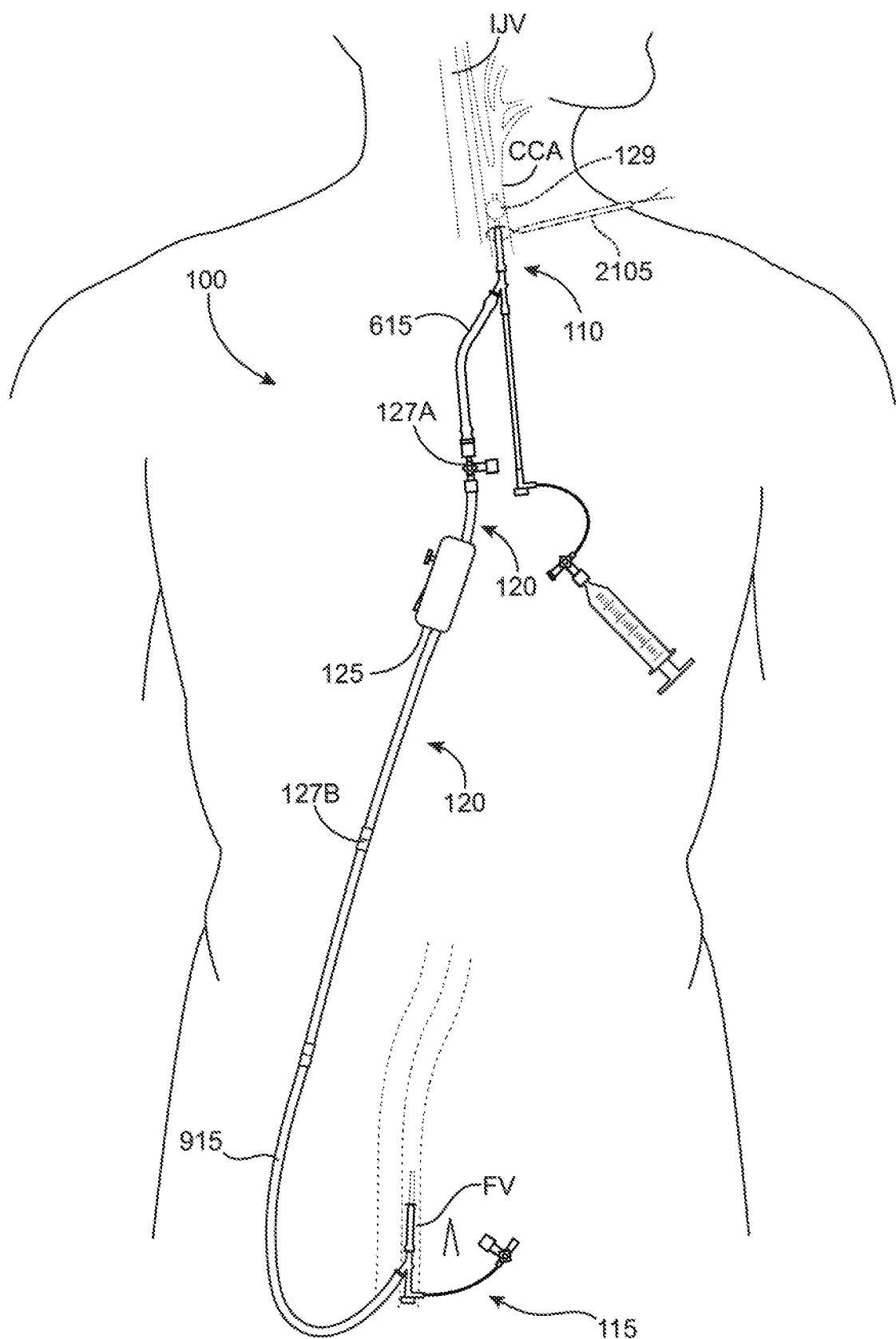
FIG. 1B is a schematic illustration of a retrograde blood flow system wherein an arterial access device accesses the common carotid artery via a transcervical approach and a venous return device communicates with the femoral vein.

In another embodiment, shown in FIG. 1B, the arterial access device 110 accesses the common carotid artery CCA via a transcervical approach while the venous return device 115 access a venous return site other than the jugular vein, such as a venous return site comprised of the femoral vein FV. The venous return device 115 can be inserted into a central vein such as the femoral vein FV via a percutaneous puncture in the groin.

Figure 1C:
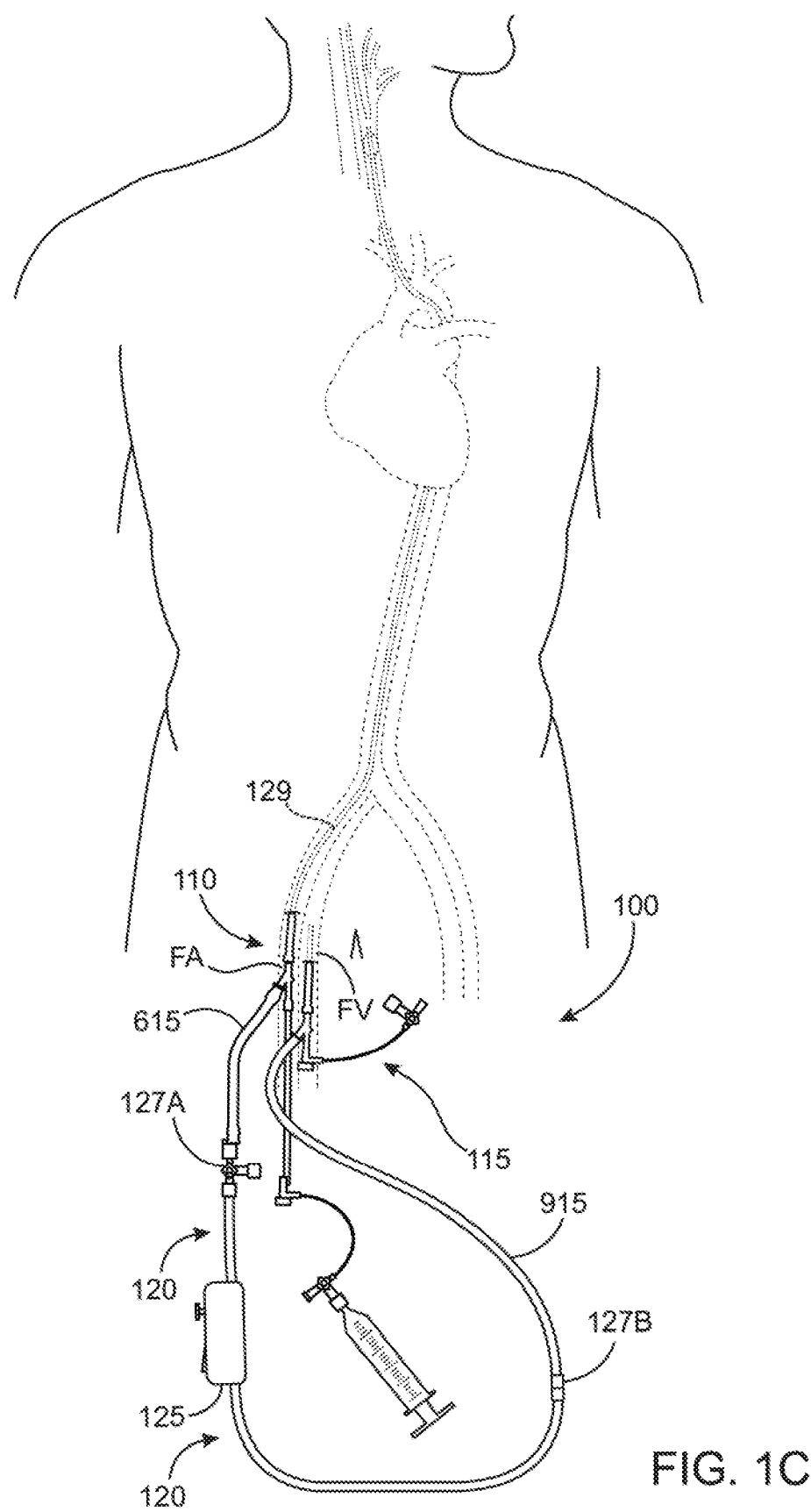
FIG. 1C is a schematic illustration of a retrograde blood flow system wherein an arterial access device accesses the common carotid artery via a transfemoral approach and a venous return device communicates with the femoral vein.

In another embodiment, shown in FIG. 1C, the arterial access device 110 accesses the common carotid artery via a femoral approach. According to the femoral approach, the arterial access device 110 approaches the CCA via a percutaneous puncture into the femoral artery FA, such as in the groin, and up the aortic arch AA into the target common carotid artery CCA. The venous return device 115 can communicate with the jugular vein JV or the femoral vein FV.

Figure 1D:
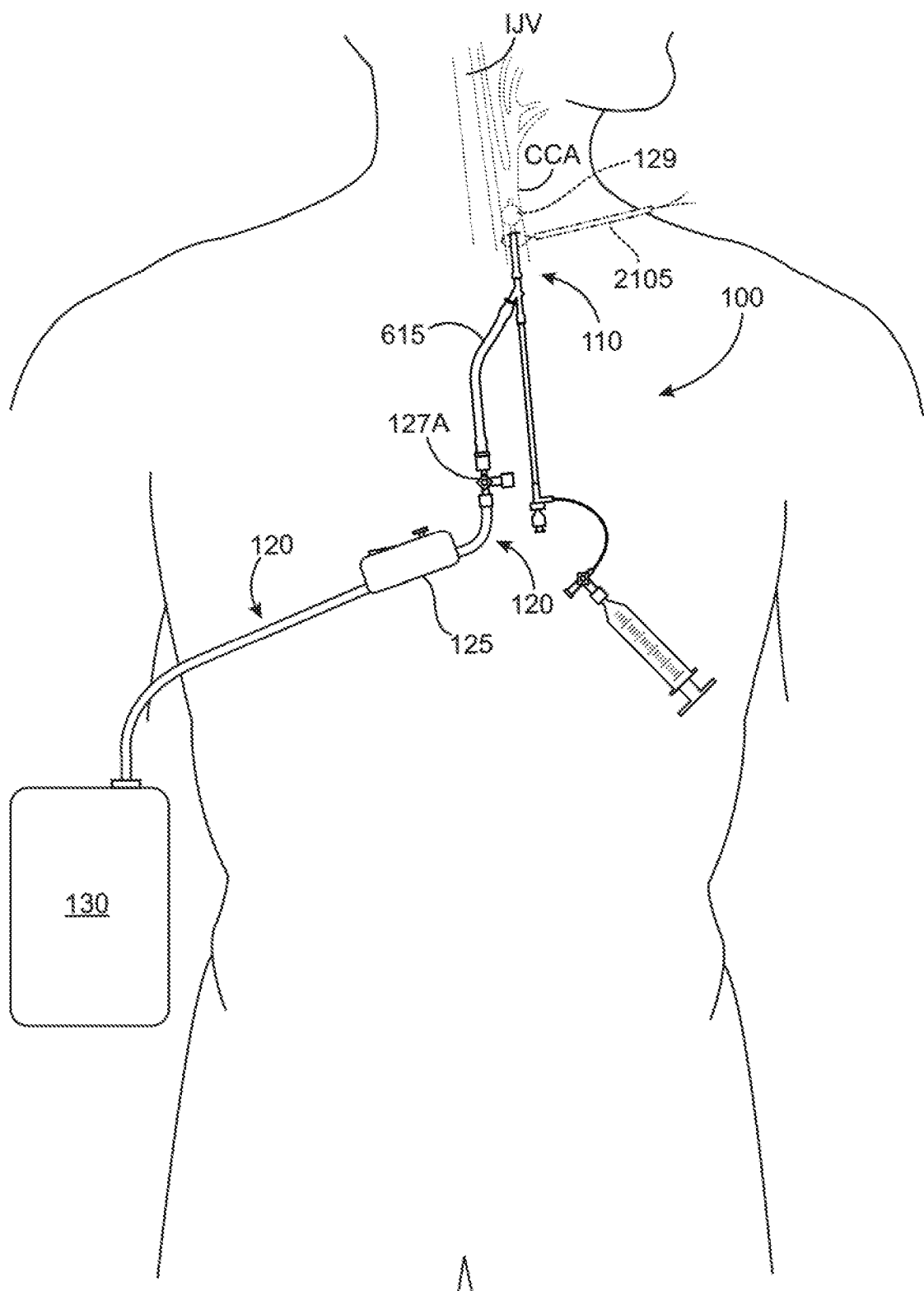
FIG. 1D is a schematic illustration of a retrograde blood flow system wherein retrograde flow is collected in an external receptacle.

FIG. 1D shows yet another embodiment, wherein the system provides retrograde flow from the carotid artery to an external receptacle 130 rather than to a venous return site. The arterial access device 110 connects to the receptacle 130 via the shunt 120, which communicates with the flow control assembly 125. The retrograde flow of blood is collected in the receptacle 130. If desired, the blood could be filtered and subsequently returned to the patient. The pressure of the receptacle 130 could be set at zero pressure (atmospheric pressure) or even lower, causing the blood to flow in a reverse direction from the cerebral vasculature to the receptacle 130. Optionally, to achieve or enhance reverse flow from the internal carotid artery, flow from the external carotid artery can be blocked, typically by deploying a balloon or other occlusion element in the external carotid artery just above the bifurcation with the internal carotid artery. FIG. 1D shows the arterial access device 110 arranged in a transcervical approach with the CCA although it should be appreciated that the use of the external receptacle 130 can also be used with the arterial access device 110 in a transfemoral approach.

Figure 2A:
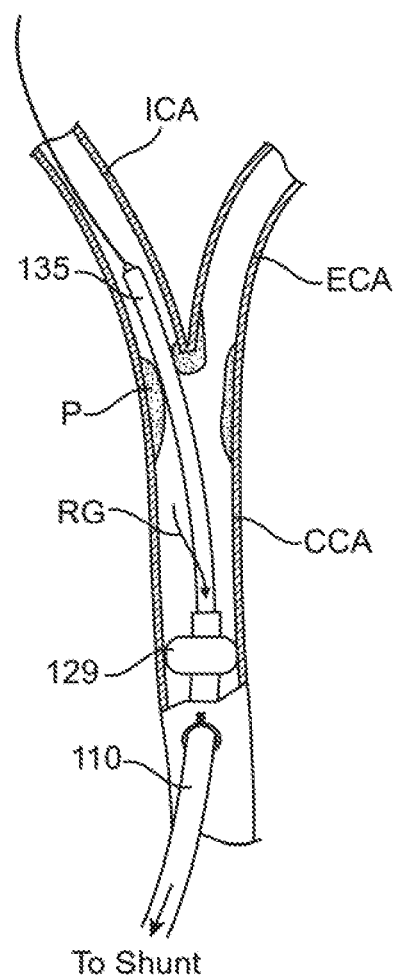
FIG. 2A is an enlarged view of the carotid artery wherein the carotid artery is occluded and connected to a reverse flow shunt, and an interventional device, such as a stent delivery system or other working catheter, is introduced into the carotid artery via an arterial access device.

With reference to the enlarged view of the carotid artery in FIG. 2A, an interventional device, such as a stent delivery system 135 or other working catheter, can be introduced into the carotid artery via the arterial access device 110, as described in detail below. The stent delivery system 135 can be used to treat the plaque P such as to deploy a stent into the carotid artery. The arrow RG in FIG. 2A represents the direction of retrograde flow.

Figure 2B:
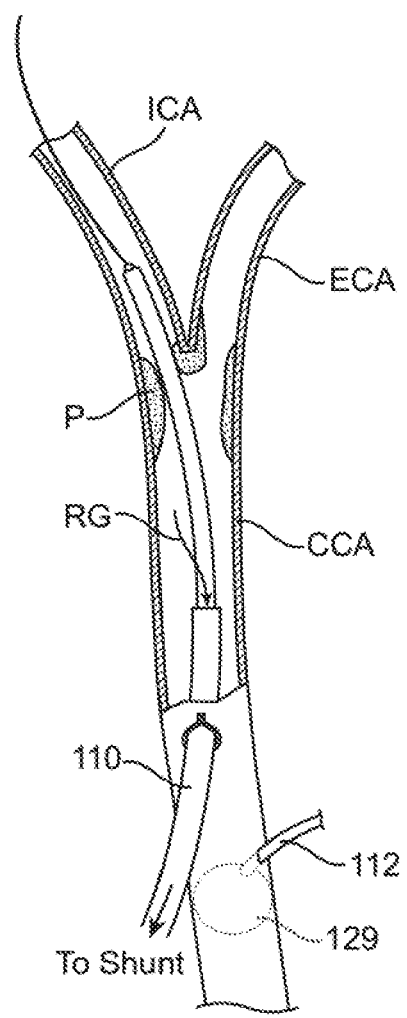
FIG. 2B is an alternate system wherein the carotid artery is connected to a reverse flow shunt and an interventional device, such as a stent delivery system or other working catheter, is introduced into the carotid artery via an arterial access device, and the carotid artery is occluded with a separate occlusion device.

FIG. 2B shows another embodiment, wherein the arterial access device 110 is used for the purpose of creating an arterial-to-venous shunt as well as introduction of at least one interventional device into the carotid artery. A separate arterial occlusion device 112 with an occlusion element 129 can be used to occlude the common carotid artery CCA at a location proximal to the distal end of the arterial access device 110.

Figure 2C:
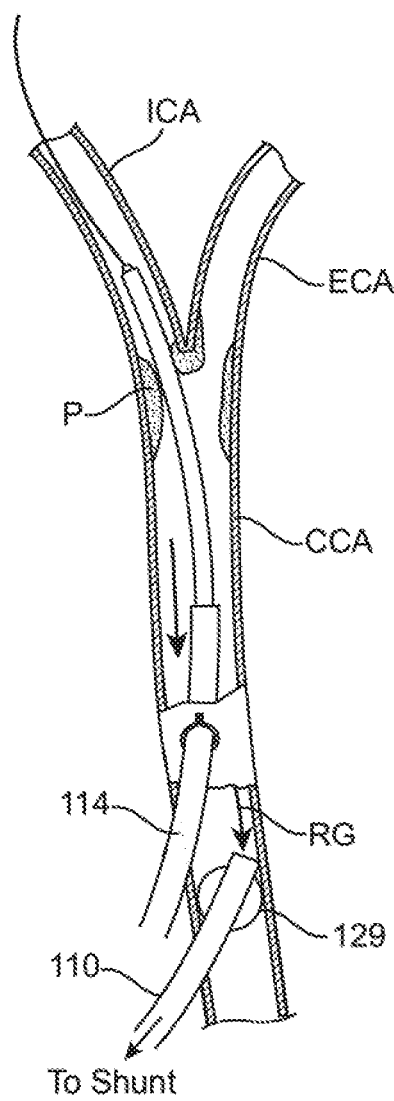
FIG. 2C is an alternate system wherein the carotid artery is occluded and the artery is connected to a reverse flow shunt via an arterial access device and the interventional device, such as a stent delivery system, is introduced into the carotid artery via an arterial introducer device.
Figure 3:
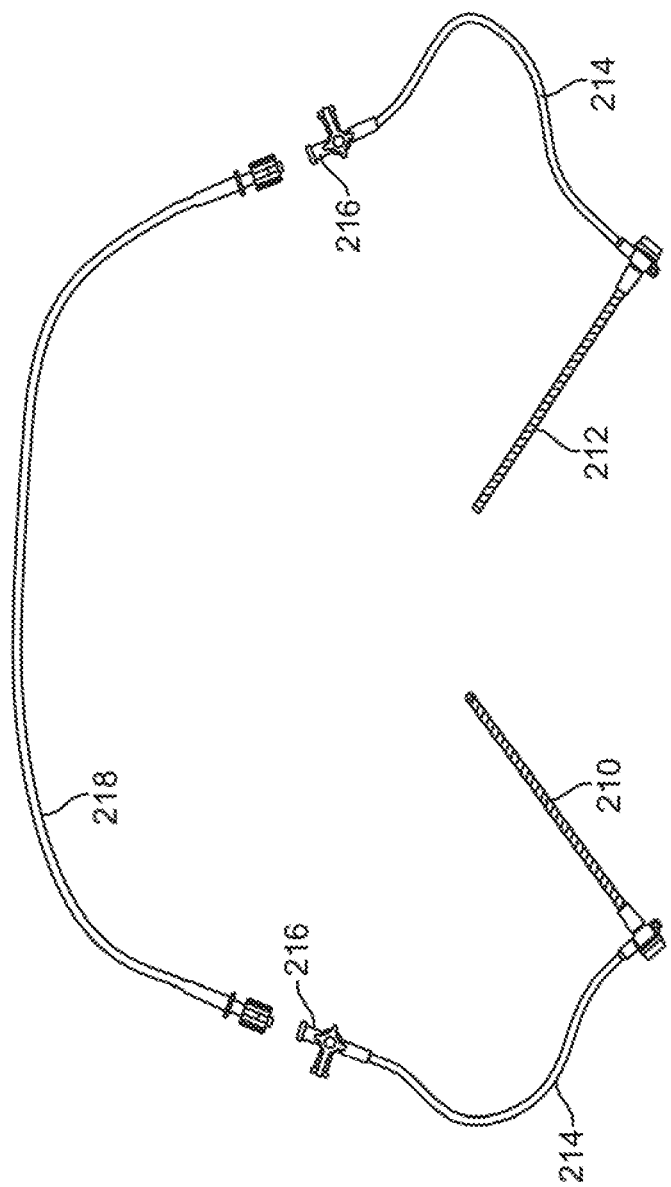
FIG. 3 illustrates a prior art Criado flow shunt system.

FIG. 2C shows yet another embodiment wherein the arterial access device 110 is used for the purpose of creating an arterial-to-venous shunt as well as arterial occlusion using an occlusion element 129. A separate arterial introducer device can be used for the introduction of at least one interventional device into the carotid artery at a location distal to the arterial access device 110.

Description Of Anatomy

Collateral Brain Circulation

The Circle of Willis CW is the main arterial anastomatic trunk of the brain where all major arteries which supply the brain, namely the two internal carotid arteries (ICAs) and the vertebral basilar system, connect. The blood is carried from the Circle of Willis by the anterior, middle and posterior cerebral arteries to the brain. This communication between arteries makes collateral circulation through the brain possible. Blood flow through alternate routes is made possible thereby providing a safety mechanism in case of blockage to one or more vessels providing blood to the brain. The brain can continue receiving adequate blood supply in most instances even when there is a blockage somewhere in the arterial system (e.g., when the ICA is ligated as described herein). Flow through the Circle of Willis ensures adequate cerebral blood flow by numerous pathways that redistribute blood to the deprived side.

The collateral potential of the Circle of Willis is believed to be dependent on the presence and size of its component vessels. It should be appreciated that considerable anatomic variation between individuals can exist in these vessels and that many of the involved vessels may be diseased. For example, some people lack one of the communicating arteries. If a blockage develops in such people, collateral circulation is compromised resulting in an ischemic event and potentially brain damage. In addition, an autoregulatory response to decreased perfusion pressure can include enlargement of the collateral arteries, such as the communicating arteries, in the Circle of Willis. An adjustment time is occasionally required for this compensation mechanism before collateral circulation can reach a level that supports normal function. This autoregulatory response can occur over the space of 15 to 30 seconds and can only compensate within a certain range of pressure and flow drop. Thus, it is possible for a transient ischemic attack to occur during the adjustment period. Very high retrograde flow rate for an extended period of time can lead to conditions where the patient's brain is not getting enough blood flow, leading to patient intolerance as exhibited by neurologic symptoms or in some cases a transient ischemic attack.

Figure 4:
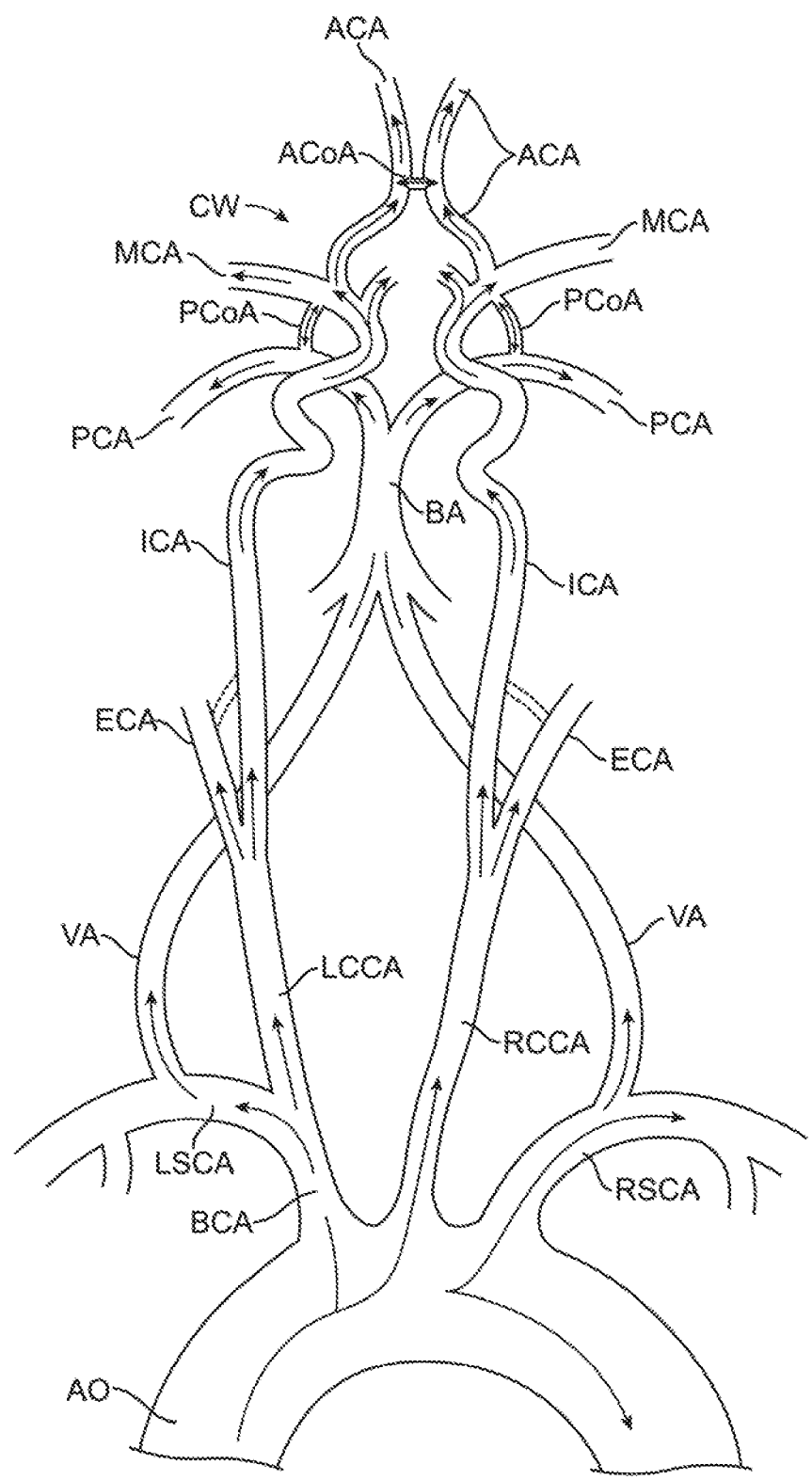
FIG. 4 illustrates a normal cerebral circulation diagram including the Circle of Willis.

FIG. 4 depicts a normal cerebral circulation and formation of Circle of Willis CW. The aorta AO gives rise to the brachiocephalic artery BCA, which branches into the left common carotid artery LCCA and left subclavian artery LSCA. The aorta AO further gives rise to the right common carotid artery RCCA and right subclavian artery RSCA. The left and right common carotid arteries CCA gives rise to internal carotid arteries ICA which branch into the middle cerebral arteries MCA, posterior communicating artery PcoA, and anterior cerebral artery ACA. The anterior cerebral arteries ACA deliver blood to some parts of the frontal lobe and the corpus striatum. The middle cerebral arteries MCA are large arteries that have tree-like branches that bring blood to the entire lateral aspect of each hemisphere of the brain. The left and right posterior cerebral arteries PCA arise from the basilar artery BA and deliver blood to the posterior portion of the brain (the occipital lobe).

Anteriorly, the Circle of Willis is formed by the anterior cerebral arteries ACA and the anterior communicating artery ACoA which connects the two ACAs. The two posterior communicating arteries PCoA connect the Circle of Willis to the two posterior cerebral arteries PCA, which branch from the basilar artery BA and complete the Circle posteriorly.

The common carotid artery CCA also gives rise to external carotid artery ECA, which branches extensively to supply most of the structures of the head except the brain and the contents of the orbit. The ECA also helps supply structures in the neck and face.

Carotid Artery Bifurcation

Figure 5:
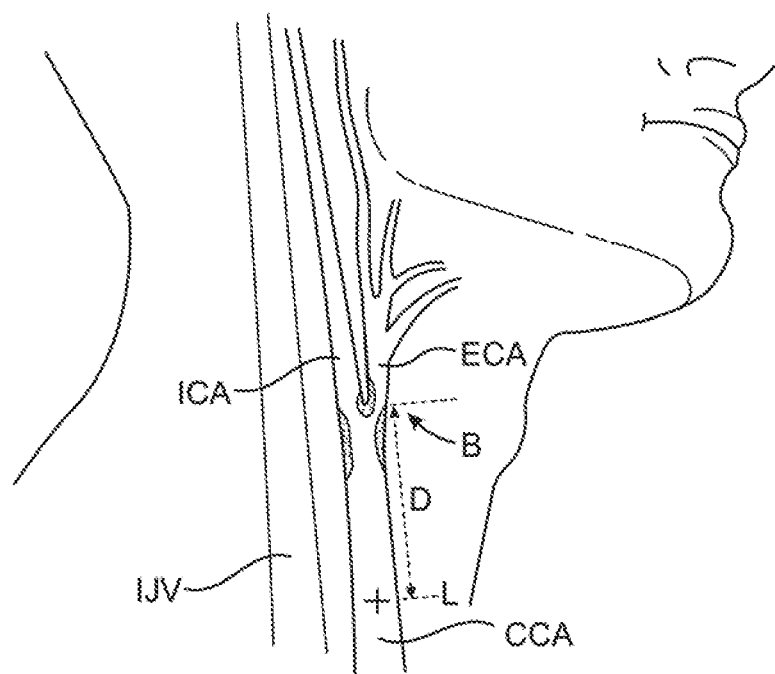
FIG. 5 illustrates the vasculature in a patient's neck, including the common carotid artery CCA, the internal carotid artery ICA, the external carotid artery ECA, and the internal jugular vein IJV.

FIG. 5 shows an enlarged view of the relevant vasculature in the patient's neck. The common carotid artery CCA branches at bifurcation B into the internal carotid artery ICA and the external carotid artery ECA. The bifurcation is located at approximately the level of the fourth cervical vertebra. FIG. 5 shows plaque P formed at the bifurcation B.

As discussed above, the arterial access device 110 can access the common carotid artery CCA via a transcervical approach. Pursuant to the transcervical approach, the arterial access device 110 is inserted into the common carotid artery CCA at an arterial access location L, which can be, for example, a surgical incision or puncture in the wall of the common carotid artery CCA. There is typically a distance D of around 5 to 7 cm between the arterial access location L and the bifurcation B. When the arterial access device 110 is inserted into the common carotid artery CCA, it is undesirable for the distal tip of the arterial access device 110 to contact the bifurcation B as this could disrupt the plaque P and cause generation of embolic particles. In order to minimize the likelihood of the arterial access device 110 contacting the bifurcation B, in an embodiment only about 2-4 cm of the distal region of the arterial access device is inserted into the common carotid artery CCA during a procedure.

The common carotid arteries are encased on each side in a layer of fascia called the carotid sheath. This sheath also envelops the internal jugular vein and the vagus nerve. Anterior to the sheath is the sternocleidomastoid muscle. Transcervical access to the common carotid artery and internal jugular vein, either percutaneous or surgical, can be made immediately superior to the clavicle, between the two heads of the sternocleidomastoid muscle and through the carotid sheath, with care taken to avoid the vagus nerve.

At the upper end of this sheath, the common carotid artery bifurcates into the internal and external carotid arteries. The internal carotid artery continues upward without branching until it enters the skull to supply blood to the retina and brain. The external carotid artery branches to supply blood to the scalp, facial, ocular, and other superficial structures. Intertwined both anterior and posterior to the arteries are several facial and cranial nerves. Additional neck muscles may also overlay the bifurcation. These nerve and muscle structures can be dissected and pushed aside to access the carotid bifurcation during a carotid endarterectomy procedure. In some cases the carotid bifurcation is closer to the level of the mandible, where access is more challenging and with less room available to separate it from the various nerves which should be spared. In these instances, the risk of inadvertent nerve injury can increase and an open endarterectomy procedure may not be a good option.

Detailed Description Of Retrograde Blood Flow System

As discussed, the retrograde flow system 100 includes the arterial access device 110, venous return device 115, and shunt 120 which provides a passageway for retrograde flow from the arterial access device 110 to the venous return device 115. The system also includes the flow control assembly 125, which interacts with the shunt 120 to regulate and/or monitor retrograde blood flow through the shunt 120. Exemplary embodiments of the components of the retrograde flow system 100 are now described.

Arterial Access Device

FIG. 6A shows an exemplary embodiment of the arterial access device 110, which comprises a distal sheath 605, a proximal extension 610, a flow line 615, an adaptor or Y-connector 620, and a hemostasis valve 625. The distal sheath 605 is adapted to be introduced through an incision or puncture in a wall of a common carotid artery, either an open surgical incision or a percutaneous puncture established, for example, using the Seldinger technique. The length of the sheath can be in the range from 5 to 15 cm, usually being from 10 cm to 12 cm. The inner diameter is typically in the range from 7 Fr (1 Fr=0.33 mm), to 10 Fr, usually being 8 Fr. Particularly when the sheath is being introduced through the transcervical approach, above the clavicle but below the carotid bifurcation, it is desirable that the sheath 605 be highly flexible while retaining hoop strength to resist kinking and buckling. Thus, the distal sheath 605 can be circumferentially reinforced, such as by braid, helical ribbon, helical wire, or the like. In an alternate embodiment, the distal sheath is adapted to be introduced through a percutaneous puncture into the femoral artery, such as in the groin, and up the aortic arch AA into the target common carotid artery CCA.

The distal sheath 605 can have a stepped or other configuration having a reduced diameter distal region 630, as shown in FIG. 6B, which shows an enlarged view of the distal region 630 of the sheath 605. The distal region 630 of the sheath can be sized for insertion into the carotid artery, typically having an inner diameter in the range from 2.16 mm (0.085 inch) to 2.92 mm (0.115 inch) with the remaining proximal region of the sheath having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcervical approach with reduced risk that the distal end of the sheath 605 will contact the bifurcation B. Moreover, the reduced diameter section 630 also permits a reduction in size of the arteriotomy for introducing the sheath 605 into the artery while having a minimal impact in the level of flow resistance.

With reference again to FIG. 6A, the proximal extension 610 has an inner lumen which is contiguous with an inner lumen of the sheath 605. The lumens can be joined by the Y-connector 620 which also connects a lumen of the flow line 615 to the sheath. In the assembled system, the flow line 615 connects to and forms a first leg of the retrograde shunt 120 (FIG. 1). The proximal extension 610 can have a length sufficient to space the hemostasis valve 625 well away from the Y-connector 620, which is adjacent to the percutaneous or surgical insertion site. By spacing the hemostasis valve 625 away from a percutaneous insertion site, the physician can introduce a stent delivery system or other working catheter into the proximal extension 610 and sheath 605 while staying out of the fluoroscopic field when fluoroscopy is being performed.

A flush line 635 can be connected to the side of the hemostasis valve 625 and can have a stopcock 640 at its proximal or remote end. The flush-line 635 allows for the introduction of saline, contrast fluid, or the like, during the procedures. The flush line 635 can also allow pressure monitoring during the procedure. A dilator 645 having a tapered distal end 650 can be provided to facilitate introduction of the distal sheath 605 into the common carotid artery. The dilator 645 can be introduced through the hemostasis valve 625 so that the tapered distal end 650 extends through the distal end of the sheath 605, as best seen in FIG. 7A. The dilator 645 can have a central lumen to accommodate a guide wire. Typically, the guide wire is placed first into the vessel, and the dilator/sheath combination travels over the guide wire as it is being introduced into the vessel.

Optionally, a tube 705 may be provided which is coaxially received over the exterior of the distal sheath 605, also as seen in FIG. 7A. The tube 705 has a flared proximal end 710 which engages the adapter 620 and a distal end 715. Optionally, the distal end 715 may be beveled, as shown in FIG. 7B. The tube 705 may serve at least two purposes. First, the length of the tube 705 limits the introduction of the sheath 605 to the exposed distal portion of the sheath 605, as seen in FIG. 7A. Second, the tube 705 can engage a pre-deployed puncture closure device disposed in the carotid artery wall, if present, to permit the sheath 605 to be withdrawn without dislodging the closure device.

The distal sheath 605 can be configured to establish a curved transition from a generally anterior-posterior approach over the common carotid artery to a generally axial luminal direction within the common carotid artery. The transition in direction is particularly useful when a percutaneous access is provided through the common carotid wall. While an open surgical access may allow for some distance in which to angle a straight sheath into the lumen of the common carotid artery, percutaneous access will generally be in a normal or perpendicular direction relative to the access of the lumen, and in such cases, a sheath that can flex or turn at an angle will find great use.

The sheath 605 can be formed in a variety of ways. For example, the sheath 605 can be pre-shaped to have a curve or an angle some set distance from the tip, typically 2 to 3 cm. The pre-shaped curve or angle can typically provide for a turn in the range from 20° to 90°, preferably from 30° to 70°. For initial introduction, the sheath 605 can be straightened with an obturator or other straight or shaped instrument such as the dilator 645 placed into its lumen. After the sheath 605 has been at least partially introduced through the percutaneous or other arterial wall penetration, the obturator can be withdrawn to allow the sheath 605 to reassume its pre-shaped configuration into the arterial lumen.

Other sheath configurations include having a deflection mechanism such that the sheath can be placed and the catheter can be deflected in situ to the desired deployment angle. In still other configurations, the catheter has a non-rigid configuration when placed into the lumen of the common carotid artery. Once in place, a pull wire or other stiffening mechanism can be deployed in order to shape and stiffen the sheath into its desired configuration. One particular example of such a mechanism is commonly known as "shape-lock" mechanisms as well described in medical and patent literature.

Another sheath configuration comprises a curved dilator inserted into a straight but flexible sheath, so that the dilator and sheath are curved during insertion. The sheath is flexible enough to conform to the anatomy after dilator removal.

In an embodiment, the sheath has built-in puncturing capability and atraumatic tip analogous to a guide wire tip. This eliminates the need for needle and wire exchange currently used for arterial access according to the micropuncture technique, and can thus save time, reduce blood loss, and require less surgeon skill.

FIG. 8A shows another embodiment of the arterial access device 110. This embodiment is substantially the same as the embodiment shown in FIG. 6A, except that the distal sheath 605 includes an occlusion element 129 for occluding flow through, for example the common carotid artery. If the occluding element 129 is an inflatable structure such as a balloon or the like, the sheath 605 can include an inflation lumen that communicates with the occlusion element 129. The occlusion element 129 can be an inflatable balloon, but it could also be an inflatable cuff, a conical or other circumferential element which flares outwardly to engage the interior wall of the common carotid artery to block flow therepast, a membrane-covered braid, a slotted tube that radially enlarges when axially compressed, or similar structure which can be deployed by mechanical means, or the like. In the case of balloon occlusion, the balloon can be compliant, non-compliant, elastomeric, reinforced, or have a variety of other characteristics. In an embodiment, the balloon is an elastomeric balloon which is closely received over the exterior of the distal end of the sheath prior to inflation. When inflated, the elastomeric balloon can expand and conform to the inner wall of the common carotid artery. In an embodiment, the elastomeric balloon is able to expand to a diameter at least twice that of the non-deployed configuration, frequently being able to be deployed to a diameter at least three times that of the undeployed configuration, more preferably being at least four times that of the undeployed configuration, or larger.

As shown in FIG. 8B, the distal sheath 605 with the occlusion element 129 can have a stepped or other configuration having a reduced diameter distal region 630. The distal region 630 can be sized for insertion into the carotid artery with the remaining proximal region of the sheath 605 having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm. The relatively short length of the reduced-diameter distal section 630 permits this section to be positioned in the common carotid artery CCA via the transcervical approach with reduced risk that the distal end of the sheath 605 will contact the bifurcation B.

FIG. 2B shows an alternative embodiment, wherein the occlusion element 129 can be introduced into the carotid artery on a second sheath 112 separate from the distal sheath 605 of the arterial access device 110. The second or "proximal" sheath 112 can be adapted for insertion into the common carotid artery in a proximal or "downward" direction away from the cerebral vasculature. The second, proximal sheath can include an inflatable balloon 129 or other occlusion element, generally as described above. The distal sheath 605 of the arterial access device 110 can be then placed into the common carotid artery distal of the second, proximal sheath and generally oriented in a distal direction toward the cerebral vasculature. By using separate occlusion and access sheaths, the size of the arteriotomy needed for introducing the access sheath can be reduced.

FIG. 2C shows yet another embodiment of a two arterial sheath system, wherein the interventional devices are introduced via an introducer sheath 114 separate from the distal sheath 605 of the arterial device 110. A second or "distal" sheath 114 can be adapted for insertion into the common carotid artery distal to the arterial access device 110. As with the previous embodiment, the use of two separate access sheaths allows the size of each arteriotomy to be reduced.

Venous Return Device

Figure 9:
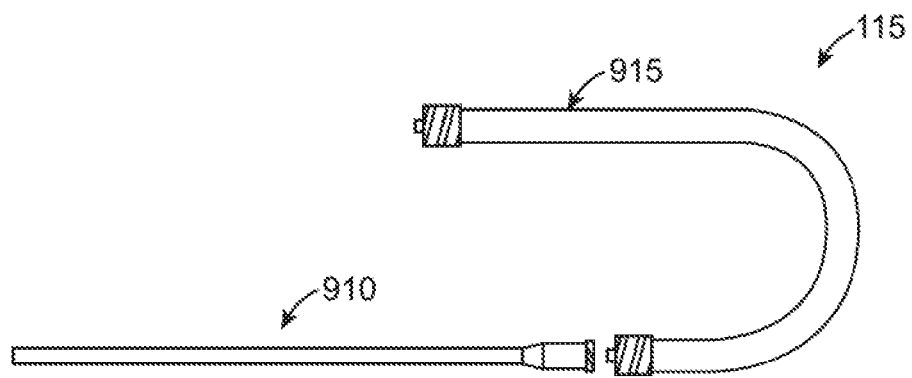
FIG. 9 illustrates a first embodiment of a venous return device useful in the methods and systems of the present disclosure.
Figure 10:
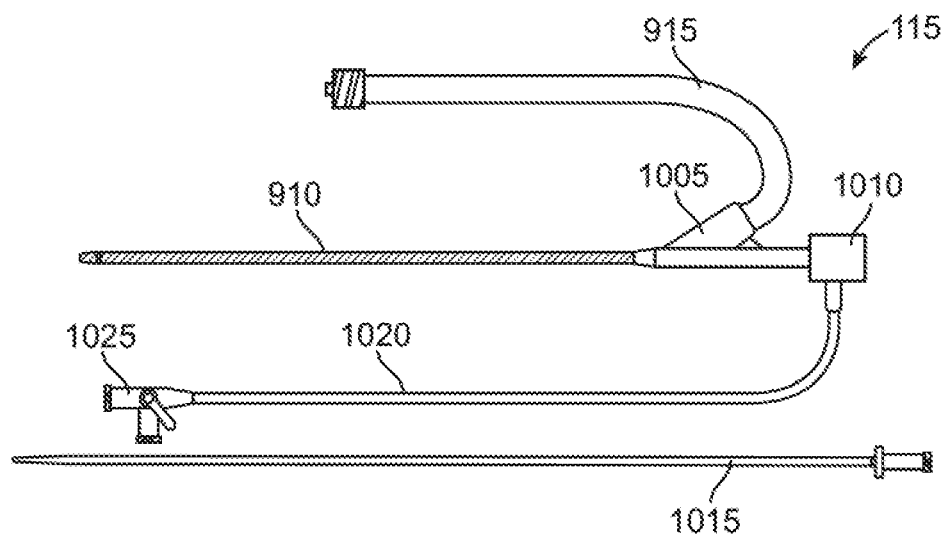
FIG. 10 illustrates an alternative venous return device useful in the methods and systems of the present disclosure.

Referring now to FIG. 9, the venous return device 115 can comprise a distal sheath 910 and a flow line 915, which connects to and forms a leg of the shunt 120 when the system is in use. The distal sheath 910 is adapted to be introduced through an incision or puncture into a venous return location, such as the jugular vein or femoral vein. The distal sheath 910 and flow line 915 can be permanently affixed, or can be attached using a conventional luer fitting, as shown in FIG. 9. Optionally, as shown in FIG. 10, the sheath 910 can be joined to the flow line 915 by a Y-connector 1005. The Y-connector 1005 can include a hemostasis valve 1010, permitting insertion of a dilator 1015 to facilitate introduction of the venous return device into the internal jugular vein or other vein. As with the arterial access dilator 645, the venous dilator 1015 includes a central guide wire lumen so the venous sheath and dilator combination can be placed over a guide wire. Optionally, the venous sheath 910 can include a flush line 1020 with a stopcock 1025 at its proximal or remote end.

In order to reduce the overall system flow resistance, the arterial access flow line 615 (FIG. 6A) and the venous return flow line 915, and Y-connectors 620 (FIG. 6A) and 1005, can each have a relatively large flow lumen inner diameter, typically being in the range from 2.54 mm (0.100 inch) to 5.08 mm (0.200 inch), and a relatively short length, typically being in the range from 10 cm to 20 cm. The low system flow resistance is desirable since it permits the flow to be maximized during portions of a procedure when the risk of emboli is at its greatest. The low system flow resistance also allows the use of a variable flow resistance for controlling flow in the system, as described in more detail below. The dimensions of the venous return sheath 910 can be generally the same as those described for the arterial access sheath 605 above. In the venous return sheath, an extension for the hemostasis valve 1010 is not required.

Retrograde Shunt

The shunt 120 can be formed of a single tube or multiple, connected tubes that provide fluid communication between the arterial access catheter 110 and the venous return catheter 115 to provide a pathway for retrograde blood flow therebetween. As shown in FIG. 1A, the shunt 120 connects at one end (via connector 127a) to the flow line 615 of the arterial access device 110, and at an opposite end (via connector 127b) to the flow line 915 of the venous return catheter 115.

In an embodiment, the shunt 120 can be formed of at least one tube that communicates with the flow control assembly 125. The shunt 120 can be any structure that provides a fluid pathway for blood flow. The shunt 120 can have a single lumen or it can have multiple lumens. The shunt 120 can be removably attached to the flow control assembly 125, arterial access device 110, and/or venous return device 115. Prior to use, the user can select a shunt 120 with a length that is most appropriate for use with the arterial access location and venous return location. In an embodiment, the shunt 120 can include one or more extension tubes that can be used to vary the length of the shunt 120. The extension tubes can be modularly attached to the shunt 120 to achieve a desired length. The modular aspect of the shunt 120 permits the user to lengthen the shunt 120 as needed depending on the site of venous return. For example, in some patients, the internal jugular vein IJV is small and/or tortuous. The risk of complications at this site may be higher than at some other locations, due to proximity to other anatomic structures. In addition, hematoma in the neck may lead to airway obstruction and/or cerebral vascular complications. Consequently, for such patients it may be desirable to locate the venous return site at a location other than the internal jugular vein IJV, such as the femoral vein. A femoral vein return site may be accomplished percutaneously, with lower risk of serious complication, and also offers an alternative venous access to the central vein if the internal jugular vein IJV is not available. Furthermore, the femoral venous return changes the layout of the reverse flow shunt such that the shunt controls may be located closer to the "working area" of the intervention, where the devices are being introduced and the contrast injection port is located.

In an embodiment, the shunt 120 has an internal diameter of 4.76 mm (3/16 inch) and has a length of 40-70 cm. As mentioned, the length of the shunt can be adjusted.

Flow Control Assembly—Regulation and Monitoring of Retrograde Flow

The flow control assembly 125 interacts with the retrograde shunt 120 to regulate and/or monitor the retrograde flow rate from the common carotid artery to the venous return site, such as the internal jugular vein, or to the external receptacle 130. In this regard, the flow control assembly 125 enables the user to achieve higher maximum flow rates than existing systems and to also selectively adjust, set, or otherwise modulate the retrograde flow rate. Various mechanisms can be used to regulate the retrograde flow rate, as described more fully below. The flow control assembly 125 enables the user to configure retrograde blood flow in a manner that is suited for various treatment regimens, as described below.

In general, the ability to control the continuous retrograde flow rate allows the physician to adjust the protocol for individual patients and stages of the procedure. The retrograde blood flow rate will typically be controlled over a range from a low rate to a high rate. The high rate can be at least two fold higher than the low rate, typically being at least three fold higher than the low rate, and often being at least five fold higher than the low rate, or even higher. In an embodiment, the high rate is at least three fold higher than the low rate and in another embodiment the high rate is at least six fold higher than the low rate. While it is generally desirable to have a high retrograde blood flow rate to maximize the extraction of emboli from the carotid arteries, the ability of patients to tolerate retrograde blood flow will vary. Thus, by having a system and protocol which allows the retrograde blood flow rate to be easily modulated, the treating physician can determine when the flow rate exceeds the tolerable level for that patient and set the reverse flow rate accordingly. For patients who cannot tolerate continuous high reverse flow rates, the physician can chose to turn on high flow only for brief, critical portions of the procedure when the risk of embolic debris is highest. At short intervals, for example between 15 seconds and 1 minute, patient tolerance limitations are usually not a factor.

In specific embodiments, the continuous retrograde blood flow rate can be controlled at a base line flow rate in the range from 10 ml/min to 200 ml/min, typically from 20 ml/min to 100 ml/min. These flow rates will be tolerable to the majority of patients. Although flow rate is maintained at the base line flow rate during most of the procedure, at times when the risk of emboli release is increased, the flow rate can be increased above the base line for a short duration in order to improve the ability to capture such emboli. For example, the retrograde blood flow rate can be increased above the base line when the stent catheter is being introduced, when the stent is being deployed, pre- and post-dilatation of the stent, removal of the common carotid artery occlusion, and the like.

The flow rate control system can be cycled between a relatively low flow rate and a relatively high flow rate in order to "flush" the carotid arteries in the region of the carotid bifurcation prior to reestablishing antegrade flow. Such cycling can be established with a high flow rate which can be approximately two to six fold greater than the low flow rate, typically being about three fold greater. The cycles can typically have a length in the range from 0.5 seconds to 10 seconds, usually from 2 seconds to 5 seconds, with the total duration of the cycling being in the range from 5 seconds to 60 seconds, usually from 10 seconds to 30 seconds.

Figure 11:
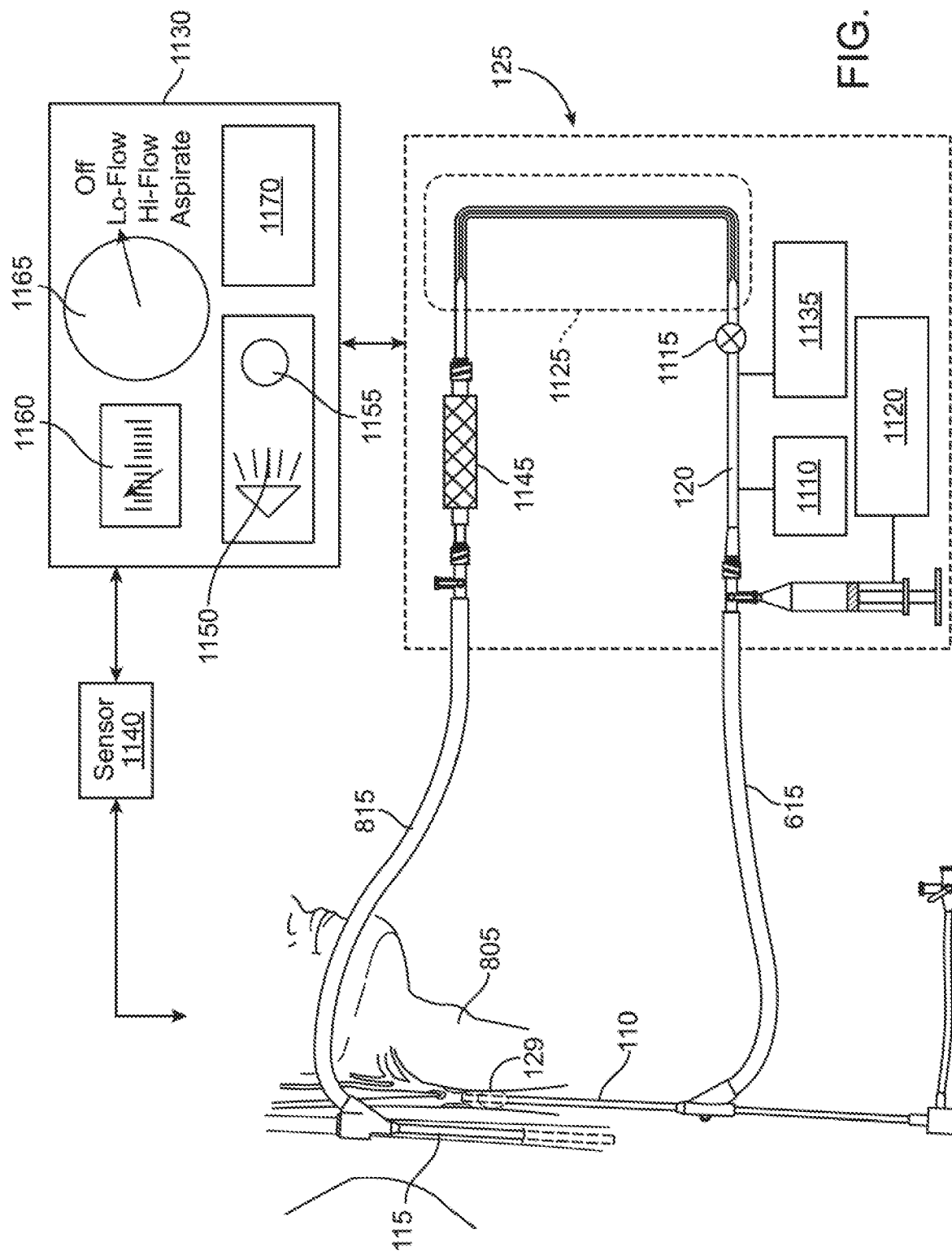
FIG. 11 illustrates the system of FIG. 1 including a flow control assembly.

FIG. 11 shows an example of the system 100 with a schematic representation of the flow control assembly 125, which is positioned along the shunt 120 such that retrograde blood flow passes through or otherwise communicates with at least a portion of the flow control assembly 125. The flow control assembly 125 can include various controllable mechanisms for regulating and/or monitoring retrograde flow. The mechanisms can include various means of controlling the retrograde flow, including one or more pumps 1110, valves 1115, syringes 1120 and/or a variable resistance component 1125. The flow control assembly 125 can be manually controlled by a user and/or automatically controlled via a controller 1130 to vary the flow through the shunt 120. For example, varying the flow resistance, the rate of retrograde blood flow through the shunt 120 can be controlled. The controller 1130, which is described in more detail below, can be integrated into the flow control assembly 125 or it can be a separate component that communicates with the components of the flow control assembly 125.

In addition, the flow control assembly 125 can include one or more flow sensors 1135 and/or anatomical data sensors 1140 (described in detail below) for sensing one or more aspects of the retrograde flow. A filter 1145 can be positioned along the shunt 120 for removing emboli before the blood is returned to the venous return site. When the filter 1145 is positioned upstream of the controller 1130, the filter 1145 can prevent emboli from entering the controller 1145 and potentially clogging the variable flow resistance component 1125. It should be appreciated that the various components of the flow control assembly 125 (including the pump 1110, valves 1115, syringes 1120, variable resistance component 1125, sensors 1135/1140, and filter 1145) can be positioned at various locations along the shunt 120 and at various upstream or downstream locations relative to one another.

The components of the flow control assembly 125 are not limited to the locations shown in FIG. 11. Moreover, the flow control assembly 125 does not necessarily include all of the components but can rather include various sub-combinations of the components. For example, a syringe could optionally be used within the flow control assembly 125 for purposes of regulating flow or it could be used outside of the assembly for purposes other than flow regulation, such as to introduce fluid such as radiopaque contrast into the artery in an antegrade direction via the shunt 120.

Both the variable resistance component 1125 and the pump 1110 can be coupled to the shunt 120 to control the retrograde flow rate. The variable resistance component 1125 controls the flow resistance, while the pump 1110 provides for positive displacement of the blood through the shunt 120. Thus, the pump can be activated to drive the retrograde flow rather than relying on the perfusion stump pressures of the ECA and ICA and the venous back pressure to drive the retrograde flow. The pump 1110 can be a peristaltic tube pump or any type of pump including a positive displacement pump. The pump 1110 can be activated and deactivated (either manually or automatically via the controller 1130) to selectively achieve blood displacement through the shunt 120 and to control the flow rate through the shunt 120. Displacement of the blood through the shunt 120 can also be achieved in other manners including using the aspiration syringe 1120, or a suction source such as a vacutainer, vaculock syringe, or wall suction may be used. The pump 1110 can communicate with the controller 1130.

One or more flow control valves 1115 can be positioned along the pathway of the shunt. The valve(s) can be manually actuated or automatically actuated (via the controller 1130). The flow control valves 1115 can be, for example one-way valves to prevent flow in the antegrade direction in the shunt 120, check valves, or high pressure valves which would close off the shunt 120, for example during high-pressure contrast injections (which are intended to enter the arterial vasculature in an antegrade direction).

The controller 1130 communicates with components of the system 100 including the flow control assembly 125 to enable manual and/or automatic regulation and/or monitoring of the retrograde flow through the components of the system 100 (including, for example, the shunt 120, the arterial access device 110, the venous return device 115 and the flow control assembly 125). For example, a user can actuate one or more actuators on the controller 1130 to manually control the components of the flow control assembly 125. Manual controls can include switches or dials or similar components located directly on the controller 1130 or components located remote from the controller 1130 such as a foot pedal or similar device. The controller 1130 can also automatically control the components of the system 100 without requiring input from the user. In an embodiment, the user can program software in the controller 1130 to enable such automatic control. The controller 1130 can control actuation of the mechanical portions of the flow control assembly 125. The controller 1130 can include circuitry or programming that interprets signals generated by sensors 1135/1140 such that the controller 1130 can control actuation of the flow control assembly 125 in response to such signals generated by the sensors.

The representation of the controller 1130 in FIG. 11 is merely exemplary. It should be appreciated that the controller 1130 can vary in appearance and structure. The controller 1130 is shown in FIG. 11 as being integrated in a single housing. This permits the user to control the flow control assembly 125 from a single location. It should be appreciated that any of the components of the controller 1130 can be separated into separate housings. Further, FIG. 11 shows the controller 1130 and flow control assembly 125 as separate housings. It should be appreciated that the controller 1130 and flow control regulator 125 can be integrated into a single housing or can be divided into multiple housings or components.

Flow State Indicator(s)

The controller 1130 can include one or more indicators that provides a visual and/or audio signal to the user regarding the state of the retrograde flow. An audio indication advantageously reminds the user of a flow state without requiring the user to visually check the flow controller 1130. The indicator(s) can include a speaker 1150 and/or a light 1155 or any other means for communicating the state of retrograde flow to the user. The controller 1130 can communicate with one or more sensors of the system to control activation of the indicator. Or, activation of the indicator can be tied directly to the user actuating one of the flow control actuators 1165. The indicator need not be a speaker or a light. The indicator could simply be a button or switch that visually indicates the state of the retrograde flow. For example, the button being in a certain state (such as a pressed or down state) may be a visual indication that the retrograde flow is in a high state. Or, a switch or dial pointing toward a particular labeled flow state may be a visual indication that the retrograde flow is in the labeled state.

The indicator can provide a signal indicative of one or more states of the retrograde flow. In an embodiment, the indicator identifies only two discrete states: a state of "high" flow rate and a state of "low" flow rate. In another embodiment, the indicator identifies more than two flow rates, including a "high" flow rate, a "medium" flow rate, and a "low" rate. The indicator can be configured to identify any quantity of discrete states of the retrograde flow or it can identify a graduated signal that corresponds to the state of the retrograde flow. In this regard, the indicator can be a digital or analog meter 1160 that indicates a value of the retrograde flow rate, such as in ml/min or any other units.

In an embodiment, the indicator is configured to indicate to the user whether the retrograde flow rate is in a state of "high" flow rate or a "low" flow rate. For example, the indicator may illuminate in a first manner (e.g., level of brightness) and/or emit a first audio signal when the flow rate is high and then change to a second manner of illumination and/or emit a second audio signal when the flow rate is low. Or, the indicator may illuminate and/or emit an audio signal only when the flow rate is high, or only when the flow rate is low. Given that some patients may be intolerant of a high flow rate or intolerant of a high flow rate beyond an extended period of time, it can be desirable that the indicator provide notification to the user when the flow rate is in the high state. This would serve as a fail safe feature.

In another embodiment, the indicator provides a signal (audio and/or visual) when the flow rate changes state, such as when the flow rate changes from high to low and/or vice-versa. In another embodiment, the indicator provides a signal when no retrograde flow is present, such as when the shunt 120 is blocked or one of the stopcocks in the shunt 120 is closed.

Flow Rate Actuators

The controller 1130 can include one or more actuators that the user can press, switch, manipulate, or otherwise actuate to regulate the retrograde flow rate and/or to monitor the flow rate. For example, the controller 1130 can include a flow control actuator 1165 (such as one or more buttons, knobs, dials, switches, etc.) that the user can actuate to cause the controller to selectively vary an aspect of the reverse flow. For example, in the illustrated embodiment, the flow control actuator 1165 is a knob that can be turned to various discrete positions each of which corresponds to the controller 1130 causing the system 100 to achieve a particular retrograde flow state. The states include, for example, (a) OFF; (b) LO-FLOW; (c) HI-FLOW; and (d) ASPIRATE. It should be appreciated that the foregoing states are merely exemplary and that different states or combinations of states can be used. The controller 1130 achieves the various retrograde flow states by interacting with one or more components of the system, including the sensor(s), valve(s), variable resistance component, and/or pump(s). It should be appreciated that the controller 1130 can also include circuitry and software that regulates the retrograde flow rate and/or monitors the flow rate such that the user wouldn't need to actively actuate the controller 1130.

The OFF state corresponds to a state where there is no retrograde blood flow through the shunt 120. When the user sets the flow control actuator 1165 to OFF, the controller 1130 causes the retrograde flow to cease, such as by shutting off valves or closing a stop cock in the shunt 120. The LO-FLOW and HI-FLOW states correspond to a low retrograde flow rate and a high retrograde flow rate, respectively. When the user sets the flow control actuator 1165 to LO-FLOW or HI-FLOW, the controller 1130 interacts with components of the flow control regulator 125 including pump(s) 1110, valve(s) 1115 and/or variable resistance component 1125 to increase or decrease the flow rate accordingly. Finally, the ASPIRATE state corresponds to opening the circuit to a suction source, for example a vacutainer or suction unit, if active retrograde flow is desired.

The system can be used to vary the blood flow between various states including an active state, a passive state, an aspiration state, and an off state. The active state corresponds to the system using a means that actively drives retrograde blood flow. Such active means can include, for example, a pump, syringe, vacuum source, etc. The passive state corresponds to when retrograde blood flow is driven by the perfusion stump pressures of the ECA and ICA and possibly the venous pressure. The aspiration state corresponds to the system using a suction source, for example a vacutainer or suction unit, to drive retrograde blood flow. The off state corresponds to the system having zero retrograde blood flow such as the result of closing a stopcock or valve. The low and high flow rates can be either passive or active flow states. In an embodiment, the particular value (such as in ml/min) of either the low flow rate and/or the high flow rate can be predetermined and/or pre-programmed into the controller such that the user does not actually set or input the value. Rather, the user simply selects "high flow" and/or "low flow" (such as by pressing an actuator such as a button on the controller 1130) and the controller 1130 interacts with one or more of the components of the flow control assembly 125 to cause the flow rate to achieve the predetermined high or low flow rate value. In another embodiment, the user sets or inputs a value for low flow rate and/or high flow rate such as into the controller. In another embodiment, the low flow rate and/or high flow rate is not actually set. Rather, external data (such as data from the anatomical data sensor 1140) is used as the basis for affects the flow rate.

The flow control actuator 1165 can be multiple actuators, for example one actuator, such as a button or switch, to switch state from LO-FLOW to HI-FLOW and another to close the flow loop to OFF, for example during a contrast injection where the contrast is directed antegrade into the carotid artery. In an embodiment, the flow control actuator 1165 can include multiple actuators. For example, one actuator can be operated to switch flow rate from low to high, another actuator can be operated to temporarily stop flow, and a third actuator (such as a stopcock) can be operated for aspiration using a syringe. In another example, one actuator is operated to switch to LO-FLOW and another actuator is operated to switch to HI-FLOW. Or, the flow control actuator 1165 can include multiple actuators to switch states from LO-FLOW to HI-FLOW and additional actuators for fine-tuning flow rate within the high flow state and low flow state. Upon switching between LO-FLOW and HI-FLOW, these additional actuators can be used to fine-tune the flow rates within those states. Thus, it should be appreciated that within each state (i.e. high flow state and low flow states) a variety of flow rates can be dialed in and fine-tuned. A wide variety of actuators can be used to achieve control over the state of flow.

The controller 1130 or individual components of the controller 1130 can be located at various positions relative to the patient and/or relative to the other components of the system 100. For example, the flow control actuator 1165 can be located near the hemostasis valve where any interventional tools are introduced into the patient in order to facilitate access to the flow control actuator 1165 during introduction of the tools. The location may vary, for example, based on whether a transfemoral or a transcervical approach is used, as shown in FIGS. 1 A-C. The controller 1130 can have a wireless connection to the remainder of the system 100 and/or a wired connection of adjustable length to permit remote control of the system 100. The controller 1130 can have a wireless connection with the flow control regulator 125 and/or a wired connection of adjustable length to permit remote control of the flow control regulator 125. The controller 1130 can also be integrated in the flow control regulator 125. Where the controller 1130 is mechanically connected to the components of the flow control assembly 125, a tether with mechanical actuation capabilities can connect the controller 1130 to one or more of the components. In an embodiment, the controller 1130 can be positioned a sufficient distance from the system 100 to permit positioning the controller 1130 outside of a radiation field when fluoroscopy is in use.

The controller 1130 and any of its components can interact with other components of the system (such as the pump(s), sensor(s), shunt, etc) in various manners. For example, any of a variety of mechanical connections can be used to enable communication between the controller 1130 and the system components. Alternately, the controller 1130 can communicate electronically or magnetically with the system components. Electro-mechanical connections can also be used. The controller 1130 can be equipped with control software that enables the controller to implement control functions with the system components. The controller itself can be a mechanical, electrical or electro-mechanical device. The controller can be mechanically, pneumatically, or hydraulically actuated or electromechanically actuated (for example in the case of solenoid actuation of flow control state). The controller 1130 can include a computer, computer processor, and memory, as well as data storage capabilities.

Sensor(s)

As mentioned, the flow control assembly 125 can include or interact with one or more sensors, which communicate with the system 100 and/or communicate with the patient's anatomy. Each of the sensors can be adapted to respond to a physical stimulus (including, for example, heat, light, sound, pressure, magnetism, motion, etc.) and to transmit a resulting signal for measurement or display or for operating the controller 1130. In an embodiment, the flow sensor 1135 interacts with the shunt 120 to sense an aspect of the flow through the shunt 120, such as flow velocity or volumetric rate of blood flow. The flow sensor 1135 could be directly coupled to a display that directly displays the value of the volumetric flow rate or the flow velocity. Or the flow sensor 1135 could feed data to the controller 1130 for display of the volumetric flow rate or the flow velocity.

The type of flow sensor 1135 can vary. The flow sensor 1135 can be a mechanical device, such as a paddle wheel, flapper valve, rolling ball, or any mechanical component that responds to the flow through the shunt 120. Movement of the mechanical device in response to flow through the shunt 120 can serve as a visual indication of fluid flow and can also be calibrated to a scale as a visual indication of fluid flow rate. The mechanical device can be coupled to an electrical component. For example, a paddle wheel can be positioned in the shunt 120 such that fluid flow causes the paddle wheel to rotate, with greater rate of fluid flow causing a greater speed of rotation of the paddle wheel. The paddle wheel can be coupled magnetically to a Hall-effect sensor to detect the speed of rotation, which is indicative of the fluid flow rate through the shunt 120.

In an embodiment, the flow sensor 1135 is an ultrasonic or electromagnetic flow meter, which allows for blood flow measurement without contacting the blood through the wall of the shunt 120. An ultrasonic or electromagnetic flow meter can be configured such that it does not have to contact the internal lumen of the shunt 120. In an embodiment, the flow sensor 1135 at least partially includes a Doppler flow meter, such as a Transonic flow meter, that measures fluid flow through the shunt 120. It should be appreciated that any of a wide variety of sensor types can be used including an ultrasound flow meter and transducer. Moreover, the system can include multiple sensors.

The system 100 is not limited to using a flow sensor 1135 that is positioned in the shunt 120 or a sensor that interacts with the venous return device 115 or the arterial access device 110. For example, an anatomical data sensor 1140 can communicate with or otherwise interact with the patient's anatomy such as the patient's neurological anatomy. In this manner, the anatomical data sensor 1140 can sense a measurable anatomical aspect that is directly or indirectly related to the rate of retrograde flow from the carotid artery. For example, the anatomical data sensor 1140 can measure blood flow conditions in the brain, for example the flow velocity in the middle cerebral artery, and communicate such conditions to a display and/or to the controller 1130 for adjustment of the retrograde flow rate based on predetermined criteria. In an embodiment, the anatomical data sensor 1140 comprises a transcranial Doppler ultrasonography (TCD), which is an ultrasound test that uses reflected sound waves to evaluate blood as it flows through the brain. Use of TCD results in a TCD signal that can be communicated to the controller 1130 for controlling the retrograde flow rate to achieve or maintain a desired TCD profile. The anatomical data sensor 1140 can be based on any physiological measurement, including reverse flow rate, blood flow through the middle cerebral artery, TCD signals of embolic particles, or other neuromonitoring signals.

In an embodiment, the system 100 comprises a closed-loop control system. In the closed-loop control system, one or more of the sensors (such as the flow sensor 1135 or the anatomical data sensor 1140) senses or monitors a predetermined aspect of the system 100 or the anatomy (such as, for example, reverse flow rate and/or neuromonitoring signal). The sensor(s) feed relevant data to the controller 1130, which continuously adjusts an aspect of the system as necessary to maintain a desired retrograde flow rate. The sensors communicate feedback on how the system 100 is operating to the controller 1130 so that the controller 1130 can translate that data and actuate the components of the flow control regulator 125 to dynamically compensate for disturbances to the retrograde flow rate. For example, the controller 1130 may include software that causes the controller 1130 to signal the components of the flow control assembly 125 to adjust the flow rate such that the flow rate is maintained at a constant state despite differing blood pressures from the patient. In this embodiment, the system 100 need not rely on the user to determine when, how long, and/or what value to set the reverse flow rate in either a high or low state. Rather, software in the controller 1130 can govern such factors. In the closed loop system, the controller 1130 can control the components of the flow control assembly 125 to establish the level or state of retrograde flow (either analog level or discreet state such as high, low, baseline, medium, etc.) based on the retrograde flow rate sensed by the sensor 1135.

In an embodiment, the anatomical data sensor 1140 (which measures a physiologic measurement in the patient) communicates a signal to the controller 1130, which adjusts the flow rate based on the signal. For example the physiological measurement may be based on flow velocity through the MCA, TCD signal, or some other cerebral vascular signal. In the case of the TCD signal, TCD may be used to monitor cerebral flow changes and to detect microemboli. The controller 1130 may adjust the flow rate to maintain the TCD signal within a desired profile. For example, the TCD signal may indicate the presence of microemboli ("TCD hits") and the controller 1130 can adjust the retrograde flow rate to maintain the TCD hits below a threshold value of hits. (See, Ribo, et al., "Transcranial Doppler Monitoring of Transcervical Carotid Stenting with Flow Reversal Protection: A Novel Carotid Revascularization Technique", *Stroke* 2006, 37, 2846-2849; Shekel, et al., "Experience of 500 Cases of Neurophysiological Monitoring in Carotid Endarterectomy", *Acta Neurochir*, 2007, 149:681-689, which are incorporated by reference in their entirety.

In the case of the MCA flow, the controller 1130 can set the retrograde flow rate at the "maximum" flow rate that is tolerated by the patient, as assessed by perfusion to the brain. The controller 1130 can thus control the reverse flow rate to optimize the level of protection for the patient without relying on the user to intercede. In another embodiment, the feedback is based on a state of the devices in the system 100 or the interventional tools being used. For example, a sensor may notify the controller 1130 when the system 100 is in a high risk state, such as when an interventional catheter is positioned in the sheath 605. The controller 1130 then adjusts the flow rate to compensate for such a state.

The controller 1130 can be used to selectively augment the retrograde flow in a variety of manners. For example, it has been observed that greater reverse flow rates may cause a resultant greater drop in blood flow to the brain, most importantly the ipsilateral MCA, which may not be compensated enough with collateral flow from the Circle of Willis. Thus a higher reverse flow rate for an extended period of time may lead to conditions where the patient's brain is not getting enough blood flow, leading to patient intolerance as exhibited by neurologic symptoms. Studies show that MCA blood velocity less than 10 cm/sec is a threshold value below which patient is at risk for neurological blood deficit. There are other markers for monitoring adequate perfusion to the brains, such as EEG signals. However, a high flow rate may be tolerated even up to a complete stoppage of MCA flow for a short period, up to about 15 seconds to 1 minute.

Thus, the controller 1130 can optimize embolic debris capture by automatically increasing the reverse flow only during limited time periods which correspond to periods of heightened risk of emboli generation during a procedure. These periods of heightened risk include the period of time while an interventional device (such as a dilatation balloon for pre or post stenting dilatation or a stent delivery device) crosses the plaque P. Another period is during an interventional maneuver such as deployment of the stent or inflation and deflation of the balloon pre- or post-dilatation. A third period is during injection of contrast for angiographic imaging of treatment area. During lower risk periods, the controller can cause the reverse flow rate to revert to a lower, baseline level. This lower level may correspond to a low reverse flow rate in the ICA, or even slight antegrade flow in those patients with a high ECA to ICA perfusion pressure ratio.

In a flow regulation system where the user manually sets the state of flow, there is risk that the user may not pay attention to the state of retrograde flow (high or low) and accidentally keep the circuit on high flow. This may then lead to adverse patient reactions. In an embodiment, as a safety mechanism, the default flow rate is the low flow rate. This serves as a fail safe measure for patient's that are intolerant of a high flow rate. In this regard, the controller 1130 can be biased toward the default rate such that the controller causes the system to revert to the low flow rate after passage of a predetermined period of time of high flow rate. The bias toward low flow rate can be achieved via electronics or software, or it can be achieved using mechanical components, or a combination thereof. In an embodiment, the flow control actuator 1165 of the controller 1130 and/or valve(s) 1115 and/or pump(s) 1110 of the flow control regulator 125 are spring loaded toward a state that achieves a low flow rate. The controller 1130 is configured such that the user may over-ride the controller 1130 such as to manually cause the system to revert to a state of low flow rate if desired.

In another safety mechanism, the controller 1130 includes a timer 1170 (FIG. 11) that keeps time with respect to how long the flow rate has been at a high flow rate. The controller 1130 can be programmed to automatically cause the system 100 to revert to a low flow rate after a predetermined time period of high flow rate, for example after 15, 30, or 60 seconds or more of high flow rate. After the controller reverts to the low flow rate, the user can initiate another predetermined period of high flow rate as desired. Moreover, the user can override the controller 1130 to cause the system 100 to move to the low flow rate (or high flow rate) as desired.

In an exemplary procedure, embolic debris capture is optimized while not causing patient tolerance issues by initially setting the level of retrograde flow at a low rate, and then switching to a high rate for discreet periods of time during critical stages in the procedure. Alternately, the flow rate is initially set at a high rate, and then verifying patient tolerance to that level before proceeding with the rest of the procedure. If the patient shows signs of intolerance, the retrograde flow rate is lowered. Patient tolerance may be determined automatically by the controller based on feedback from the anatomical data sensor 1140 or it may be determined by a user based on patient observation. The adjustments to the retrograde flow rate may be performed automatically by the controller or manually by the user. Alternately, the user may monitor the flow velocity through the middle cerebral artery (MCA), for example using TCD, and then to set the maximum level of reverse flow which keeps the MCA flow velocity above the threshold level. In this situation, the entire procedure may be done without modifying the state of flow. Adjustments may be made as needed if the MCA flow velocity changes during the course of the procedure, or the patient exhibits neurologic symptoms.

Exemplary Mechanisms to Regulate Flow

The system 100 is adapted to regulate retrograde flow in a variety of manners. Any combination of the pump 1110, valve 1115, syringe 1120, and/or variable resistance component 1125 can be manually controlled by the user or automatically controlled via the controller 1130 to adjust the retrograde flow rate. Thus, the system 100 can regulate retrograde flow in various manners, including controlling an active flow component (e.g., pump, syringe, etc.), reducing the flow restriction, switching to an aspiration source (such as a pre-set VacLock syringe, Vacutainer, suction system, or the like), or any combination thereof.

In the situation of FIG. 1D where an external receptacle or reservoir is used, the retrograde flow may be augmented in various manners. The reservoir has a head height comprised of the height of the blood inside the reservoir and the height of the reservoir with respect to the patient. Reverse flow into the reservoir may be modulated by setting the reservoir height to increase or decrease the amount of pressure gradient from the CCA to the reservoir. In an embodiment, the reservoir is raised to increase the reservoir pressure to a pressure that is greater than venous pressure. Or, the reservoir can be positioned below the patient, such as down to a level of the floor, to lower the reservoir pressure to a pressure below venous or atmospheric pressure.

The variable flow resistance in shunt 120 may be provided in a wide variety of ways. In this regard, flow resistance component 1125 can cause a change in the size or shape of the shunt to vary flow conditions and thereby vary the flow rate. Or, the flow resistance component 1125 can re-route the blood flow through one or more alternate flow pathways in the shunt to vary the flow conditions. Some exemplary embodiments of the flow resistance component 1125 are now described.

As shown in FIGS. 12A, 12B, 12C, and 12D, in an embodiment the shunt 120 has an inflatable bladder 1205 formed along a portion of its interior lumen. As shown in FIGS. 12A and 12C, when the bladder 1205 is deflated, the inner lumen of the shunt 120 remains substantially unrestricted, providing for a low resistance flow. By inflating the bladder 1205, however, as shown in FIGS. 12B and 12D, the flow lumen can be greatly restricted, thus greatly increasing the flow resistance and reducing the flow rate of atrial blood to the venous vasculature. The controller 1130 can control inflation/deflation of the bladder 1205 or it can be controlled manually by the user.

Rather than using an inflatable internal bladder, as shown in FIGS. 12A-12D, the cross-sectional area of the lumen in the shunt 120 may be decreased by applying an external force, such as flattening the shunt 120 with a pair of opposed plates 1405, as shown in FIGS. 13A-13D. The opposed plates are adapted to move toward and away from one another with the shunt 120 positioned between the plates. When the plates 1405 are spaced apart, as shown in FIGS. 13A and 13C, the lumen of the shunt 120 remains unrestricted. When the plates 1405 are closed on the shunt 120, as shown in FIGS. 13B and 13D, in contrast, the plates 1405 constrict the shunt 120. In this manner, the lumen remaining in shunt 120 can be greatly decreased to increase flow resistance through the shunt. The controller 1130 can control movement of the plates 1405 or such movement can be controlled manually by the user.

Referring now to FIGS. 14A and 14B, the available cross-sectional area of the shunt 120 can also be restricted by axially elongating a portion 1505 of the shunt 120. Prior to axial elongation, the portion 1505 will be generally unchanged, providing a full luminal flow area in the portion 1505, as shown in FIG. 14A. By elongating the portion 1505, however, as shown in FIG. 14B, the internal luminal area of the shunt 120 in the portion 1505 can be significantly decreased and the length increased, both of which have the effect of increasing the flow resistance. When employing axial elongation to reduce the luminal area of shunt 120, it will be advantageous to employ a mesh or braid structure in the shunt at least in the portion 1505. The mesh or braid structure provides the shunt 120 with a pliable feature that facilitates axial elongation without breaking. The controller 1130 can control elongation of the shunt 120 or such it can be controlled manually by the user.

Referring now to FIGS. 15A-15D, instead of applying an external force to reduce the cross-sectional area of shunt 120, a portion of the shunt 120 can be made with a small diameter to begin with, as shown in FIGS. 15A and 15C. The shunt 120 passes through a chamber 1600 which is sealed at both ends. A vacuum is applied within the chamber 1600 exterior of the shunt 120 to cause a pressure gradient. The pressure gradient cause the shunt 120 to increase in size within the chamber 120, as shown in FIGS. 12B and 12D. The vacuum may be applied in a receptacle 1605 attached to a vacuum source 1610. Conversely, a similar system may be employed with a shunt 120 whose resting configuration is in the increased size. Pressure may be applied to the chamber to shrink or flatten the shunt to decrease the flow resistance. The controller 1130 can control the vacuum or it can be controlled manually by the user.

Figure 16A:
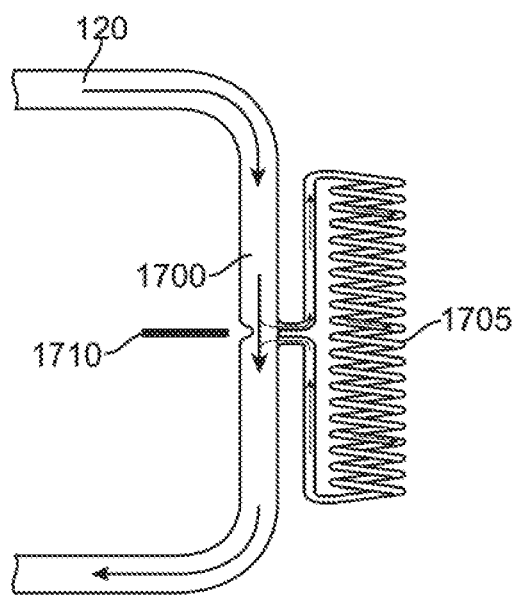
Figure 16B:
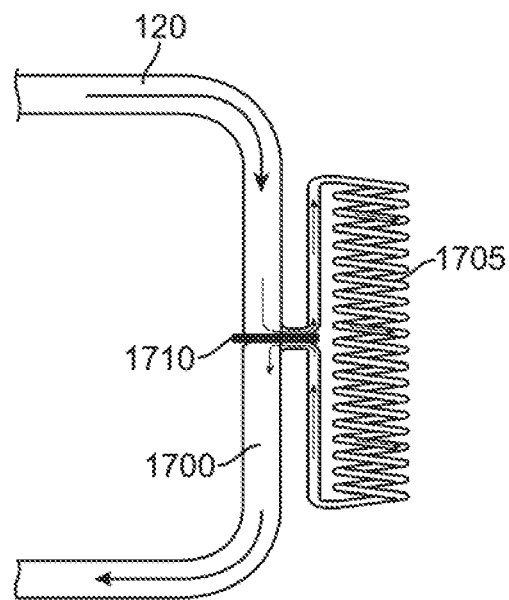

As yet another alternative, the flow resistance through shunt 120 may be changed by providing two or more alternative flow paths. As shown in FIG. 16A, the flow through shunt 120 passes through a main lumen 1700 as well as secondary lumen 1705. The secondary lumen 1705 is longer and/or has a smaller diameter than the main lumen 1700. Thus, the secondary lumen 1705 has higher flow resistance than the main lumen 1700. By passing the blood through both these lumens, the flow resistance will be at a minimum. Blood is able to flow through both lumens 1700 and 1705 due to the pressure drop created in the main lumen 1700 across the inlet and outlet of the secondary lumen 1705. This has the benefit of preventing stagnant blood. As shown in FIG. 16B, by blocking flow through the main lumen 1700 of shunt 120, the flow can be diverted entirely to the secondary lumen 1705, thus increasing the flow resistance and reducing the blood flow rate. It will be appreciated that additional flow lumens could also be provided in parallel to allow for a three, four, or more discrete flow resistances. The shunt 120 may be equipped with a valve 1710 that controls flow to the main lumen 1700 and the secondary lumen 1705 with the valve 1710 being controlled by the controller 1130 or being controlled manually by the user. The embodiment of FIGS. 16A and 16B has an advantage in that this embodiment in that it does not require as small of lumen sizes to achieve desired retrograde flow rates as some of the other embodiments of variable flow resistance mechanisms. This is a benefit in blood flow lines in that there is less chance of clogging and causing clots in larger lumen sizes than smaller lumen sizes.

Figure 17A:
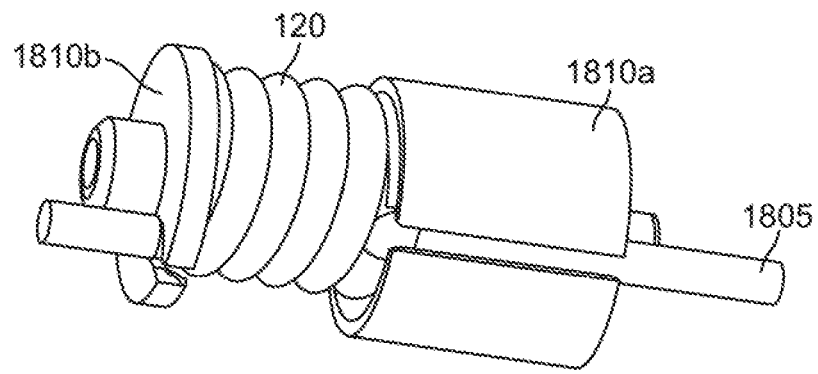
FIGS. 17A-17B, FIGS. 18A-18B, FIGS. 19A-19D, and FIGS. 20A-20B illustrate further embodiments of a variable flow resistance system useful in the methods and systems of the present disclosure.
Figure 17B:
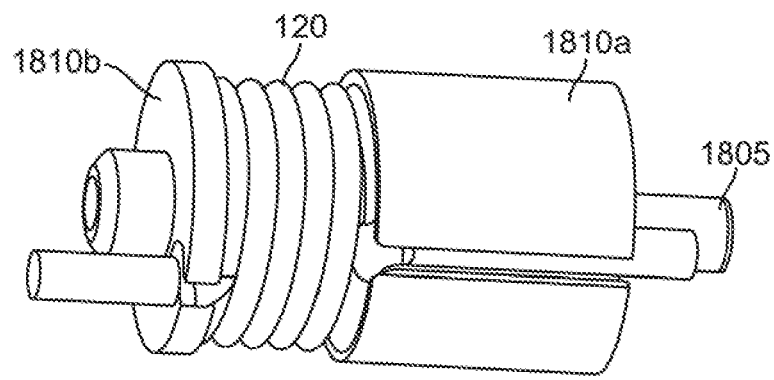

The shunt 120 can also be arranged in a variety of coiled configurations which permit external compression to vary the flow resistance in a variety of ways. Arrangement of a portion of the shunt 120 in a coil contains a long section of the shunt in a relatively small area. This allows compression of a long length of the shunt 120 over a small space. As shown in FIGS. 17A and 17B, a portion of the shunt 120 is wound around a dowel 1805 to form a coiled region. The dowel 1805 has plates 1810a and 1810b which can move toward and away from each other in an axial direction. When plates 1810a and 1810b are moved away from each other, the coiled portion of the shunt 105 is uncompressed and flow resistance is at a minimum. The shunt 120 is large diameter, so when the shunt is non-compressed, the flow resistance is low, allowing a high-flow state. To down-regulate the flow, the two plates 1810a and 1810b are pushed together, compressing the coil of shunt 120. By moving the plates 1810a and 1810b together, as shown in FIG. 17B, the coiled portion of the shunt 120 is compressed to increase the flow resistance. The controller 1130 can control the plates or they can be controlled manually by the user.

Figure 18A:
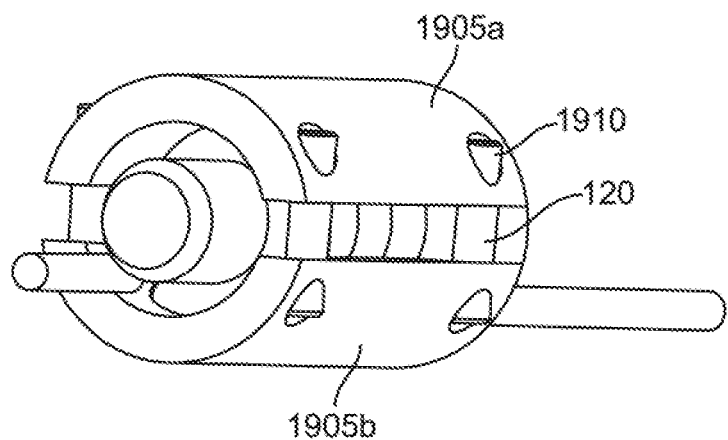
Figure 18B:
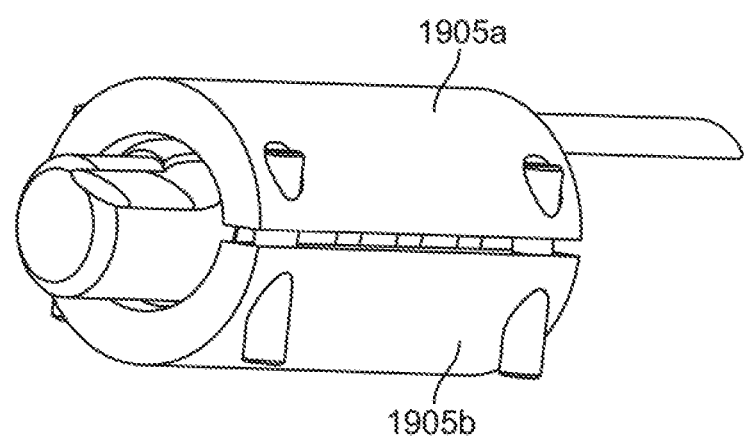

A similar compression apparatus is shown in FIGS. 18A and 18B. In this configuration, the coiled shunt 120 is encased between two movable cylinder halves 1905a and 1905b. The halves 1905a and 1905b can slide along dowel pins 1910 to move toward and away from one another. When the cylinder halves 1905 are moved apart, the coiled shunt 120 is uncompressed and flow resistance is at a minimum. When the cylinder halves 1905 are brought together, the coiled shunt 120 is compressed circumferentially to increase flow resistance. The controller 1130 can control the halves 1905 or they can be controlled manually by the user.

Figure 19A:
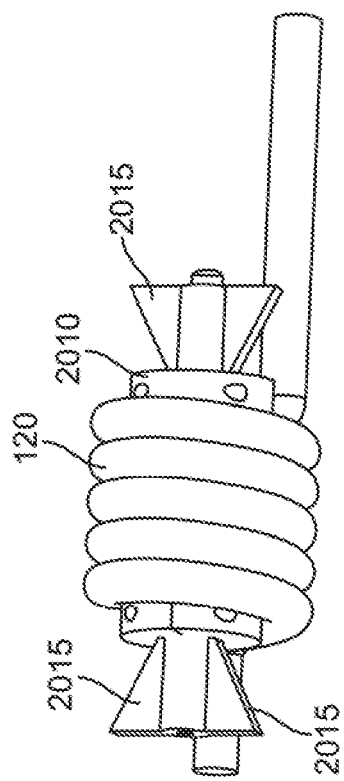
Figure 19C:
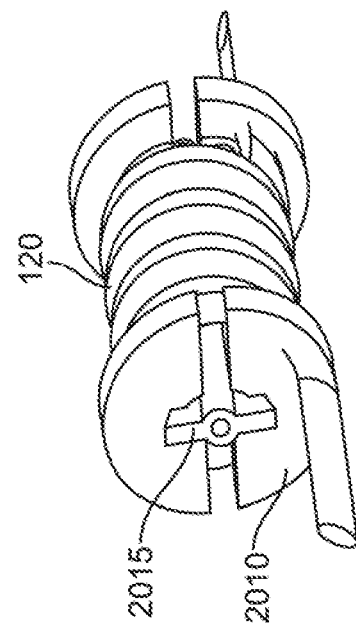
Figure 19B:
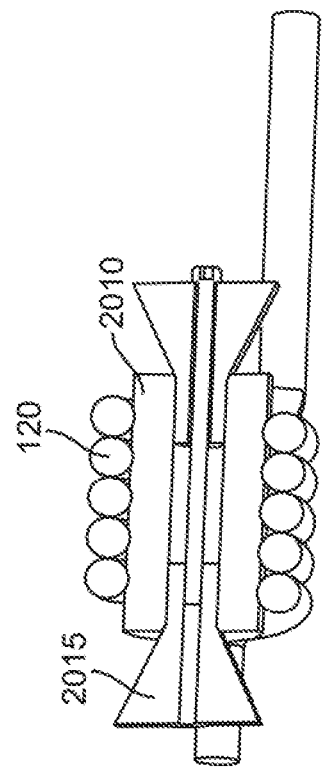
Figure 19D:
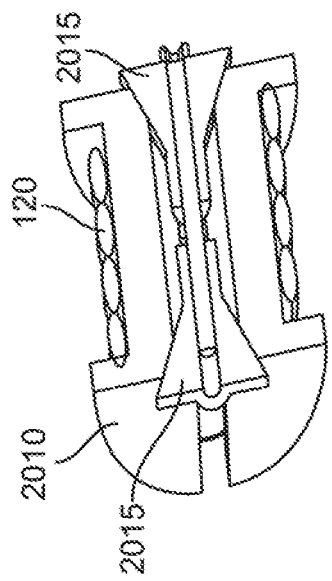

As shown in FIGS. 19A through 19D, the shunt 120 may also be wound around an axially split mandrel 2010 having wedge elements 2015 on opposed ends. By axially translating wedge elements 2015 in and out of the split mandrel 2010, the split portions of the mandrel are opened and closed relative to one another, causing the coil of tubing to be stretched (when the mandrel portions 2010 are spread apart, FIG. 19C, 19D) or relaxed (when the mandrel portions 2010 are closed, FIG. 19A, 19B.) Thus, when the wedge elements 2015 are spaced apart, as shown in FIGS. 19A and 19B, the outward pressure on the shunt 120 is at a minimum and the flow resistance is also at a minimum. By driving the wedge elements 2015 inwardly, as shown in FIG. 19C and 19D, the split mandrel halves 2020 are forced apart and the coil of shunt 120 is stretched. This has the dual effect of decreasing the cross sectional area of the shunt and lengthening the shunt in the coiled region, both of which lead to increased flow resistance.

Figure 20A:
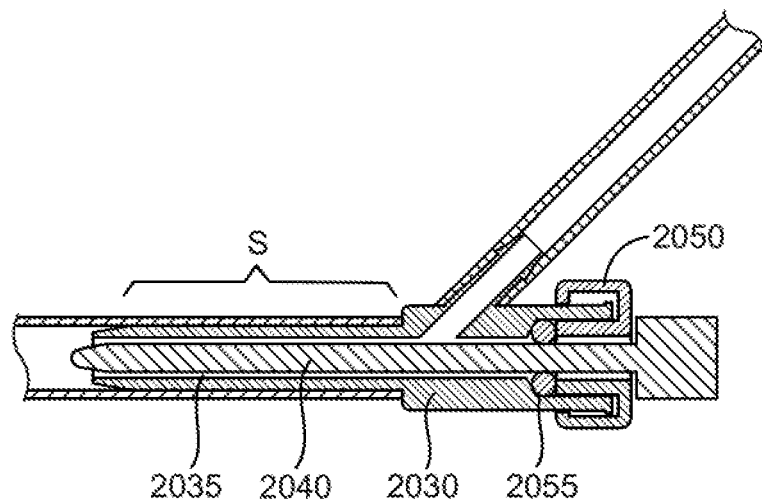
Figure 20B:
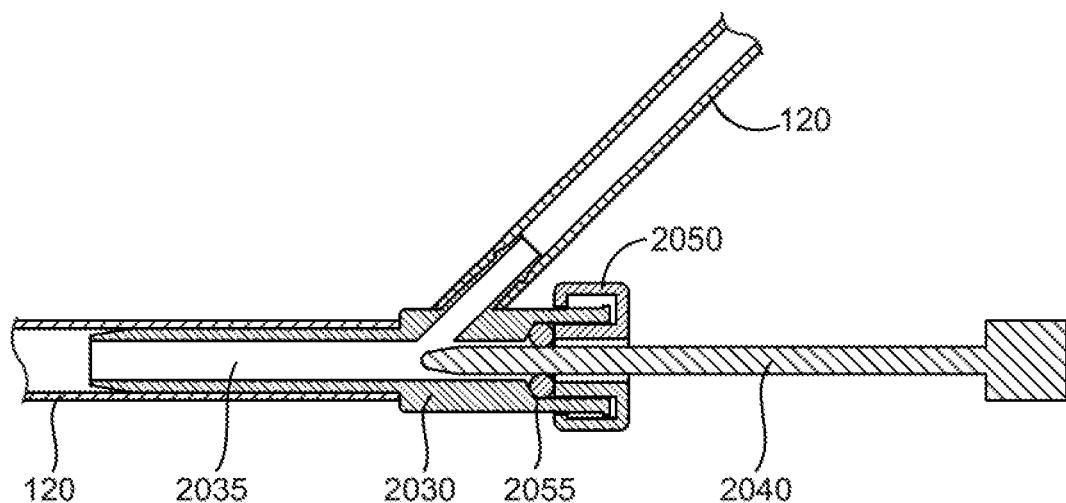

FIGS. 20A and 20B show an embodiment of the variable resistance component 1125 that uses a dowel to vary the resistance to flow. A housing 2030 is inserted into a section of the shunt 120. The housing 2030 has an internal lumen 2035 that is contiguous with the internal lumen of the shunt 120. A dowel 2040 can move into and out of a portion of the internal lumen 2035. As shown in FIG. 20A, when the dowel 2040 is inserted into the internal lumen 2035, the internal lumen 2035 is annular with a cross-sectional area that is much smaller than the cross-sectional area of the internal lumen 2035 when the dowel is not present. Thus, flow resistance increases when the dowel 2040 is positioned in the internal lumen 2035. The annular internal lumen 2035 has a length S that can be varied by varying the portion of the dowel 2040 that is inserted into the lumen 2035. Thus, as more of the dowel 2040 is inserted, the length S of the annular lumen 2035 increases and vice-versa. This can be used to vary the level of flow resistance caused by the presence of the dowel 2040.

The dowel 2040 enters the internal lumen 2035 via a hemostasis valve in the housing 2030. A cap 2050 and an O-ring 2055 provide a sealing engagement that seals the housing 2030 and dowel 2040 against leakage. The cap 2050 may have a locking feature, such as threads, that can be used to lock the cap 2050 against the housing 2030 and to also fix the position of the dowel 2040 in the housing 2040. When the cap 2050 is locked or tightened, the cap 2050 exerts pressure against the O-ring 2055 to tighten it against the dowel 2040 in a sealed engagement. When the cap 2050 is unlocked or untightened, the dowel 2040 is free to move in and out of the housing 2030.

Exemplary Methods of Use

Referring now to FIGS. 21A-21E, flow through the carotid artery bifurcation at different stages of the methods of the present disclosure will be described. Initially, as shown in FIG. 21A, the distal sheath 605 of the arterial access device 110 is introduced into the common carotid artery CCA. As mentioned, entry into the common carotid artery CCA can be via a transcervical or transfemoral approach. After the sheath 605 of the arterial access device 110 has been introduced into the common carotid artery CCA, the blood flow will continue in antegrade direction AG with flow from the common carotid artery entering both the internal carotid artery ICA and the external carotid artery ECA, as shown in FIG. 21A.

The venous return device 115 is then inserted into a venous return site, such as the internal jugular vein IJV (not shown in FIGS. 21A-21E). The shunt 120 is used to connect the flow lines 615 and 915 of the arterial access device 110 and the venous return device 115, respectively (as shown in FIG. 1A). In this manner, the shunt 120 provides a passageway for retrograde flow from the atrial access device 110 to the venous return device 115. In another embodiment, the shunt 120 connects to an external receptacle 130 rather than to the venous return device 115, as shown in FIG. 1C.

Once all components of the system are in place and connected, flow through the common carotid artery CCA is stopped, typically using the occlusion element 129 as shown in FIG. 21B. The occlusion element 129 is expanded at a location proximal to the distal opening of the sheath 605 to occlude the CCA. Alternately, the tourniquet 2105 (FIG. 1A) or other external vessel occlusion device can be used to occlude the common carotid artery CCA to stop flow therethrough. In an alternative embodiment, the occlusion element 129 is introduced on second occlusion device 112 separate from the distal sheath 605 of the arterial access device 110, as shown in FIG. 2B. The ECA may also be occluded with a separate occlusion element, either on the same device 110 or on a separate occlusion device.

At that point retrograde flow RG from the external carotid artery ECA and internal carotid artery ICA will begin and will flow through the sheath 605, the flow line 615, the shunt 120, and into the venous return device 115 via the flow line 915. The flow control assembly 125 regulates the retrograde flow as described above. FIG. 21B shows the occurrence of retrograde flow RG. While the retrograde flow is maintained, a stent delivery catheter 2110 is introduced into the sheath 605, as shown in FIG. 21C. The stent delivery catheter 2110 is introduced into the sheath 605 through the hemostasis valve 615 and the proximal extension 610 (not shown in FIGS. 21A-21E) of the arterial access device 110. The stent delivery catheter 2110 is advanced into the internal carotid artery ICA and a stent 2115 deployed at the bifurcation B, as shown in FIG. 21D.

The rate of retrograde flow can be increased during periods of higher risk for emboli generation for example while the stent delivery catheter 2110 is being introduced and optionally while the stent 2115 is being deployed. The rate of retrograde flow can be increased also during placement and expansion of balloons for dilatation prior to or after stent deployment. An atherectomy can also be performed before stenting under retrograde flow.

Still further optionally, after the stent 2115 has been expanded, the bifurcation B can be flushed by cycling the retrograde flow between a low flow rate and high flow rate. The region within the carotid arteries where the stent has been deployed or other procedure performed may be flushed with blood prior to reestablishing normal blood flow. In particular, while the common carotid artery remains occluded, a balloon catheter or other occlusion element may be advanced into the internal carotid artery and deployed to fully occlude that artery. The same maneuver may also be used to perform a post-deployment stent dilatation, which is typically done currently in self-expanding stent procedures. Flow from the common carotid artery and into the external carotid artery may then be reestablished by temporarily opening the occluding means present in the artery. The resulting flow will thus be able to flush the common carotid artery which saw slow, turbulent, or stagnant flow during carotid artery occlusion into the external carotid artery. In addition, the same balloon may be positioned distally of the stent during reverse flow and forward flow then established by temporarily relieving occlusion of the common carotid artery and flushing. Thus, the flushing action occurs in the stented area to help remove loose or loosely adhering embolic debris in that region.

Optionally, while flow from the common carotid artery continues and the internal carotid artery remains blocked, measures can be taken to further loosen emboli from the treated region. For example, mechanical elements may be used to clean or remove loose or loosely attached plaque or other potentially embolic debris within the stent, thrombolytic or other fluid delivery catheters may be used to clean the area, or other procedures may be performed. For example, treatment of in-stent restenosis using balloons, atherectomy, or more stents can be performed under retrograde flow In another example, the occlusion balloon catheter may include flow or aspiration lumens or channels which open proximal to the balloon. Saline, thrombolytics, or other fluids may be infused and/or blood and debris aspirated to or from the treated area without the need for an additional device. While the emboli thus released will flow into the external carotid artery, the external carotid artery is generally less sensitive to emboli release than the internal carotid artery. By prophylactically removing potential emboli which remain, when flow to the internal carotid artery is reestablished, the risk of emboli release is even further reduced. The emboli can also be released under retrograde flow so that the emboli flows through the shunt 120 to the venous system, a filter in the shunt 120, or the receptacle 130.

After the bifurcation has been cleared of emboli, the occlusion element 129 or alternately the tourniquet 2105 can be released, reestablishing antegrade flow, as shown in FIG. 21E. The sheath 605 can then be removed.

A self-closing element may be deployed about the penetration in the wall of the common carotid artery prior to withdrawing the sheath 605 at the end of the procedure. Usually, the self-closing element will be deployed at or near the beginning of the procedure, but optionally, the self-closing element could be deployed as the sheath is being withdrawn, often being released from a distal end of the sheath onto the wall of the common carotid artery. Use of the self-closing element is advantageous since it affects substantially the rapid closure of the penetration in the common carotid artery as the sheath is being withdrawn. Such rapid closure can reduce or eliminate unintended blood loss either at the end of the procedure or during accidental dislodgement of the sheath. In addition, such a self-closing element may reduce the risk of arterial wall dissection during access. Further, the self-closing element may be configured to exert a frictional or other retention force on the sheath during the procedure. Such a retention force is advantageous and can reduce the chance of accidentally dislodging the sheath during the procedure. A self-closing element eliminates the need for vascular surgical closure of the artery with suture after sheath removal, reducing the need for a large surgical field and greatly reducing the surgical skill required for the procedure.

The disclosed systems and methods may employ a wide variety of self-closing elements, typically being mechanical elements which include an anchor portion and a self-closing portion. The anchor portion may comprise hooks, pins, staples, clips, tine, suture, or the like, which are engaged in the exterior surface of the common carotid artery about the penetration to immobilize the self-closing element when the penetration is fully open. The self-closing element may also include a spring-like or other self-closing portion which, upon removal of the sheath, will close the anchor portion in order to draw the tissue in the arterial wall together to provide closure. Usually, the closure will be sufficient so that no further measures need be taken to close or seal the penetration. Optionally, however, it may be desirable to provide for supplemental sealing of the self-closing element after the sheath is withdrawn. For example, the self-closing element and/or the tissue tract in the region of the element can be treated with hemostatic materials, such as bioabsorbable polymers, collagen plugs, glues, sealants, clotting factors, or other clot-promoting agents. Alternatively, the tissue or self-closing element could be sealed using other sealing protocols, such as electrocautery, suturing, clipping, stapling, or the like. In another method, the self-closing element will be a self-sealing membrane or gasket material which is attached to the outer wall of the vessel with clips, glue, bands, or other means. The self-sealing membrane may have an inner opening such as a slit or cross cut, which would be normally closed against blood pressure. Any of these self-closing elements could be designed to be placed in an open surgical procedure, or deployed percutaneously.

In another embodiment, carotid artery stenting may be performed after the sheath is placed and an occlusion balloon catheter deployed in the external carotid artery. The stent having a side hole or other element intended to not block the ostium of the external carotid artery may be delivered through the sheath with a guidewire or a shaft of an external carotid artery occlusion balloon received through the side hole. Thus, as the stent is advanced, typically by a catheter being introduced over a guidewire which extends into the internal carotid artery, the presence of the catheter shaft in the side hole will ensure that the side hole becomes aligned with the ostium to the external carotid artery as the stent is being advanced. When an occlusion balloon is deployed in the external carotid artery, the side hole prevents trapping the external carotid artery occlusion balloon shaft with the stent which is a disadvantage of the other flow reversal systems. This approach also avoids "jailing" the external carotid artery, and if the stent is covered with a graft material, avoids blocking flow to the external carotid artery.

In another embodiment, stents are placed which have a shape which substantially conforms to any preexisting angle between the common carotid artery and the internal carotid artery. Due to significant variation in the anatomy among patients, the bifurcation between the internal carotid artery and the external carotid artery may have a wide variety of angles and shapes. By providing a family of stents having differing geometries, or by providing individual stents which may be shaped by the physician prior to deployment, the physician may choose a stent which matches the patient's particular anatomy prior to deployment. The patient's anatomy may be determined using angiography or by other conventional means. As a still further alternative, the stent may have sections of articulation. These stents may be placed first and then articulated in situ in order to match the angle of bifurcation between a common carotid artery and internal carotid artery. Stents may be placed in the carotid arteries, where the stents have a sidewall with different density zones.

In another embodiment, a stent may be placed where the stent is at least partly covered with a graft material at either or both ends. Generally, the stent will be free from graft material and the middle section of the stent which will be deployed adjacent to the ostium to the external carotid artery to allow blood flow from the common carotid artery into the external carotid artery.

In another embodiment, a stent delivery system can be optimized for transcervical access by making them shorter and more rigid than systems designed for transfemoral access. These changes will improve the ability to torque and position the stent accurately during deployment. In addition, the stent delivery system can be designed to align the stent with the ostium of the external carotid artery, either by using the external carotid occlusion balloon or a separate guide wire in the external carotid artery, which is especially useful with stents with sideholes or for stents with curves, bends, or angulation where orientation is critical.

In certain embodiments, the shunt is fixedly connected to the arterial access sheath and the venous return sheath so that the entire assembly of the replaceable flow assembly and sheaths may be disposable and replaceable as a unit. In other instances, the flow control assembly may be removably attached to either or both of the sheaths.

In an embodiment, the user first determines whether any periods of heightened risk of emboli generation may exist during the procedure. As mentioned, some exemplary periods of heightened risk include (1) during periods when the plaque P is being crossed by a device; (2) during an interventional procedure, such as during delivery of a stent or during inflation or deflation of a balloon catheter or guidewire; (3) during injection or contrast. The foregoing are merely examples of periods of heightened risk. During such periods, the user sets the retrograde flow at a high rate for a discreet period of time. At the end of the high risk period, or if the patient exhibits any intolerance to the high flow rate, then the user reverts the flow state to baseline flow. If the system has a timer, the flow state automatically reverts to baseline flow after a set period of time. In this case, the user may re-set the flow state to high flow if the procedure is still in a period of heightened embolic risk.

In another embodiment, if the patient exhibits an intolerance to the presence of retrograde flow, then retrograde flow is established only during placement of a filter in the ICA distal to the plaque P. Retrograde flow is then ceased while an interventional procedure is performed on the plaque P. Retrograde flow is then re-established while the filter is removed. In another embodiment, a filter is places in the ICA distal of the plaque P and retrograde flow is established while the filter is in place. This embodiment combines the use of a distal filter with retrograde flow.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method for accessing and treating a carotid artery, comprising:
   inserting an arterial access sheath into a patient's neck and through a wall of a common carotid artery at an arterial access site, wherein the arterial access sheath has a structural configuration that limits a depth of insertion of a distal portion of the arterial access sheath into the common carotid artery;
   positioning a filter in an internal carotid artery distal of a location of treatment; and
   inserting an interventional device into the common carotid artery via the arterial access sheath;
   wherein structural configuration of the arterial access sheath limits the distal portion the from being inserted into the common carotid artery beyond a length such that the distal portion would contact a bifurcation location where the patient's common carotid artery bifurcates into an internal carotid artery and external carotid artery.

2. The method of claim 1, wherein the arterial access site is located at distance of 5 cm to 7 cm below the bifurcation location where the patient's common carotid artery bifurcates into an internal carotid artery and external carotid artery.

3. The method of claim 2, wherein the arterial access sheath has a working length of 5 cm to 15 cm and further comprising inserting no more than the working length of the arterial access sheath into the common carotid artery.

4. The method of claim 1, wherein the structural configuration of the arterial access sheath includes a stopper member that at least partially covers the distal portion and that limits insertion of the distal portion into the common carotid artery.

5. The method of claim 1, further comprising establishing reverse blood flow through the common carotid artery.

6. The method of claim 1, further comprising blocking blood flow through at least a portion of the common carotid artery.

7. A system for use in accessing and treating a carotid artery, said system comprising:
   an arterial access sheath adapted to be introduced into a common carotid artery via a neck of a patient and receive blood flow from the common carotid artery, the arterial access sheath including a distal sheath portion adapted to enter the common carotid artery, wherein the distal sheath portion has a structural configuration that limits a depth of insertion of a distal portion of the arterial access sheath into the common carotid artery; and
   a filter adapted to be positioned in an internal carotid artery distal of a location of treatment;

wherein the structural configuration of the arterial access sheath limits the distal portion from being inserted into the common carotid artery beyond a length such that the distal portion would contact a bifurcation location where the patient's common carotid artery bifurcates into an internal carotid artery and external carotid artery.

8. The method of claim 7, wherein structural configuration of the arterial access sheath limits the distal portion the from being inserted into the common carotid artery beyond a length that would disrupt plaque in the common carotid artery.

9. The system of claim 7, wherein the arterial access sheath has a distal region with a reduced luminal diameter to facilitate introduction into the common carotid artery and a proximal region having a larger luminal diameter relative to the distal region to decrease overall flow resistance through the arterial access sheath.

10. The system of claim 7, wherein the structural configuration comprises a stopper member that at least partially covers the distal portion and that limits insertion of the distal portion into the common carotid artery.

11. The system of claim 7, wherein the arterial access site is located at distance of 5 cm to 7 cm below the bifurcation location where the patient's common carotid artery bifurcates into an internal carotid artery and external carotid artery.

12. The system of claim 11, wherein the arterial access sheath has a working length of 5 cm to 15 cm and further comprising inserting no more than the working length of the arterial access sheath into the common carotid artery.

13. The system of claim 7, further comprising:
a shunt fluidly connected to the arterial access sheath, wherein the shunt provides a pathway for blood to flow from the arterial access sheath to a return site.

14. A method for accessing and treating a carotid artery, comprising:
inserting an arterial access sheath into a patient's neck and through a wall of a common carotid artery at an arterial access site, wherein the arterial access sheath has a structural configuration that limits a depth of insertion of a distal portion of the arterial access sheath into the common carotid artery;
positioning a filter in an internal carotid artery distal of a location of treatment; and
inserting an interventional device into the common carotid artery via the arterial access sheath;
wherein structural configuration of the arterial access sheath limits the distal portion the from being inserted into the common carotid artery beyond a length that would disrupt plaque in the common carotid artery.

15. The method of claim 14, wherein the arterial access site is located at distance of 5 cm to 7 cm below the bifurcation location where the patient's common carotid artery bifurcates into an internal carotid artery and external carotid artery.

16. The method of claim 15, wherein the arterial access sheath has a working length of 5 cm to 15 cm and further comprising inserting no more than the working length of the arterial access sheath into the common carotid artery.

17. The method of claim 14, wherein the structural configuration of the arterial access sheath includes a stopper member that at least partially covers the distal portion and that limits insertion of the distal portion into the common carotid artery.

18. The method of claim 14, further comprising establishing reverse blood flow through the common carotid artery.

19. The method of claim 14, further comprising blocking blood flow through at least a portion of the common carotid artery.

20. A system for use in accessing and treating a carotid artery, said system comprising:
an arterial access sheath adapted to be introduced into a common carotid artery via a neck of a patient and receive blood flow from the common carotid artery, the arterial access sheath including a distal sheath portion adapted to enter the common carotid artery, wherein the distal sheath portion has a structural configuration that limits a depth of insertion of a distal portion of the arterial access sheath into the common carotid artery; and
a filter adapted to be positioned in an internal carotid artery distal of a location of treatment;
wherein structural configuration of the arterial access sheath limits the distal portion the from being inserted into the common carotid artery beyond a length that would disrupt plaque in the common carotid artery.

21. The system of claim 20, wherein the arterial access sheath has a distal region with a reduced luminal diameter to facilitate introduction into the common carotid artery and a proximal region having a larger luminal diameter relative to the distal region to decrease overall flow resistance through the arterial access sheath.

22. The system of claim 20, wherein the structural configuration comprises a stopper member that at least partially covers the distal portion and that limits insertion of the distal portion into the common carotid artery.

23. The system of claim 20, wherein the arterial access site is located at distance of 5 cm to 7 cm below the bifurcation location where the patient's common carotid artery bifurcates into an internal carotid artery and external carotid artery.

24. The system of claim 23, wherein the arterial access sheath has a working length of 5 cm to 15 cm and further comprising inserting no more than the working length of the arterial access sheath into the common carotid artery.

25. The system of claim 23, further comprising:
a shunt fluidly connected to the arterial access sheath, wherein the shunt provides a pathway for blood to flow from the arterial access sheath to a return site.

26. A system for use in accessing and treating a carotid artery, said system comprising:
an arterial access sheath adapted to be introduced into a common carotid artery via a neck of a patient and receive blood flow from the common carotid artery, the arterial access sheath including a distal sheath portion adapted to enter the common carotid artery, wherein the distal sheath portion has a structural configuration that limits a depth of insertion of a distal portion of the arterial access sheath into the common carotid artery; and
a filter adapted to be positioned in an internal carotid artery distal of a location of treatment;
wherein the arterial access sheath has a distal region with a reduced luminal diameter to facilitate introduction into the common carotid artery and a proximal region having a larger luminal diameter relative to the distal region to decrease overall flow resistance through the arterial access sheath.

27. The system of claim 26, wherein the structural configuration comprises a stopper member that at least partially covers the distal portion and that limits insertion of the distal portion into the common carotid artery.

28. The system of claim 26, wherein the arterial access site is located at distance of 5 cm to 7 cm below the bifurcation location where the patient's common carotid artery bifurcates into an internal carotid artery and external carotid artery.

29. The system of claim 28, wherein the arterial access sheath has a working length of 5 cm to 15 cm and further comprising inserting no more than the working length of the arterial access sheath into the common carotid artery.

30. The system of claim 26, further comprising:
a shunt fluidly connected to the arterial access sheath, wherein the shunt provides a pathway for blood to flow from the arterial access sheath to a return site.

31. A method for accessing and treating an artery, comprising:
inserting an arterial access sheath into a patient's neck and through a wall of a common carotid artery at an arterial access site, wherein the arterial access sheath has a structural configuration that limits a depth of insertion of a distal portion of the arterial access sheath into the common carotid artery;
positioning a filter in an internal carotid artery distal of a location of treatment; and
inserting an interventional device into the common carotid artery via the arterial access sheath;
wherein structural configuration of the arterial access sheath limits the distal portion the from being inserted into the common carotid artery beyond a length such that the distal portion would contact a bifurcation location where the patient's common carotid artery bifurcates into an internal carotid artery and external carotid artery.

32. The method of claim 31, wherein the arterial access site is located at distance of 5 cm to 7 cm below the bifurcation location where the patient's common carotid artery bifurcates into an internal carotid artery and external carotid artery.

33. The method of claim 31, wherein the structural configuration of the arterial access sheath includes a stopper member that at least partially covers the distal portion and that limits insertion of the distal portion into the common carotid artery.

34. The method of claim 31, further comprising establishing reverse blood flow through at least the common carotid artery.

35. A system for use in accessing and treating an artery, said system comprising:
an arterial access sheath adapted to be introduced into a common carotid artery via a neck of a patient and receive blood flow from the common carotid artery, the arterial access sheath including a distal sheath portion adapted to enter the common carotid artery, wherein the distal sheath portion has a structural configuration that limits a depth of insertion of a distal portion of the arterial access sheath into the common carotid artery; and
a filter adapted to be positioned in an internal carotid artery distal of a location of treatment;
wherein the structural configuration of the arterial access sheath limits the distal portion from being inserted into the common carotid artery beyond a length such that the distal portion would contact a bifurcation location where the patient's common carotid artery bifurcates into an internal carotid artery and external carotid artery.

36. The method of claim 35, wherein structural configuration of the arterial access sheath limits the distal portion the from being inserted into the common carotid artery beyond a length that would disrupt plaque in the common carotid artery.

37. The system of claim 35, wherein the arterial access sheath has a distal region with a reduced luminal diameter to facilitate introduction into the common carotid artery and a proximal region having a larger luminal diameter relative to the distal region to decrease overall flow resistance through the arterial access sheath.

38. The system of claim 35, wherein the structural configuration comprises a stopper member that at least partially covers the distal portion and that limits insertion of the distal portion into the common carotid artery.

39. The system of claim 35, further comprising:
a shunt fluidly connected to the arterial access sheath, wherein the shunt provides a pathway for blood to flow from the arterial access sheath to a return site.

40. A method for accessing and treating an artery, comprising:
inserting an arterial access sheath into a patient's neck and through a wall of a common carotid artery at an arterial access site, wherein the arterial access sheath has a structural configuration that limits a depth of insertion of a distal portion of the arterial access sheath into the common carotid artery;
positioning a filter in an internal carotid artery distal of a location of treatment; and
inserting an interventional device into the common carotid artery via the arterial access sheath;
wherein structural configuration of the arterial access sheath limits the distal portion the from being inserted into the common carotid artery beyond a length that would disrupt plaque in an artery.

41. The method of claim 40, wherein the arterial access site is located at distance of 5 cm to 7 cm below the bifurcation location where the patient's common carotid artery bifurcates into an internal carotid artery and external carotid artery.

42. The method of claim 41, wherein the arterial access sheath has a working length of 5 cm to 15 cm and further comprising inserting no more than the working length of the arterial access sheath into the common carotid artery.

43. The method of claim 40, wherein the structural configuration of the arterial access sheath includes a stopper member that at least partially covers the distal portion and that limits insertion of the distal portion into the common carotid artery.

44. The method of claim 40, further comprising establishing reverse blood flow through at least the common carotid artery.

45. The method of claim 40, further comprising blocking blood flow through at least a portion of the common carotid artery.

46. A system for use in accessing and treating an artery, said system comprising:
an arterial access sheath adapted to be introduced into a common carotid artery via a neck of a patient and receive blood flow from the common carotid artery, the arterial access sheath including a distal sheath portion adapted to enter the common carotid artery, wherein the distal sheath portion has a structural configuration that limits a depth of insertion of a distal portion of the arterial access sheath into the common carotid artery; and a filter adapted to be positioned in an internal carotid artery distal of a location of treatment;

wherein structural configuration of the arterial access sheath limits the distal portion the from being inserted into the common carotid artery beyond a length that would disrupt plaque in the common carotid artery.

47. The system of claim 46, wherein the arterial access sheath has a distal region with a reduced luminal diameter to facilitate introduction into the common carotid artery and a proximal region having a larger luminal diameter relative to the distal region to decrease overall flow resistance through the arterial access sheath.

48. The system of claim 46, wherein the structural configuration comprises a stopper member that at least partially covers the distal portion and that limits insertion of the distal portion into the common carotid artery.

49. The system of claim 46, wherein the arterial access site is located at distance of 5 cm to 7 cm below the bifurcation location where the patient's common carotid artery bifurcates into an internal carotid artery and external carotid artery.

50. The system of claim 46, further comprising:

a shunt fluidly connected to the arterial access sheath, wherein the shunt provides a pathway for blood to flow from the arterial access sheath to a return site.

51. A system for use in accessing and treating an artery, said system comprising:

an arterial access sheath adapted to be introduced into a common carotid artery via a neck of a patient and receive blood flow from the common carotid artery, the arterial access sheath including a distal sheath portion adapted to enter the common carotid artery, wherein the distal sheath portion has a structural configuration that limits a depth of insertion of a distal portion of the arterial access sheath into the common carotid artery; and a filter adapted to be positioned in an internal carotid artery distal of a location of treatment;

wherein the arterial access sheath has a distal region with a reduced luminal diameter to facilitate introduction into the common carotid artery and a proximal region having a larger luminal diameter relative to the distal region to decrease overall flow resistance through the arterial access sheath.

52. The system of claim 51, wherein the structural configuration comprises a stopper member that at least partially covers the distal portion and that limits insertion of the distal portion into the common carotid artery.

53. The system of claim 51, wherein the arterial access site is located at distance of 5 cm to 7 cm below the bifurcation location where the patient's common carotid artery bifurcates into an internal carotid artery and external carotid artery.

54. The system of claim 53, wherein the arterial access sheath has a working length of 5 cm to 15 cm and further comprising inserting no more than the working length of the arterial access sheath into the common carotid artery.

55. The system of claim 51, further comprising:

a shunt fluidly connected to the arterial access sheath, wherein the shunt provides a pathway for blood to flow from the arterial access sheath to a return site.

* * * * *